(12) United States Patent
Maresca et al.

(10) Patent No.: US 9,488,592 B1
(45) Date of Patent: Nov. 8, 2016

(54) AUTOMATIC DETECTION OF DEFECTS IN COMPOSITE STRUCTURES USING NDT METHODS

(71) Applicant: Kurion, Inc., Irvine, CA (US)

(72) Inventors: Joseph W. Maresca, Sunnyvale, CA (US); Wilhelmina C. Leuschen, Kennewick, WA (US); Marissa L. Ammer, Pasco, WA (US)

(73) Assignee: Kurion, Inc., Irvine, CA (US)

( * ) Notice: Subject to any disclaimer, the term of this patent is extended or adjusted under 35 U.S.C. 154(b) by 863 days.

(21) Appl. No.: 13/631,795

(22) Filed: Sep. 28, 2012

Related U.S. Application Data

(60) Provisional application No. 61/540,463, filed on Sep. 28, 2011.

(51) Int. Cl.
*H04N 7/18* (2006.01)
*G01N 21/88* (2006.01)

(52) U.S. Cl.
CPC .................................. *G01N 21/8851* (2013.01)

(58) Field of Classification Search
CPC ............................ G01N 21/88; G01N 21/956
USPC ......................................................... 348/125
See application file for complete search history.

(56) References Cited

U.S. PATENT DOCUMENTS

| 6,378,387 B1* | 4/2002 | Froom | G01M 5/0016 73/865.8 |
| 2005/0207468 A1* | 9/2005 | McCullough | G01N 25/72 374/5 |
| 2005/0264796 A1* | 12/2005 | Shaw | G01B 11/162 356/237.2 |
| 2012/0303056 A1* | 11/2012 | Li | C08L 25/08 606/213 |

* cited by examiner

*Primary Examiner* — Chikaodili E Anyikire
(74) *Attorney, Agent, or Firm* — Schwabe, Williamson & Wyatt

(57) ABSTRACT

A method and an apparatus for automatically collecting and processing nondestructive test (NDT) data to determine the presence, type, location, size, and strength of defects in composite, honeycomb, and grid structures like those found in aircraft, wind blades, boats, cars, building structures. The preferred embodiment is comprised of an uncooled IR mounted on a frame, a conductive heating mat, an IR Ruler with fiducials in a recognizable pattern, a computer, a processor, and output displays. The data collection, processing, and display output can be controlled or reviewed remotely via the internet. The processing, location, and output displays can be applied to any NDT system that collects and processes a two-dimensional amplitude image (e.g., x-ray systems).

52 Claims, 61 Drawing Sheets

InspectionSetup

Inspection Setup

| Site Identifier: | RAFB |
| --- | --- |
| Facility: | BLDG. 145 |
| Type of Aircraft: | F-15 |
| Component of Aircraft: | VS |
| Item Serial Number: | 00255 |
| Operator 1: | WCL |
| Operator 2: | MDA |

Inspection Identification: 20120503132052

Vertical Stabilizer Selected: Right Outboard ▾

Location Method: IR Ruler ▾

Comment: Warm, sunny day.

[Continue] [Cancel]

FIG. 16

AUTOMATIC DETECTION OF DEFECTS IN COMPOSITE STRUCTURES USING NDT METHODS

CROSS-REFERENCE TO RELATED APPLICATIONS

This application claims priority to U.S. Provisional Application No. 61/540,463 filed Sep. 28, 2011, the contents of which is incorporated herein by reference in its entirety.

BACKGROUND OF THE INVENTION

1. Field of the Invention

Method and apparatuses for automatic, real-time nondestructive testing (NDT) of composite, honeycomb, and gridlock structures using thermography to determine the presence, type, location, size, and strength of defects in the composite structure without having to visually interpret raw infrared (IR) images. The present invention is motivated by the types of composite structures found on aircraft but the method and apparatuses apply to any structure comprised all or partially of composite materials such as wind blades, boats, cars, and building materials. The NDT method and apparatuses of the present invention are comprised of an IR camera, a heating or cooling method to change the temperature of the composite structure relative to the ambient temperature in such a way as to produce detectable IR intensity changes in the region of the defect, an electronic ruler to determine the location of the IR images on the composite structure, a computer, noise cancellation signal processing algorithms and software, and tabular and graphical output displays. The processing, location, and output displays can be applied to any NDT system that collects and processes a two dimensional amplitude images (e.g., x-ray systems).

2. Brief Description of Prior Art

Composite materials, such as boron, Kevlar, graphite, and carbon materials, are widely used in many advanced aircraft, automobile, ship, and construction structural systems. Reliable damage assessment for these structures, especially aircraft structures, which are subject to wear and tear, including extreme operational conditions, is one of the most serious and costly problems faced in the field of maintenance. This problem is compounded by the fact that damage can occur in many different forms. Reliable systems for detecting damage are particularly important for older and aging systems where structural failure may have significant losses of life or money.

Damage in composites can be detected in numerous ways, but the conventional detection methods are frequently limited to certain kinds of materials and structural geometries, and they are usually weak at quantifying the type of damage. In addition, these methods often require the structure to be at least partially disassembled so that a skilled technician can interpret the results of the inspection measurements. This increases the labor costs and adds to the time needed to complete the inspection. Improved inspection systems need to address defect signature analysis with a view to implementing an automated defect identification, extraction, and classification methodology (e.g., disbonds, delamination and water penetration into the honeycomb) that will ensure minimum operator intervention. The operator should only be needed to verify the presence of a defect by inspecting the IR video images manually after they are processed in real time using advanced signal processing methods.

The method and apparatuses of the present invention are motivated by the need for automatic, portable, easy-to-use, and low-cost methods of NDT inspection of the composite structures on aircraft, automobiles, ships, and construction that are fast, accurate, and reliable. Many of the NDT methods require highly skilled technicians to both perform the inspection and interpret the results of the inspection from visual analysis of raw sensor images. For these reasons, NDT inspection using thermography, which has been around for many years, has not gained the same acceptance and market share as some of the other methods. This is a problem, because thermography can detect and identify all of the defects of interest, which is not possible with many of the other methods.

The measurement benefits of thermography methods can be realized if the method can be more efficiently and accurately implemented. The spatial coverage and the ability to distinguish and identify between defects offers significant advantages over other NDT methods like x-ray, acoustic, and coin tap testing inspection methods. For example, thermography methods can detect disbonds and delamination in honeycomb composite aircraft structures, including beneath repaired and refurbished areas. Such measurements are not possible with x-ray methods. While x-ray methods can detect the presence of water or moisture in a honeycomb structure, they cannot differentiate the water or moisture from a buildup of epoxy that can be done with thermography methods. Acoustic methods, which require the application (and cleanup) of gel to the surface before making point measurements with a small probe are operationally messy and slow. Thermography methods cover larger spatial areas (vice point measurements) and do not require the application of gel or any preparation of the surface like paint removal. Thermography methods can also determine what the detected defect is (i.e., disbond, delamination, fluid ingress, epoxy), while other methods cannot (e.g., coin tap test).

FIG. 9 illustrates the output of a raw IR image obtained 30 s after heating the surface of an aircraft honeycomb boron composite used in the vertical stabilizer of the US Air Force (USAF) F-15 jet aircraft shown in FIG. 1. An illustration of a section of the honeycomb boron composite 20 is shown in FIG. 2. The boron composite 26 over the honeycomb 28 and the aluminum skin 24 over the honeycomb is shown. Distinct white spots in the IR image can indicate the presence of a disbond (separation of the boron composite from the aluminum honeycomb) or a delamination (separation between one or more layers of the boron composite). Visual inspection of the IR image indicates many such areas and significant ambiguity. FIG. 10 illustrates the results of the same IR image processed with a computer using a noise cancellation background removal method. One can easily see the disbond along the right edge of the aircraft structure and not be confused by the large area of ambiguous white spots along the left edge and center sections of the composite structure. This simple illustration shows the benefit of signal processing methods over visual interpretation in terms of accuracy and reliability. It minimizes the number of false detections (i.e., false alarms). It is also significant that the computer analysis is done automatically and can be done remotely without having to output the IR image.

The method and apparatuses of the present invention improve the performance, completely automate, and make it easy to use thermography for inspection of composite structures like those found on military and commercial aircraft. Skilled technicians are not needed for the operational implementation of the method in the field or for interpretation of the results. Such skilled interpretation can be reserved for validation and confirmation of the results. Because of the larger spatial coverage than other NDT techniques and the ability to determine the measurement coverage and locate defects on the composite structure itself automatically, thermography methods can be used to reduce the time and cost of an inspection.

The methods and apparatuses of the present invention also improve upon existing thermograph methods in terms of speed, accuracy, and cost because of the automation and signal processing. For example, automation is possible because of the noise cancellation, which effectively identifies and mitigates false alarms (false defects) and sources of interference from false targets like rivets and seams between materials.

SUMMARY OF THE INVENTION

It is the object of this invention to provide a method and apparatuses for inspection of composite structures to detect the presence of defects within and between composite structures.

It is the object of this invention to provide a method and apparatuses for inspection of aircraft composites, including honeycomb structures with aluminum or composite surface skins, tongue and groove gridlock structures, and composite structures comprised of various composite and core layers.

It is also the object of this invention to provide a method and apparatuses for detecting, identifying, locating, and determining the size of defects like delamination, disbonds, and fluid ingress in composite honeycomb structures like those found on aircraft.

It is another object of this invention to provide a method and apparatuses for inspection of composites automatically without the need for visual interpretation of the amplitude images.

It is still another object of this invention to provide a method for automatically determining whether or not a defect is present in the composite materials through the application of signal processing algorithms implemented on a computer.

It is another object of this invention to provide a method and apparatuses for automatic location of the inspection of the image coverage area and any defects within the image referenced to a physical location on the structure being inspected.

The present invention is an NDT thermography method, which can be implemented in a number of apparatuses using an uncooled IR camera to detect, identify, locate, and determine the size of defects in composite materials automatically and in real-time without having to interpret raw IR images. The system was motivated by the need to inspect a variety of military and commercial aircraft structures, which structures include honeycomb structures with aluminum or composite surface skins, tongue and groove gridlock structures, and composite structures comprised of various composite and core layers. The method works on any type of composite materials. The preferred embodiment is comprised of an uncooled IR camera, a heating or cooling method to change the temperature of the composite structure relative to the ambient temperature in such a way as to produce detectable IR intensity changes in the region of the defect, an electronic ruler to determine the coverage and location of the IR images and any defects detected on the composite structure, a computer to collect, process, and output the results as the NDT inspection is being performed. Only a small temperature change in the surface of the composite structure is needed to produce detectable IR signals, and heating the surface for a short time period (e.g., 10 s) will suffice. A silicone heating mat, which conductively heats the surface of the composite, is the preferred heating method, but convective and radiant heating and cooling methods are equally effective. The processing includes removal of the background noise, including the IR response from uneven heating, using a noise cancellation method based on a median filter. The coverage and location of any defects on the composite structure is done automatically using a special IR Ruler, which is placed on the composite structure before the measurements are made. The IR camera and heating method can be implemented as an integrated stand-alone system on a frame, or as separate handheld units. The entire inspection can be performed automatically without the need for the operator to manually interpret IR images or manually locate the defects and the area covered on the composite structure.

The method and apparatuses of the present invention are able to detect defects in aluminum honeycomb composite structures like those found on the vertical stabilizer of an F-15 aircraft such as disbonds (separation between the surface composite layers and the aluminum honeycomb), delaminations (separation of the layers in the composite layers), and regions of fluid ingress (fluid within a honeycomb structure), and is capable of distinguishing fluid from a buildup of epoxy. FIG. 3 illustrates the use of the preferred embodiment of the present invention on an F-15 vertical stabilizer, which will be referred to as the IR Inspection System (IRIS), and the graphical output of the inspection showing the inspection coverage and the location and identification of the type of defect on the stabilizer. The method and apparatuses are also able to detect defects in composite structures like graphite nomex, a thin-walled aluminum honeycomb structure and wind blades, including delamination and/or separation of the composite layers and/or the core material from the composite itself. Finally, the method and apparatuses are able to detect voids in the epoxy or damaged channel sections in gridlock structures.

BRIEF DESCRIPTION OF THE DRAWINGS

FIG. 16 illustrates the Inspection Setup window of the IRIS graphical user interface.

DESCRIPTION OF THE PREFERRED EMBODIMENT

Figure 2:
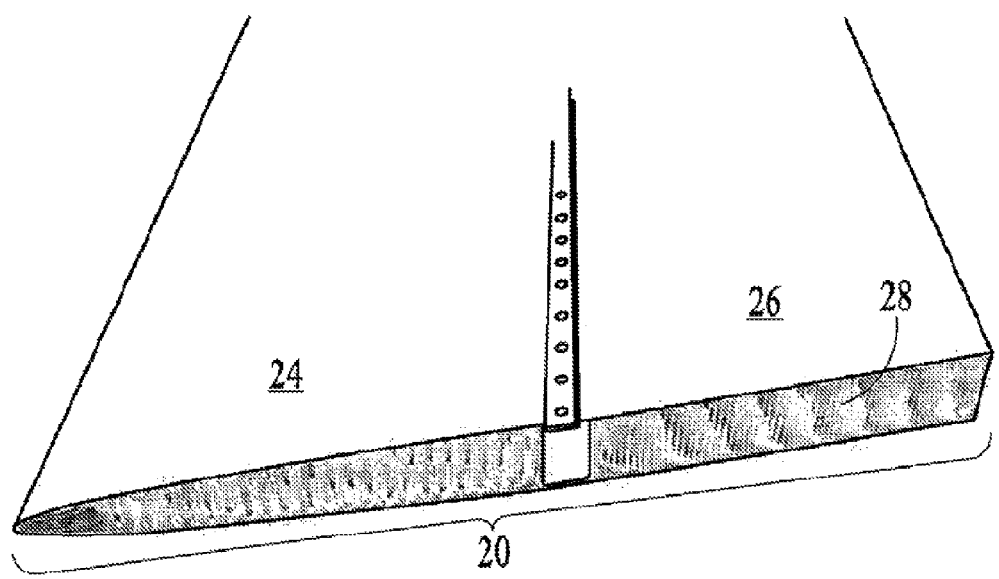
FIG. 2 illustrates the internal structure of an article with a boron composite skin over an internal aluminum honeycomb.
Figure 3:
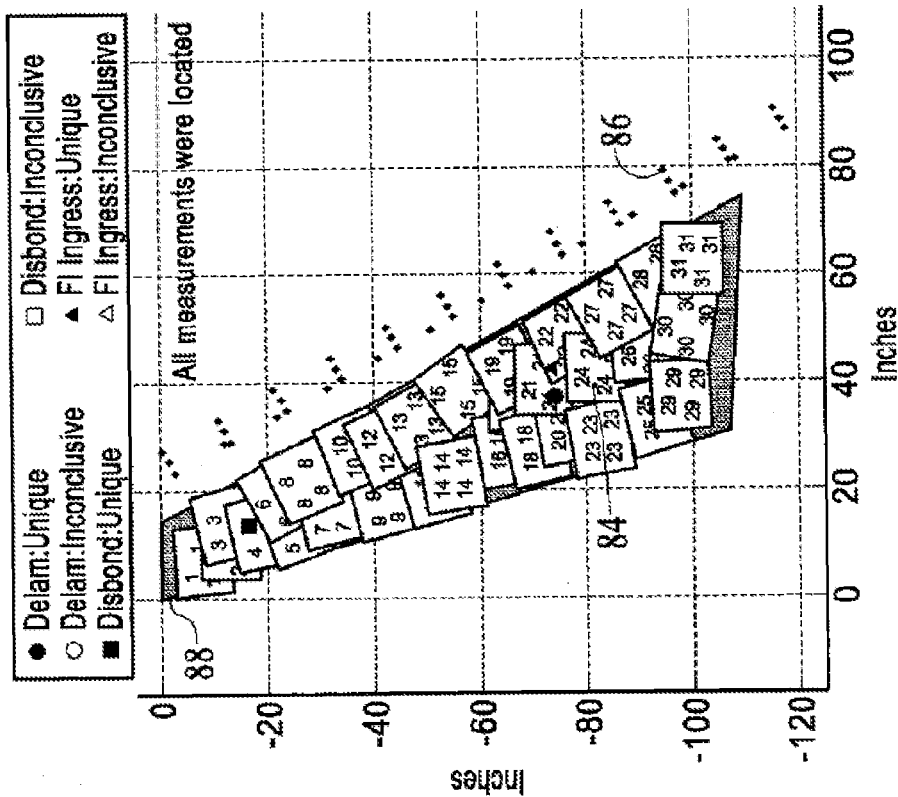
FIG. 3 illustrates the IRIS system in used on an actual F-15 with a defect and image coverage map shown on the right.
Figure 3:
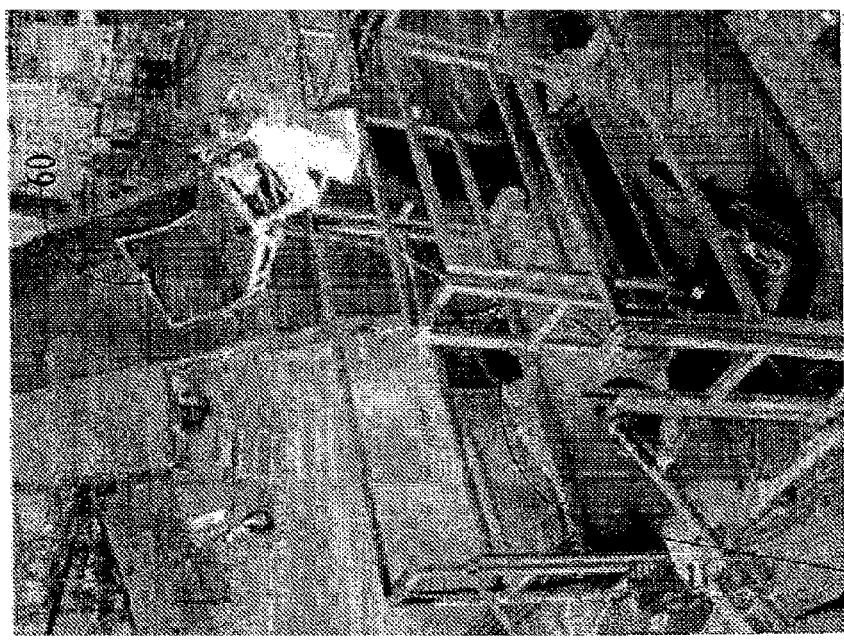
Figure 4:
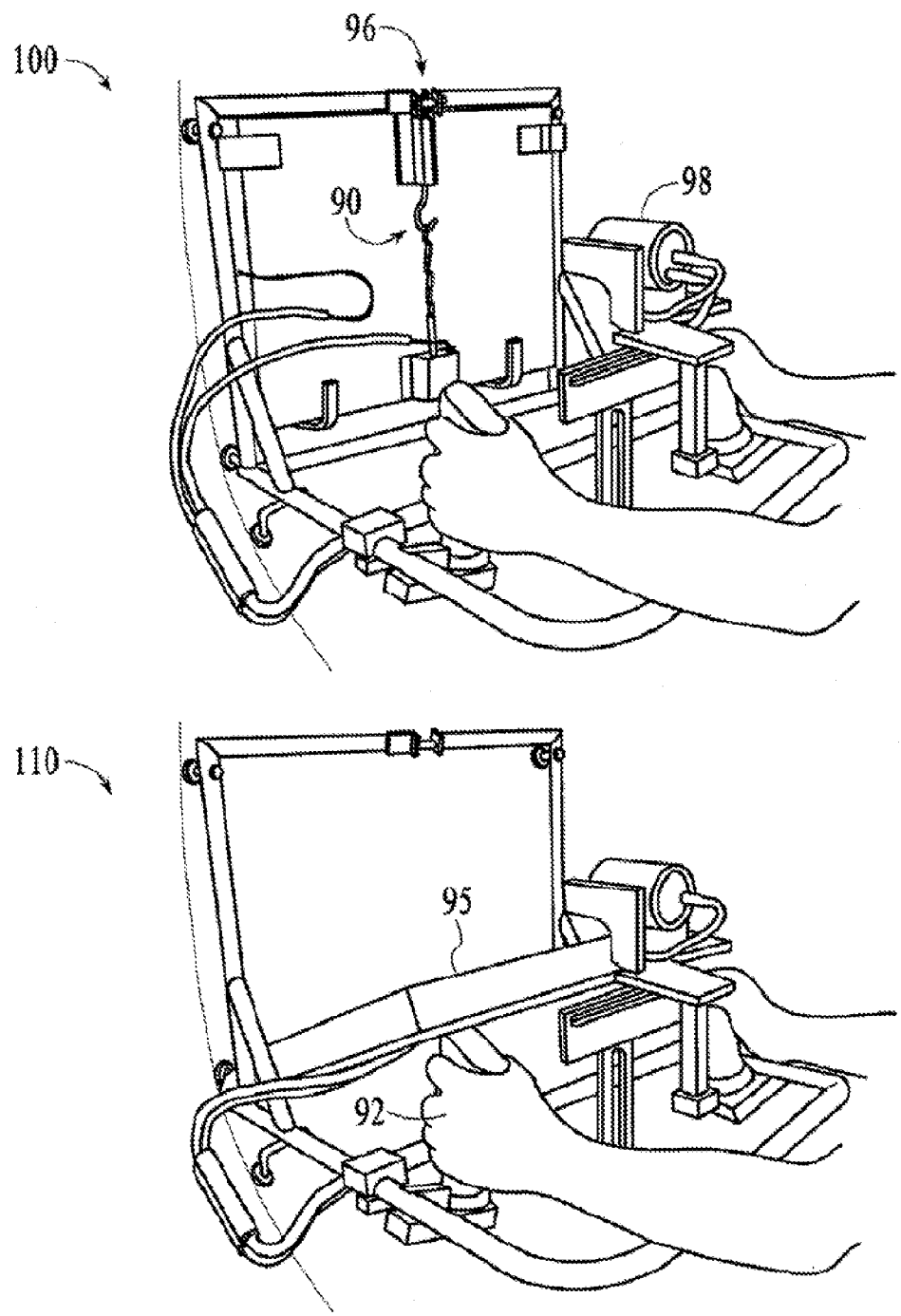
FIG. 4 illustrates the IR inspection method with heat being applied to the surface of the boron honeycomb composite on an F-15 vertical stabilizer in the lab and after the latch was released so that the heating mat fell out of the way of the IR camera and IR measurements of the composite surface could take place.
Figure 5:
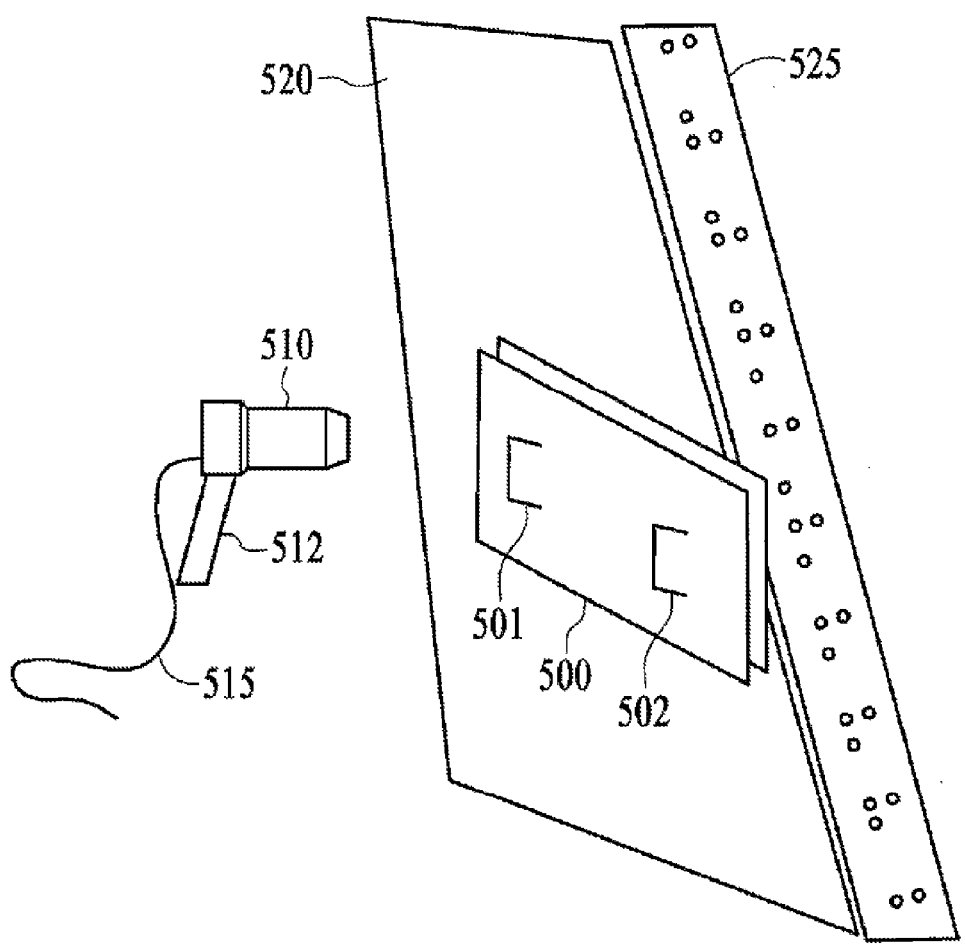
FIG. 5 illustrates a conceptual sketch of a handheld IR inspection system consisting of a handheld camera and manually operated heating mat.

The method and apparatus of the preferred embodiment of the present invention (IRIS) is illustrated in FIG. 4 as it is applied to inspection of the aluminum honeycomb boron composite structures found in the vertical stabilizer of an F-15 jet aircraft like the one shown in FIG. 2. FIG. 5 illustrates an alternative embodiment, a handheld version of the system (i.e., referred to handheld IRIS), which was shown in FIG. 4 and being used in an inspection in FIG. 3. In this case, neither the IR camera nor the conductive heating mat is attached to the frame. The main purpose of the frame is to make it easier to position and orient the camera with respect to the composite surface. This positioning and orientation is now done using photogrammetry methods using the reference fiducials on the IR Ruler, which must be present in the IR images actually used for the NDT inspection. The IR ruler may be larger and more complicated when inspecting larger composite structures. Since the IR camera may be positioned at a greater distance from the composite than would normally be done when using a frame-based system, an IR camera with a higher resolution may be required. The IR camera shown in FIG. 4, which has resolution of 640×480 but only processes and uses the data at a resolution of 320×240, would suffice for the handheld application.

The method and preferred embodiment of the present invention method was motivated by and was implemented for inspection the aluminum honeycomb boron composite on the F-15 vertical stabilizer and most of the descriptions will focus on this application. However, this same system has been demonstrated on many other types of composites and composite structures like the carbon composite F-15 carbon speed brake, the aluminum honeycomb structure with aluminum skins, carbon composites on structural form, boat hulls, car siding, surf boards and thick sections of fiber reinforced plastic (FRP) composites (e.g., wind blades).

The present IR inspection method and apparatuses of the present invention have important advantages over other NDT (e.g., x-ray, ultrasonic/acoustic, and coin tap test) and other thermography methods and apparatuses. Some of these advantages were described above. The performance and operational advantages of the present invention over other thermography methods are based on automation and signal processing. A few of the advantages are:

the entire inspection is automatic and does not have to be performed by a highly skilled technician;

the system is easy to setup and use and requires very little training because the operator only needs to place the heating mat at enough areas of the composite structure to obtain full coverage (note: the computer will point out the coverage and the voids in coverage in real time);

the results of an inspection are completed in real time before the operator completes the inspection;

the results of an inspection can be confirmed from a remote inspection using the real-time processing algorithms before the operator completes the inspection;

decisions about whether or not defects are present are automatically made using powerful noise cancellation signal processing algorithms and do not require visual interpretation of IR images that may be ambiguous to the eye;

when defects are detected, the system automatically determines where it is located in the IR image and on the composite structure being inspected, and how large and how strong the defect is;

the performance of the system in terms of probability of detection ($P_D$) and the probability of false alarm ($P_{FA}$) can be easily estimated because results of an inspection are based on standard algorithms;

an uncooled IR camera can be used, which is significantly lower in the cost and operational use than the more expensive cooled IR cameras; and an effective, safe, and simple-to-use method of uniformly heating the surface of the composite structure using a conductive heating mat.

The performance of the method and the preferred and alternative embodiments has been evaluated several times over a period of several years with nearly identical results using IR inspection measurements obtained on the aluminum honeycomb composite on F-15 vertical stabilizers to estimate the $P_D$ and the $P_{FA}$ for defects as small as 0.25 in. (0.0625 in.$^2$). The results of these evaluations indicates that the method can operated with a $P_D$>99% and a $P_{FA}$<1% using either a pre-determined threshold, or a threshold adaptively determined from the background noise of the IR image being analyzed.

Field measurements on F-15s and on F-15 damaged sections at Robins AFB were made on boron and carbon composites found on the vertical stabilizer and speed brake, respectively. Simple but robust algorithms were validated that can automatically distinguish and identify disbonds, delaminations, fluid ingress, and epoxy buildup in honeycomb composite structures. It can also be used to distinguish whether or not the fluid ingress is significant or not. The spatial coverage and the ability to distinguish and identify between defects offers significant advantages over other NDI methods like acoustic, tap, and x-ray inspection methods. The IRIS algorithm suite also effectively identifies and mitigates false alarms (false defects) and sources of interference from false targets like rivets and seams between materials. The IRIS is not affected by the paint, lettering, or decals on the structure and can be used to confirm the bonding between the original composite and composite patches used for refurbishment. This system improves upon existing IR methods in terms of speed, accuracy, and cost. The system is a fully automatic, real-time system that can be operated with minimal training and experience. Once a defect is detected, a comprehensive post-test processor allows the operator to verify the detection in real time, either in the field or remotely in the office via a web-based connection.

A novel method of conductively heating the composite is used. It is comprised of a very thin silicone heating mat that quickly increases the surface area of the composite several degrees in 10 s, or less, to produce a strong thermal signature due to the defect that is detectable with an uncooled IR camera. A novel method of finding the location and size of each defect on the actual aircraft was also implemented and validated using thermal markers. A single measurement covering an area of 13 in. by 11 in. can be completed within 15 to 60 s using a COTS low-cost, low-resolution uncooled IR camera.

Figure 7:
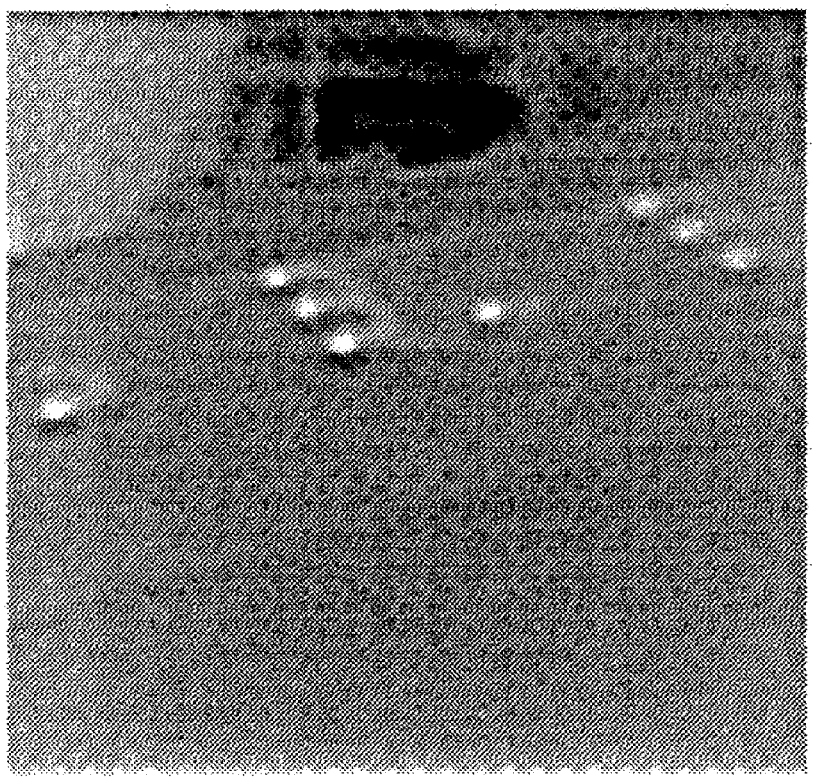
FIG. 7 illustrates the IR Ruler positioned on the vertical stabilizer and the IR image of the IR Ruler recorded during the heating step of a measurement.
Figure 7:
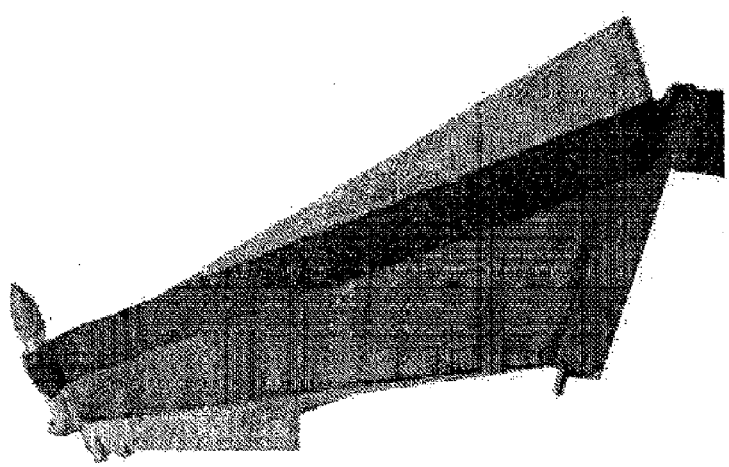
Figure 13:
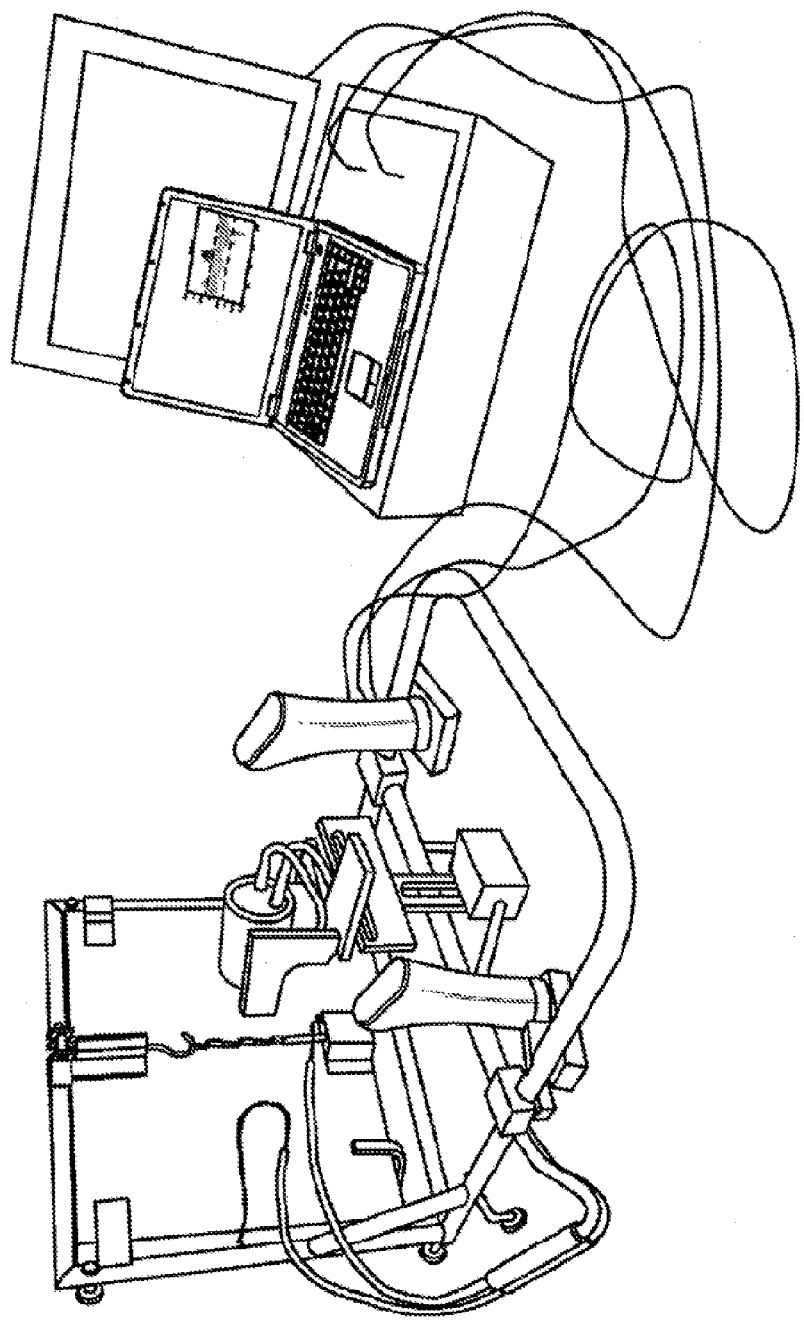
FIG. 13 illustrates the complete IRIS system including the frame with heater and IR camera, control box with notebook computer, and cabling.
Figure 14:
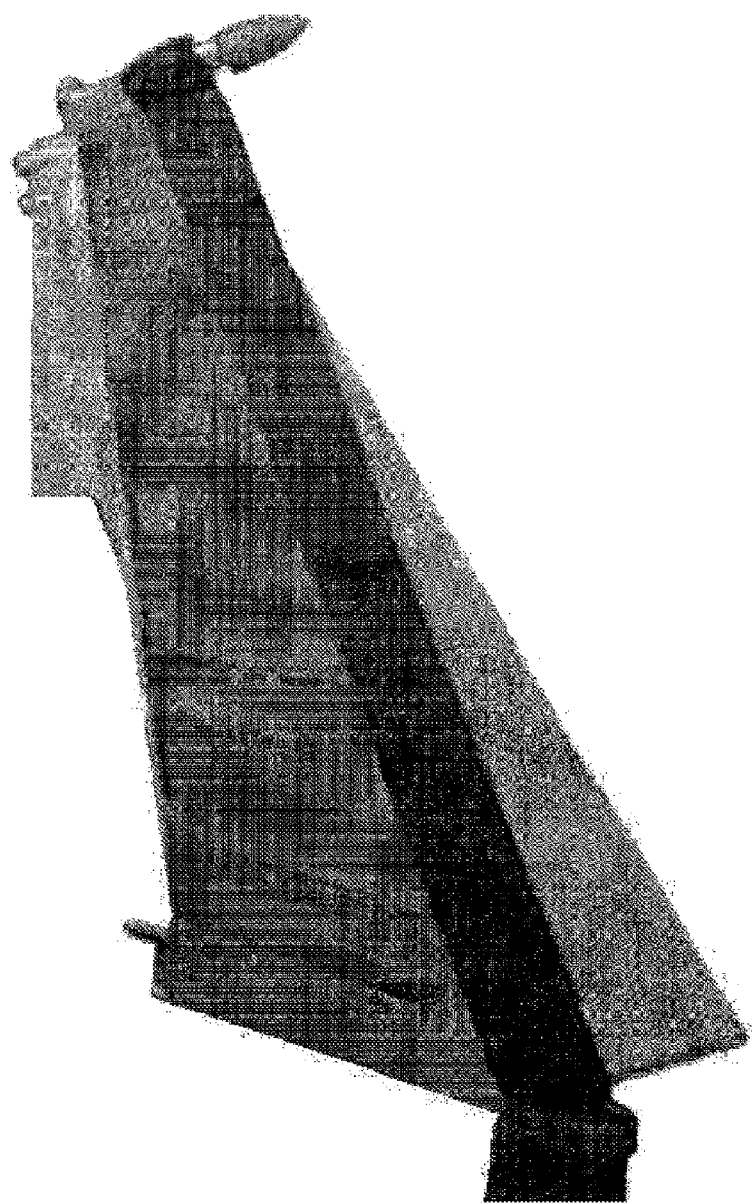
FIG. 14 illustrates an F-15 vertical stabilizer with the IR Ruler placed along the leading edge.

The preferred embodiment of the present invention is illustrated in FIG. 13. The system is comprised of a lightweight frame, a control box which contains the notebook computer, and cabling to connect the two. The IR Ruler, illustrated in FIGS. 7 and 14, is used when location measurements are desired. The lightweight, aluminum frame is comprised of an uncooled micro-bolometer IR camera, a hinged silicone heating mat assembly, a latching mechanism to release the heater, and control grips to allow the technician to operate the equipment. The frame is constructed of aluminum tubing and weighs less than 20 lbs. The electrical aspects of the frame include power to and image data returned from the IR camera, power to the heater, and control of the latch to release the heater. The control grips used for lifting and positioning the frame contain buttons for the operation of the heater and the latch.

The system is typically operated by a two-person team (see FIG. 3), but could be implemented by one person. One person positions the frame and conducts the heating. The second person operates the computer, which is used initiate, stop, and process the data collected during each measurement. The second operator can be present onsite as part of the data collection team, or can be located offsite in a remote location and connected onsite via the internet.

The notebook computer is used to record and analyze the data, present the results, and archive the results for record keeping. The purpose of the frame is to position the IR camera at a known distance and orientation relative to the composite structure and to align the heated area of the composite with the field of view of the camera. In many applications, the frame is not necessary because the camera positioning and orientation can be accomplished using the fiducials on the IR Ruler.

The coverage area of the system is a trade-off between the coverage area for any one measurement and the size of the frame for ease of maneuverability. Two systems were implemented, one with a large frame and a large coverage area using a standard 25 mm lens and one using a smaller frame and a wide-angle lens to maximize the coverage area. In the first system, the coverage area for a single measurement was 20 in. by 15 in. (surface area of 2.1 ft$^2$.) The frame positioned the camera 24 in. away from the composite surface to produce this coverage area. As illustrated in FIG. 4, the frame also positioned the heater to be centered in the field of view of the camera. The overall frame dimensions are 24 in. wide×22 in. high×37 in. deep. The coverage area of the smaller system was 13 in. by 11 in. This was obtained by positioning the camera 17 in. from the composite surface. The overall frame size was reduced to 20 in. wide×21 in. high×24 in. deep.

Figure 15:
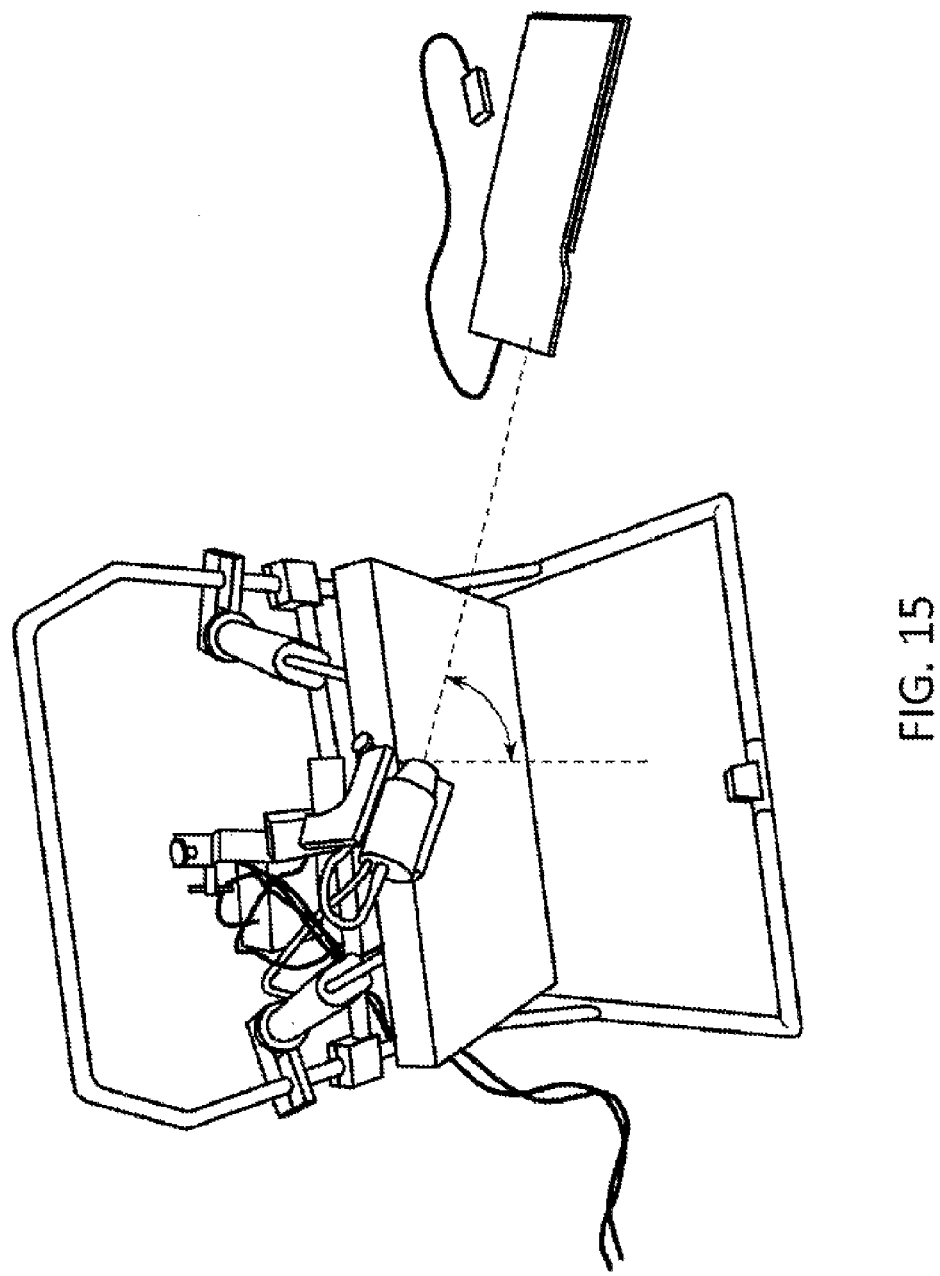
FIG. 15 illustrates the IRIS frame placed in the calibration jig which is used to confirm the placement of the camera and determine the calibration factors for the location algorithms.

The frame was designed to be quickly disassembled and reassembled for shipment and storage. The hinged heating assembly is attached to the frame handles with set pins. The camera is removable and is quickly reattached with thumb screws. The cabling is attached on both ends with circular connectors. A calibration jig, illustrated in FIG. 15, was designed and assembled to ensure the camera was properly oriented and to verify the accuracy of the detection measurement and the location measurement. The calibration is best used when the system is unpacked and assembled for an inspection.

The IRIS is capable of detecting delaminations, disbonds, and fluid ingress in the composite/honeycomb structure of an F-15 vertical stabilizer as small as 0.5 in$^2$ (i.e., approximately 16 pixels using a 320 by 240 array). The system is fully automated and outputs the location and size of any defect detected. Each defect is identified and classified in real-time. The NDI technician is not required to interpret IR images to determine the condition of the aircraft component under inspection. A suite of processing algorithms that incorporate a noise compensation filter and a threshold comprised of a minimum intensity and minimum cluster of pixels exceeding this intensity level are utilized to detect and distinguish damage to the structure.

An inspection is made up of multiple measurements covering the composite surface under investigation. Each measurement is registered to a known point on the surface creating an overall mosaic of the inspected area using an IR Ruler. Damage or flaws that are detected are registered back to the known point and are plotted on the mosaic. This provides a visual representation of the inspection results on the aircraft structure inspected or being inspected.

Hardware.

Figure 6:
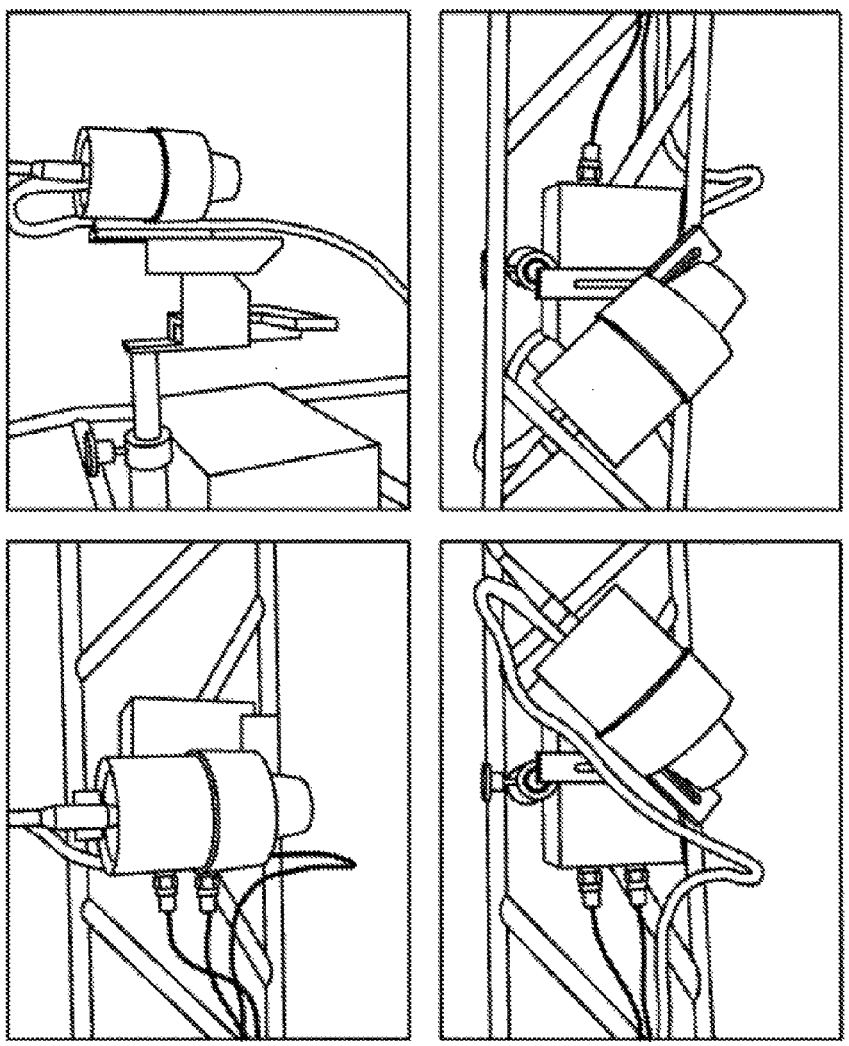
FIG. 6 illustrates the IR camera mount which allows the IR camera to be rotated to the correct position for viewing the IR Ruler. Stops designed in the mount set the rotation without the operator having to measure or align the rotation.

The IR camera selected for this project was the DRS M6000 with 12 bit camera link data format. The image output of the camera was read directly into the IRIS software. The image size was 640×480 pixels (producing a pixel resolution of 0.03125 in/pixel). This camera was selected instead of a less expensive one with a resolution of only 320 by 240 in case there was a need to average data spatially to obtain sensitivity. It was determined, a less expensive camera would suffice. All of the measurements made with the DRS M6000 camera were downsampled to 320×240 for processing (producing a resolution of 0.0625 in./pixel). The micro-bolometer camera does not require external cooling or temperature stabilization, which makes it good choice for a portable system. The camera is mounted at the required height and distance from the composite surface to produce a focused IR image of the correct pixel resolution. As illustrated in FIG. 6, the camera mount was designed to pivot to the right and left to collect images of the IR Ruler during the heating process. The pivot locations were predefined and were set with ball detents. The operator rotates the camera until the ball detent is reached and the camera snaps into place. The operator does not have to measure or align marks to set the camera position.

As illustrated in FIG. 4, the hinged heating mat assembly and latching mechanism work together to hold the heater firmly against the composite surface during heating and to quickly release the heater and remove it from the camera field of view. The silicone mat heater has a capacity of 2.5 W/in.$^2$ and raises the composite surface about 5° C. (10° F.) over the 10 second heating period. The heater is attached to a rigid backing with a 1.5 in. thick foam core between the two. The foam allows the heater to flex with the contour of the composite surface to achieve consistent heating. The heating assembly is held firmly against the composite surface until the latch is released by the operator via a button on one of the control grips. Gravity is used to drop the heater away from the composite surface and out of the view of the camera. Both the heater and the latch are operated by buttons on the control grips. The heater is only on when the button is pressed by the operator. As soon as the button is released the heater is turned off This safety feature prevents the heater from being left on when the frame is not in use.

The frame is lifted and placed in position on the composite surface by ergonomically designed control grips located near the center of the frame to make the system lighter and easier to hold. Each control grips contains a button which powers the heater in the right hand and activates the latch in the left hand. A leverage bar, which fits into the operator's mid-section, is positioned behind the control grips to aid in lifting and holding the frame in place while acquiring the IR images.

A control box provides power to the frame through a set of power and instrumentation cables. The control box is powered with a single 120 VAC 15Amp circuit and provides 120 VAC to operate the heater and 12 VDC to operate the camera and latch. IR Image data is returned to the control box via a camera link cable. The control box houses the notebook computer, which operates the system. Internal fuses protect the operators and equipment from electrical hazards.

As illustrated in FIGS. 7 and 14, an IR Ruler is installed along the leading edge of the composite surface when the location and registration algorithms are to be used. (The IR Ruler can be placed on either edge or any location on the aircraft structure to be inspected.) The IR Ruler consists of an array of fiducials (low-power resistors) in a very specific pattern sandwiched between a felt upper surface and a rubber backing. The IR camera is rotated toward the IR Ruler during the heating portion of the measurement (so that the fiducials are in the field of view of the camera) and records IR images of the IR Ruler for the first 10 seconds while the system is heating the composite surface. The camera is rotated back to center prior to releasing the heater. The location algorithm detects the fiducials, determines the pattern, interprets the pattern in terms of distance, locates the IR image, and places the measurement at the correct location on the composite surface. The IR Ruler is powered by 120 VAC supplied from the control box or a small battery pack. The placement of the IR Ruler on the stabilizer must be consistent from stabilizer to stabilizer to obtain accurate location measurements. The IR Ruler for the F-15 stabilizer is designed to align with the leading edge and the top edge of the composite surface. The IR Ruler is notched and marked at the top for precise placement. FIG. 7 shows the IR Ruler in position for an inspection.

A calibration of the IRIS is performed when the system is unpacked and assembled for an inspection. The positioning of the camera is critical to the successful operation of the location and sizing algorithms. The calibration jig provides the required calibration settings for the location algorithms and provides a check that the camera is in the proper position and directed normal to the composite surface with no tilt or rotation. FIG. 6 shows the frame placed in the calibration jig with the camera rotated left for the location calibration.

Description of Detection Algorithms.

Sample Measurement and Inspection Results of IRIS The automation and high performance of the method and apparatuses of the present invention are achieved because of the use of robust signal processing algorithms. Unlike many NDE methodologies, an NDT technician is not required to continuously review and make decisions about the presence or absence of defects in the image during the inspection. The software implements a simple, but highly robust adaptive background noise compensation/removal algorithm that produced defect signals that were 20 to 25 dB greater than the background noise.

The algorithm is used to detect delaminations, disbonds, and fluid ingress within the aircraft structure and differentiate between the types of detections. Each flaw type has a unique thermal signature that allows the software algorithms to determine the type of flaw. All three defects produce a signal with the same heating requirements, which means that a single measurement with 10 seconds of heating may be used to look for all three flaw types. The difference in thermal signatures is when they appear (how many seconds after heating), how large the intensity is (how high a peak signal), and whether or not the signal is positive or negative (warmer or cooler than the background temperature.)

Figure 1:
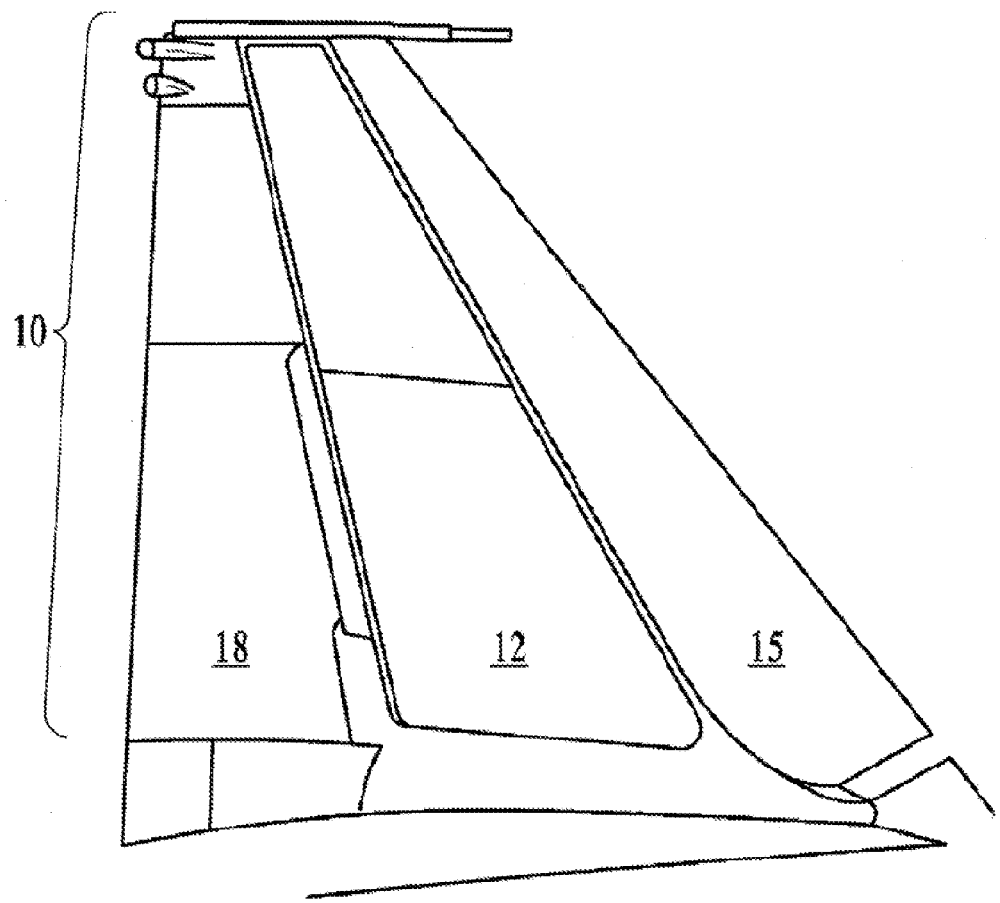
FIG. 1 illustrates the F-15 vertical stabilizer showing the boron composite area and the leading and trailing edge.

Measurements are conducted with the preferred embodiment by heating the composite surface with a mat heater for approximately 10 seconds and recording IR images of the composite surface for another 50 s seconds during cooling of the composite surface after the heater has been removed. As illustrated in FIG. 1, the heater and camera are mounted on a lightweight, aluminum frame, which positions the heater to heat the composite and positions the camera to collect the IR data. Specific frames of data are selected for analysis to identify the type of defect being detected.

Figure 9:
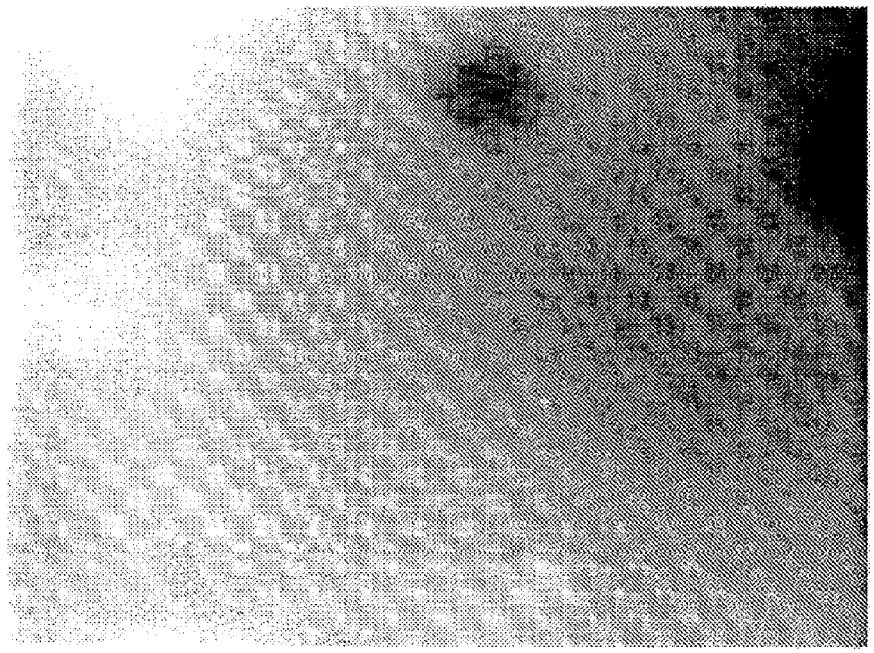
FIG. 9 illustrates a raw IR image collected 30 seconds after removing the heater showing a fluid ingress (darker area) and a disbond (lighter area).

FIG. 9 shows a single raw IR image used for detecting a disbond and fluid ingress taken 30 seconds after removing the heater. A disbond is visible in the raw IR image as a strong "positive" peak in the noise compensated image (a white, or warmer, spot on the IR image), because it has a significantly higher intensity than other regions of the composite. In the aluminum honeycomb boron composite, the disbond signal begins to appear in the IR images about 10 seconds after removing the heater and reaches a peak intensity at about 30 seconds. The disbond signal then decays for the following 60 seconds. A frame 30 seconds after removing the heater is used for detecting disbonds. The disbond in FIG. 9 is located slightly to the right of center at the bottom of the image. In contrast to disbonds (and delaminations), fluid ingress produces a "negative" peak (a black, or cooler, spot on the IR image) in the noise compensated image. The timing of the fluid ingress signal is similar to that of the disbond. The fluid ingress signal begins to appear in the IR images about 10 seconds removing the heater, reaches a peak intensity (in the negative direction) at about 30 seconds, then decays for the following 60 seconds. The same frame used for detecting disbonds is used for detecting fluid ingress (30 seconds after removing the heater.) The other white IR intensities observed along the left half of the image and the other black regions along the right half of the image are background noise, which may be confused for disbonds or delamination or mask the presence of these types of defects.

As delamination, not shown in FIG. 9, is also detected as a strong "positive" peak in the noise compensated image though the peak produced by a delamination is 3 to 4 times larger than the peak for a disbond. Additionally, the delamination signal appears immediately after removing heater, begins to decay at about 6 seconds, and has decayed below the threshold after 15 seconds. A frame 3 seconds after removing the heater was selected used for detecting del aminations.

Figure 10:
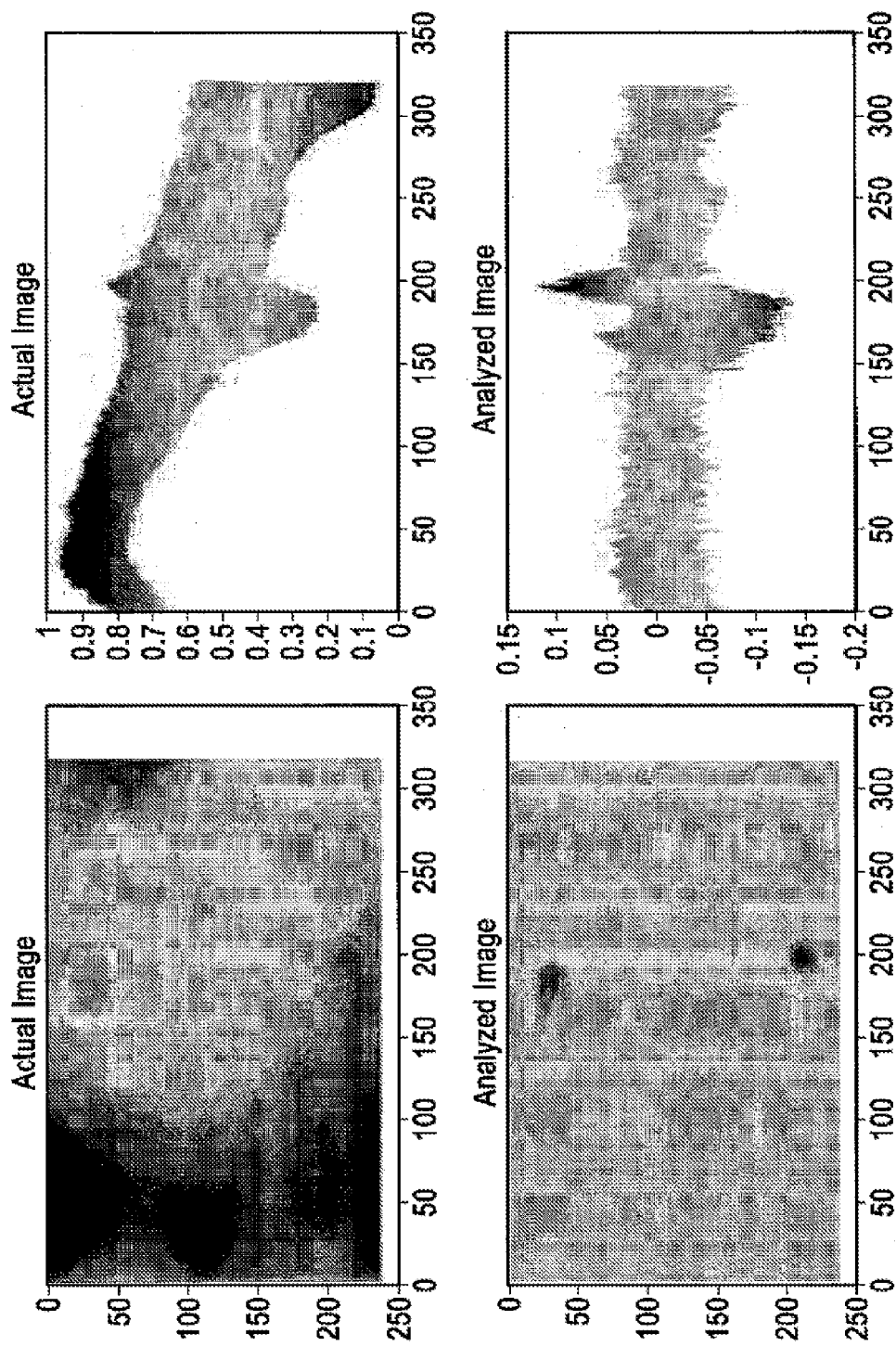
FIG. 10 illustrates the results of the noise cancelling algorithms applied to a raw IR image.

The IRIS noise compensating algorithms are able to automatically detect the presence and identify the disbond and fluid ingress signals in the IR image shown in FIG. 9 and without interpretation by a trained NDT technician. The noise compensating algorithms are able to eliminate background observed along the left and right halves of the image due to inconsistencies in the heating and the curvature and roughness in the composite surface. FIG. 10 illustrates the performance of the algorithm. The upper two color images are of the raw IR image shown as a two-dimensional "horizontal" view looking at the surface of the composite (left) and as two-dimensional "vertical" view looking at the side of the composite (right) plotted using a black and white scale with white being warmer and black being cooler. As illustrated by the lighter regions, the left side of the surface of the image (i.e., composite) is clearly warmer than the right side. Even though the heating of the surface shows a gradient across the composite surface, the signal from the disbond and fluid ingress are visible as a warmer (white) upward "bump or peak" for the disbond and a cooler (black) downward "bump or peak" for the fluid ingress. The two images on the bottom of FIG. 10 are of the same IR image, but after applying the noise compensating algorithms. The background heating gradient has been removed, and the disbond and fluid ingress signals are much more prominent in the images, exhibiting a very large signal to noise ratio (SNR) of over 20 dB. The areas of damage can be detected by applying a simple threshold across the entire processed image. While the IR signals produced by both the disbond and the fluid ingress are very strong, the application of a simple threshold in the raw IR image would miss the defects and declare background noise as defects. The inventor's analysis of the noise cancelled IR image indicates that the background noise is Gaussian white noise (i.e., normally distributed random noise).

The performance of the preferred embodiment has been evaluated using IR inspection measurements on the F-15 to estimate the probability of detection ($P_D$) and the probability of false alarm ($P_{FA}$) for defects as small as 0.25 in. (0.0625 in.$^2$). The IRIS can be operated to insure a $P_{FA}$>99% and a $P_{FA}$<1% using either a pre-test-determined threshold or adaptively selecting a threshold based on the background noise of the IR image being analyzed. This performance is obtained analyzing a single IR image and does not require averaging multiple images. Thus, any movement of the frame during data collection will not significantly impact the analysis. Since the noise compensated background is normally distributed (i.e., Gaussian) white noise and the defect signal is additive with the background noise, the performance can be estimated for different thresholds, with or without averaging, and for signals of different intensities. The signal-to-noise ratio (SNR) typically ranges from 15 to 25 dB for the defects of interest.

Background noise can come from a variety of sources, but mainly it is due to uneven heating, uneven application of the epoxy bonding the underside of the composite to the aluminum honeycomb structure, and/or debris or surface defects on the composite. The bottom right image in FIG. 4 shows the noise compensated image from a side view. The presence and location of the defect signals in the noise compensated image are easy to identify, because their amplitude peaks are well above the background IR intensities associated with the undamaged portions of the composite.

The threshold is applied to the noise compensated image to eliminate the areas of background. The exceedance level is applied when performing a cluster analysis to determine size and location. Each pixel exceeding the threshold is given a value of 1, all other pixels a value to 0. A cluster is a group of pixels with a specified value that are adjacent to each other, including diagonally. The number of pixels in the cluster must be larger than the exceedance limit to be detected. This limits the minimum defect size. The exceedance limit is also used in removing potential false alarms by eliminating very small groups of pixels that exceed the threshold. These very small groups (<5 pixels) are typically debris on the composite surface or small areas of exposed metal along the leading or trailing edge of the stabilizer.

Figure 11:
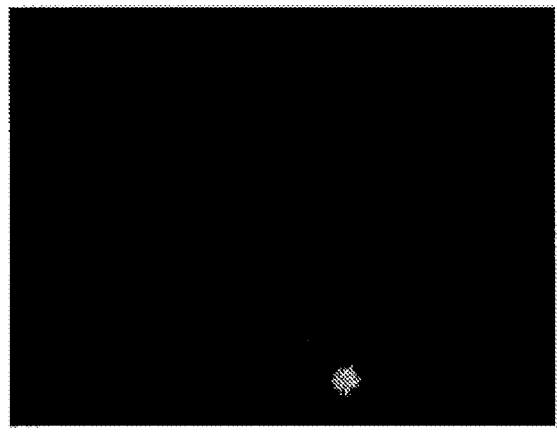
FIG. 11 illustrates the cluster maps of the fluid ingress and disbond detected with the IRIS system.
Figure 11:
Figure 12:
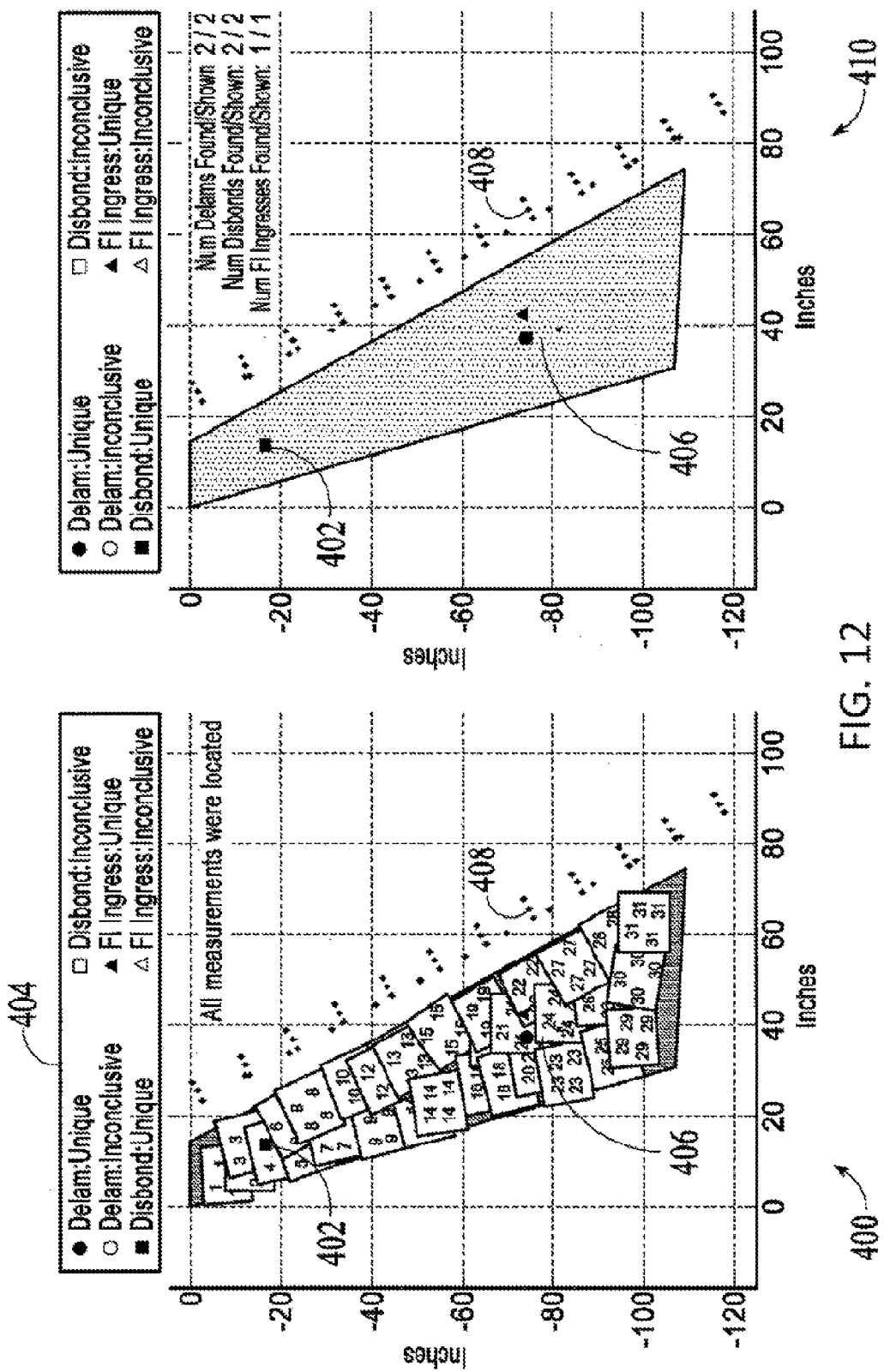
FIG. 12 illustrates the coverage map with measurement numbers and the flaw map that the IRIS creates at the end of an inspection.

FIG. 11 shows the cluster analysis for the disbond and fluid ingress flaws from FIG. 10. The cluster analysis determines the size of the detection in pixels which is converted to an area based on the camera's parameters and location. It also determines the centroid of the detection from the upper left corner of the image. The centroid is used in the location analysis when conducting a complete inspection comprised of multiple measurements. In the automated system, each image is referenced to an actual point on the aircraft. Therefore, any detections within an image are also referenced to an actual point on the aircraft. The cluster analysis is dependent on the detection threshold used and the noise compensation filter size. For an accurate size determination and an accurate count of the number of defects, the area of the cluster must be no larger than 30% to 50% of the area of the noise compensation filter.

Description of False Target Mitigation.

The analysis algorithms effectively identify and mitigate false alarms (i.e., peaks that exceed the threshold on the composite surface that are not real) that might be produced by uneven heating, and sources of interference (or actual targets that are real and can be differentiated from defect signals by visual inspection) that may be caused by edge boundaries between composite and metal surfaces, and debris or scratches on the composite surface. Initial analysis of the IR image will detect any feature that exceeds the background IR noise. Methods and routines have been implemented to detect features that do not behave with an IR signature similar to the known behaviors of delaminations, disbonds, and fluid ingress.

Small pieces of debris such as specks of dirt on surface or small areas of exposed metal along the edges of the composite may produce detections that are very small in area but with an intensity that exceeds the threshold. The exposed metal areas tend to be positive or warmer than the background. Specks of dirt, on the other hand, tend to be negative because they prevent good contact between the heater and the composite surface. These types of detections are very small, typically less than 10 pixels or 0.05 in$^2$, and these detections are removed by setting an exceedance level which eliminates these tiny detections.

Edge effects occur when a measurement extends off the composite surface onto the leading or trailing edge of the vertical stabilizer. Signals are produced at this junction due to how the different materials respond to the heating. In the case of long, straight edges in the IR image, the location of the measurement on the vertical stabilizer is used to disqualify these detections. The location of the measurement on the composite surface is determined using the IR Ruler. By placing the measurement in position on the composite surface, it is known whether the image extends past the edge of the composite and the location of the edge is known. Any detections that fall along the edge are then disqualified.

Figure 8:
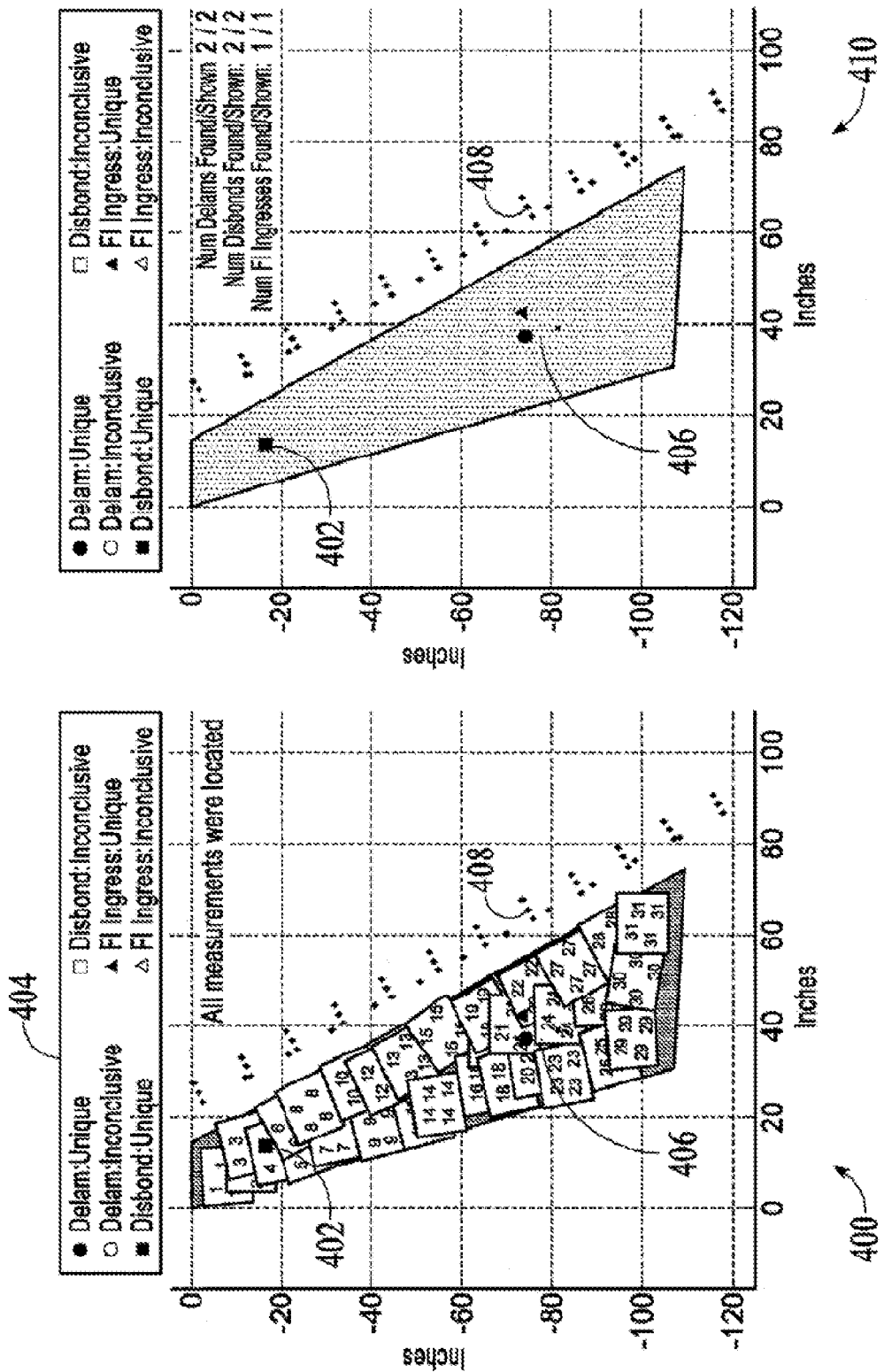
FIG. 8 illustrates the coverage map with measurement numbers and the flaw map that the IRIS creates at the end of an inspection.

An IR Ruler, which consists of fiducials or markers in a specific pattern that are visible to the IR camera, is placed along the leading edge of the vertical stabilizer. During the heating portion of the measurement, the IR camera is rotated to the side to collect images of the IR Ruler. The location algorithms detect the fiducial pattern and determine where the measurement is being conducted on the composite surface based on the pattern. An overall coverage map is generated from consecutive measurements showing which parts of the vertical stabilizer have been inspected and the type and location of any damage detected during the inspection. FIG. 8 shows the flaw map and coverage map from a complete inspection of an F-15 stabilizer. Thirty one measurements were used to cover the composite surface. Multiple defects were detected and are shown on the flaw map color coded for the type of detected.

Software.

The smart-sensor software is a key component of the inspection system and utilizes a powerful set of signal processing algorithms and automatically analyzes the IR image in real time. It automates the inspection process by producing a Pass/Fail indication following each measurement and an overall coverage map showing the regions of the surface that have been inspected with any flaws that were detected. The processing is completely automated without requiring human interpretation of the IR images. The IRIS software records IR images directly from the camera, instructs the operators conducting the measurements, performs the analysis for each type of flaw, displays the results in an easy-to-interpret manner, and archives the data and results for record keeping. The software operates on a standard notebook computer running a Windows operating system. Matlab® by The Mathworks, Inc. (Matlab is a registered trademark of The Mathworks, Inc., Natick, Mass.) was used to implement the IRIS software. The system requires the Matlab Image Acquisition Toolbox for operation of the camera and the Image Processing Toolbox for the processing of the IR images.

An overview of the software is summarized below.

1. A measurement is initiated by a single button on a computer and run to completion including data collection, analysis, and data archiving.

2. The software steps the operators through the process of preparing the frame, heating the surface, and releasing the heater.

3. The software determines the location of the measurement on the vertical stabilizer.

4. The software automatically collects the data and performs the analysis.

a. Starts and stops IR image collection.
   b. Determines when the heater was removed.
   c. Determines the location of the measurement and any detections by selecting the proper frame for analysis, detecting the fiducials, recognizing the fiducial pattern, and calculating the location.
   d. Selects the proper frames for analysis of each type of defect.
   e. Apply filters, thresholds, and exceedances for detecting each type of damage.
   f. Applies false target mitigation algorithms to eliminate detections that are not delaminations, disbonds, or fluid ingress. These detections may be fasteners, the edge between the composite surface and leading or trailing edge, or dirt.
   g. Collects and tallies each detection, including the type of detection, its location, and its size.
   h. Presents the results of the overall inspection in a concise, easy-to-interpret report.
   i. Archives the inspection data for record keeping.

The process of conducting an automatic inspection is specified and controlled by a set of operating parameters. The system is optimized for the aluminum honeycomb composite structure on the F-15 vertical stabilizer, but the values (like the detection threshold) may be adjusted for inspection of other composites and honeycomb composite structure. The operating parameters are set in the Inspection Settings screen available from the Configure drop down menu from the IRIS main screen. The listing of operating parameters is saved in the master inspection folder when an inspection is initiated.

A unique and beneficial aspect of the IRIS software package is a Post-Test Analysis module, which allows complete freedom in applying the analysis algorithms in a manual mode. The post-test analysis module contains all the detection routines used in the automatic code, but allows the user to fine tune the analysis for a more detailed understanding of the results. The module may be used to validate the results of the automated test or re-examine inconclusive detections. It also allows the processing of images other than those recorded on a vertical stabilizer. If a measurement is conducted on an airbrake or a rudder, this module lets the analysis parameters be tuned to the specific structure being inspected.

A summary report is generated when an inspection is complete. The summary report contains information on the component inspected, a list of detected flaws, the coverage map showing the regions inspected, and a flaw map showing the type and location of the detected flaws on the structure inspected. The summary report provides a concise representation of the results for record keeping and official documentation. Additionally, the IR image files and the individual measurement results are written to the computer hard drive for record keeping. These files may be reviewed for a more detailed analysis or retained for comparison to future inspections on the component.

Operational Sequence.

An inspection is a set of multiple measurements conducted over the composite surface. A measurement is completed in a little over one minute if no defects are detected and about two minutes if a defect is suspected. An inspection of one side of a vertical stabilizer requires 34 measurements and can be typically be completed in less than an hour. The system is operated by a two-person team. One person positions the frame and conducts the heating. The second person controls the computer for data collection and processing.

The steps for performing an inspection include the setup and calibration of the frame and equipment, starting an inspection, and conducting the individual measurements. The software provides screen instructions on the monitor to the operators while conducting the inspection.

(1) Assemble the Equipment.

The frame is manufactured in two pieces that are quickly assembled for operation. The handle portion of the frame attaches to the heating assembly with two set pins. Two cables for the latch and heater are connected between the handle and the heating assembly. The cables are keyed to only attach in the correct configuration. The IR camera latches into the rotating mount with two set pins and ball detents snap the camera in to the correct orientation.

A Cameralink PCMCIA card is inserted into the notebook computer and the computer mounted on the control box. Three cable connections are required. A Cameralink cable attaches between the camera and the Cameralink card at the computer. Two power cables are used, one to supply 120 VAC to the heater and one to supply 12 VDC to the controls on the frame. Each connects with keyed circular connectors.

(2) Start IRIS Software (IRISGUI).

The IRIS software (IRISGUI) is started with an icon on the desktop. The IR camera is initiated during startup and the operator may select the Preview Camera button at any time to view the camera output. The Cameralink card must be installed and power applied to the camera when starting the software. The operator is alerted if there is an error initializing the camera. The inspection parameters for the automatic inspection are initialized at startup. They may be viewed or modified by selecting Inspection Settings from the Configure Menu.

(3) Perform Calibration.

The calibration jig is used to confirm the camera is correctly installed and to determine the calibration factors for the location algorithms. The frame is placed in the calibration jig in foot holes, which align the frame with the test fiducials. Then, a sample measurement in the calibration jig is recorded by starting a preliminary inspection. The camera is positioned to view the Camera Position Fiducials for a few seconds and then rotated to view the Location Test Fiducials. The Camera Position fiducials are what the camera views when in the centered position. It confirms the "straightness" and distance of the camera to the composite surface. The Location Test Fiducials perform a measurement of the rotation of the camera and provide the location module calibration factors.

The Calibration Module of the IRIS software compares the fiducial locations in the IR images with the known locations on the jig. Camera alignment is confirmed by comparing the alignment of the measured fiducials against the known alignment of the fiducials.

The calibration module calculates the calibration factors for the location routines by an iterative process that will align the measured fiducial locations with the known fiducial locations. The location calibration factors are then entered in the Inspection Settings screen. The bottom image of FIG. 7 shows the aligned location test fiducials.

(4) Install IR Ruler.

The IR Ruler is placed along the leading edge of the composite on the vertical stabilizer of the F-15 aircraft with double-stick tape. The top of the IR Ruler is marked to align with the top of the composite surface. The IR Ruler is powered by the control box or may run from a 9-volt battery pack.

(5) Start Inspection.

An inspection is started by clicking the Start Inspection button on the main screen. The Inspection Setup window appears, as illustrated in FIG. 16. The operator enters the information pertaining to this inspection including the site, facility, type of aircraft, aircraft component to be inspected and its serial number, and operators. The operator indicates whether the location module is being used, and, if so, which stabilizer is being inspected. A comment may also be entered. A unique inspection label is generated based on the date and time. The IR images and results are saved under this label. This information is written to the hard drive of the computer with the inspection settings. It is also included in the summary report.

Figure 17:
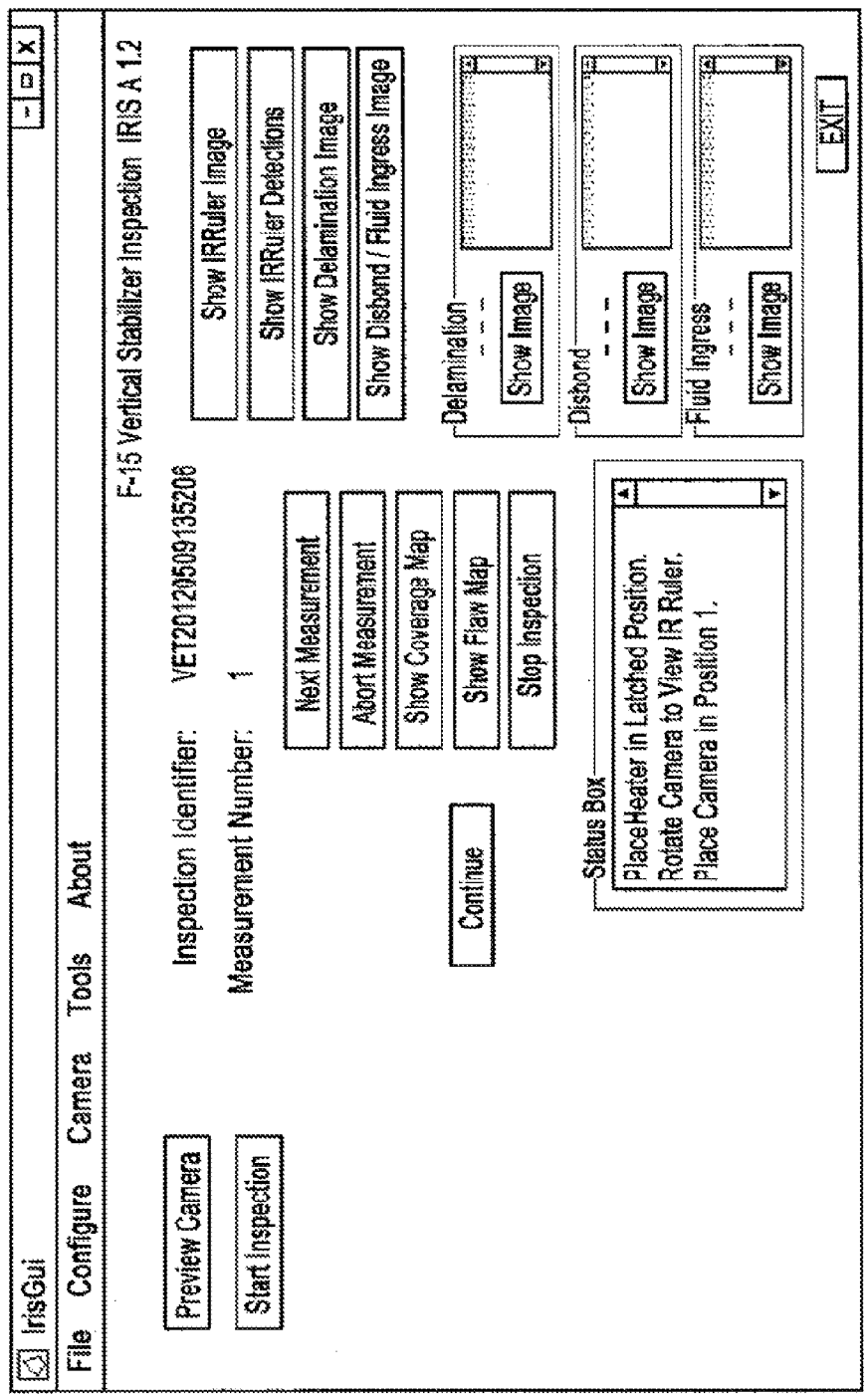
FIG. 17 illustrates the Main Screen of the IRIS graphical user interface.

The main screen (FIG. 17) of the IRIS software controls the flow of the inspection. The status box instructs the operators and shows the current step of the measurement. The group of buttons in the center of the screen step the system through consecutive measurements, abort a measurement, or end an inspection.

(6) Prepare Frame for Measurement and Position on Composite Surface.

The frame is prepared for the measurement by latching the heater in the heating position and rotating the camera to view the IR Ruler. This is done prior to each consecutive measurement. The operator places the frame on the composite surface at the location for the measurement. The operator starts the heater by pressing and holding the button on the right control grip.

(7) Start Camera.

The operator at the computer starts recording IR images. The IRIS software will record IR images at a rate of one per second for 65 seconds. (These parameters are set in the Inspection Settings Screen, and are optimized for the F-15 vertical stabilizer.) The IR Images are displayed on the screen during data collection.

(8) Heat Composite and Release Heater.

While holding the frame, the operator firmly presses the heater on the frame to the composite surface for 10 seconds, and then manually rotates the camera back to the center position to view the composite surface. The heater is released by activating the latch with a push button on the left control grip, and the heater falls out of the view of the IR camera. The operator releases the heater button on the right control grip to turn off the heater. The frame is then held in place for the remaining data collection time. The software will indicate on the screen and issue a beep when data collection is complete. The operator may then remove the frame from the composite surface.

(9) IRIS Software Records IR Data and Performs Analysis.

At this point, the IRIS software performs the remaining steps of the measurement with no input from the operator. The recorded IR images are saved to the hard drive of the computer in the measurement folder. The status box lists the current analysis being conducted. The location module will determine the location on the composite and register the image based on the IR Ruler measurement. The analysis routines and false alarm mitigation routines are applied for each flaw type.

Figure 18:
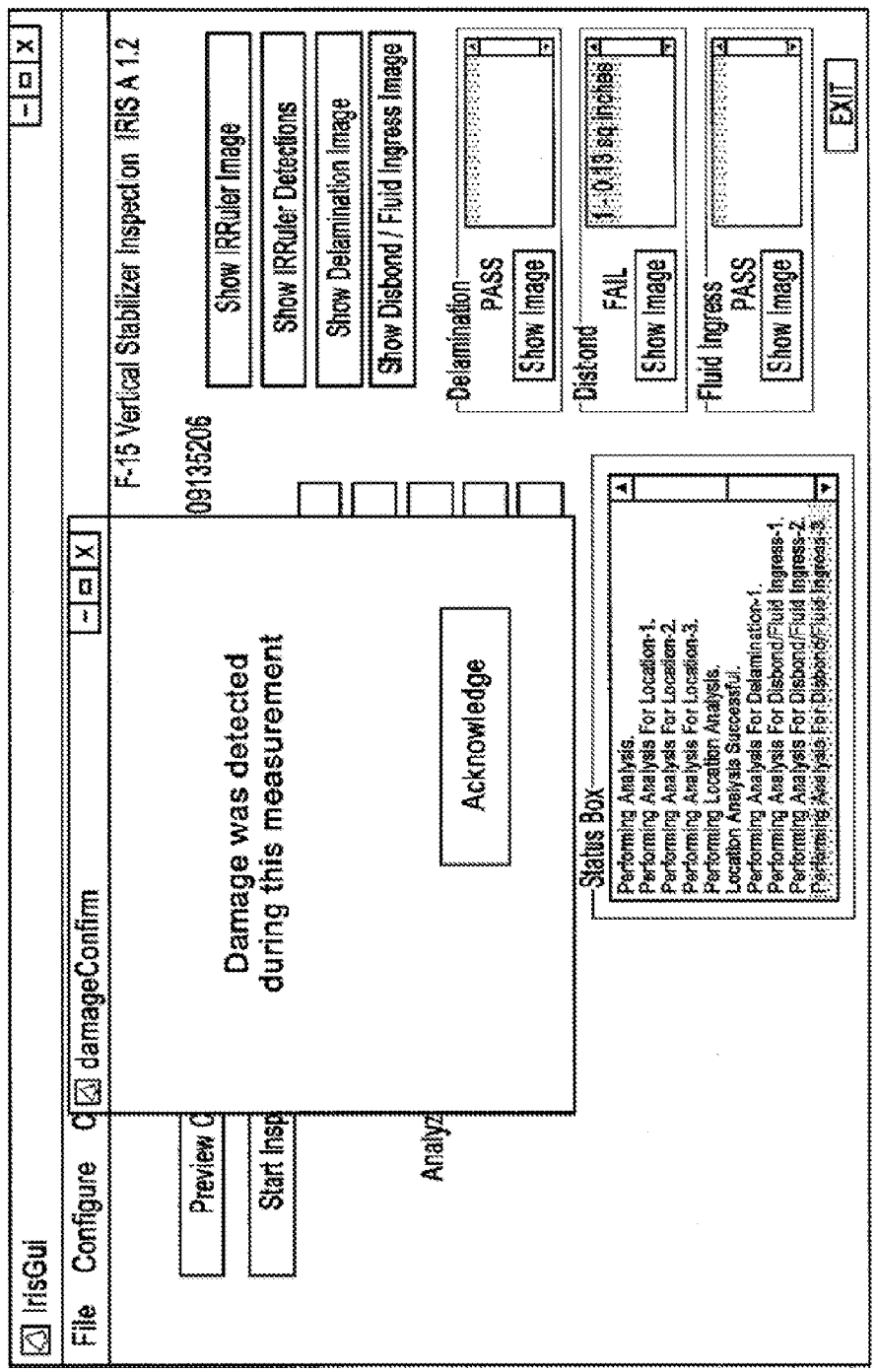
FIG. 18 illustrates the Main Screen of the IRIS graphical user interface while conducting an inspection.
Figure 19:
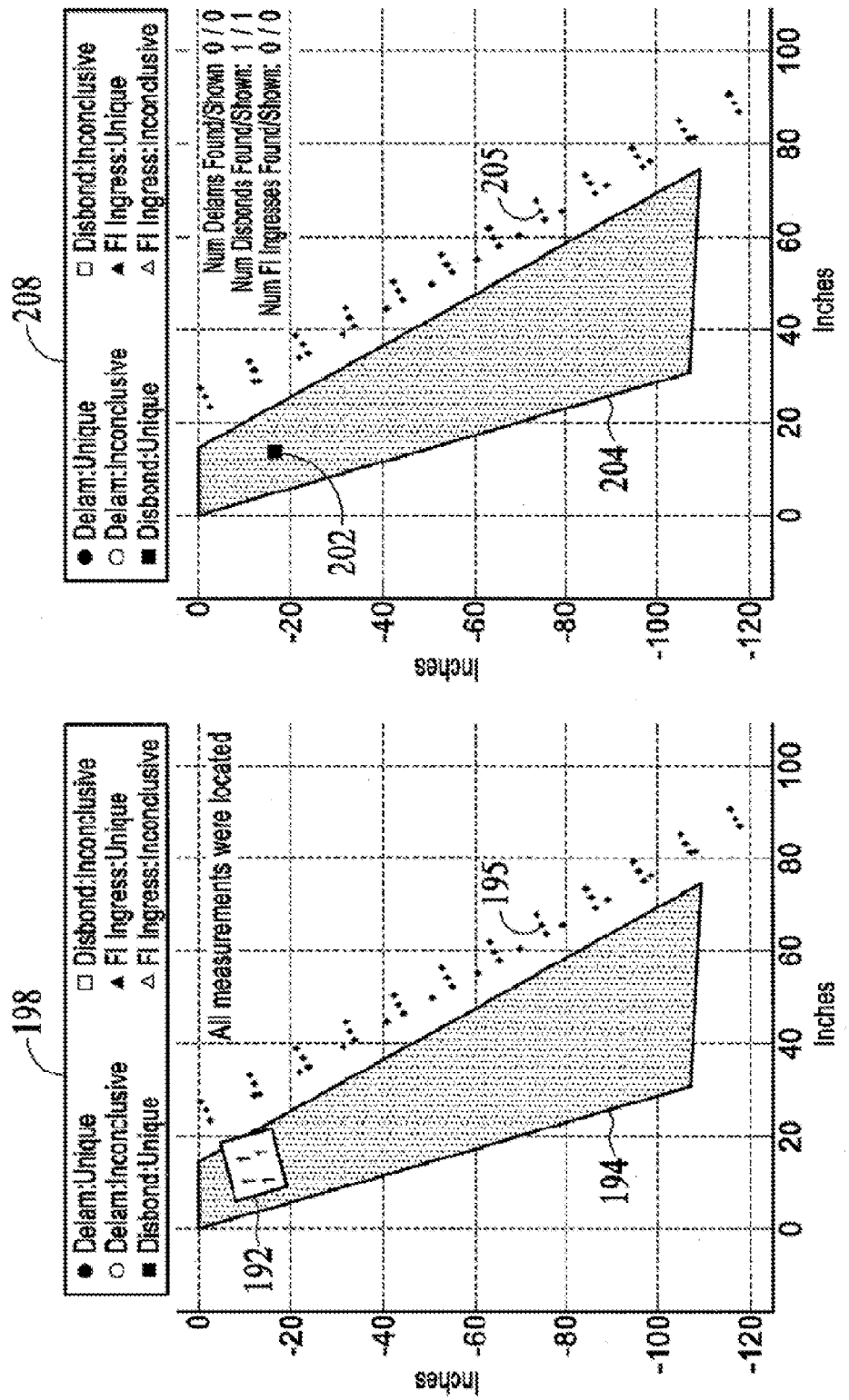
FIG. 19 illustrates the coverage map for only one test (left). The display on the right shows the type and location of the defects. The IR ruler is shown in both displays.

The operator is alerted if any flaws are detected and must acknowledge any detections before continuing with the inspection. When the measurement is complete, the results are displayed on the main screen. FIG. 18 shows the main screen with the results of a measurement. The operator may view the results of the individual measurement by selecting the Show Image button below the PASS/FAIL indictor for each flaw type. The operator may also view the IR image analyzed by selecting one of the four buttons above the results. Any detections in the individual measurement are registered back to a known point on the stabilizer and an overall coverage map is generated (see FIG. 19).

(10) Perform Next Measurement or End Inspection.

The operator initiates the next measurement by selecting the Next Measurement control button. Steps 6 through 9 are repeated until the inspection is complete. The IR images and the individual results from each measurement are saved to the computer hard drive following each measurement. When the inspection is complete, the inspection information, the overall list of detections, the coverage map, and the flaw map are written to a summary report.

Software Modules.

Several additional software modules were implemented in Phase II to create a fully automated inspection system. These modules included the Location Module which determines where on the composite surface a measurement is conducted using an IR Ruler and the software is comprised of four basic modules: (1) the Overall Program Flow Module integrated the multiple measurements that make up an inspection; (2) the Location Module was used to locate the IR camera, the IR image coverage area, and defects with respect to a physical location on the composite being inspected; (3) the Report Generator and Archiving Module to produce a concise summery report of the inspection and archive the inspection data; and (4) A Manual Post-Analysis Module, which allows a more detailed analysis of the data giving the user the ability to change filters and threshold values.

Report Generator and Archiving Module.

A concise summary report is generated for each inspection conducted. The summary report may be used to compare previous inspections of the same stabilizer over the life of the aircraft. The summary report includes a table listing of any detected damage and includes the type, location, and size of the flaw, and the flaw and coverage maps. Compiling the table of flaws includes removing duplicate flaws that could occur from more than one measurement at the flaw location and flagging any detections that may be inconclusive.

The ability to identify the same flaw in more than one image is important to avoid misinterpretation of the results. Consecutive measurements may overlap during an inspection as can be seen in the coverage map. An additional detection routine is applied to flaws detected in overlapping regions. A flaw detected in an overlapping region must appear in each measurement to be considered an actual detection. In this case, the flaw is considered a single flaw and any duplicate flaws are removed. If the case comes up that a flaw is not detected in all the measurements of an overlapping area, the flaw is marked as inconclusive, which alerts the operator to review this area.

A file structure was implemented to archive the data and results from the individual measurements of an inspection. Archived data may be further analyzed using the manual Post-Test Analysis Module. A unique inspection label is generated at the start of the inspection. This label is generated automatically to prevent data from previous inspections from being over written or mislabeled. The label is constructed from the site identifier entered by the user and the data and time of the inspection. A master folder is created on the computer hard drive using this label. The general inspection information, a listing of analysis settings, and the summary report are written to files in the master folder. A folder for each individual measurement is created within the master folder. The IR images, flaw detections, image corner locations, and intermediate processing data are written to each individual measurement folder.

Overall Program Flow.

An overview flow chart of the software, which is shown in FIG. 20 through FIG. 25, summarizes the software modules and how they are integrated. The flowchart integrates the process flow with measurement operations; thus, many of the boxes contain only descriptive information.

The process of conducting an automatic inspection is specified in a configuration file and is controlled by a set of operating parameters. The operating parameters control the many aspects of the system. These parameters include camera settings, which define the field-of-view of the camera and distance from the composite. These values are critical in the location algorithms and the sizing of the defects. The individual IR image frame selection, noise cancellation filters, thresholds, and exceedance levels are preset for each type of detection. The system is optimized for the aluminum honeycomb boron composite comprising the vertical stabilizer on the F-15, but the values may be adjusted for any composite/honeycomb structure. The parameters also set the timing of the data acquisition, including the rate and duration of acquiring images. The operating parameters are set in the Inspection Settings screen, which is available from the Configure drop down menu from the IRIS main screen. The listing of operating parameters is saved in the master inspection folder when an inspection is initiated.

The IRIS software is started by clicking an icon on the computer desktop. The IR camera is automatically detected and initialized, and all testing parameters are initialized when the IRIS software is started. The IR camera is continuously active during an inspection, and the IR image can be viewed at any time by clicking the Preview Camera button.

An inspection is started by entering Inspection information, which includes a site identifier, location, aircraft type, aircraft component and serial number, operators, and a comment. The operator indicates whether the location module will be used and which vertical stabilizer is being inspected. The size and shape of the F-15 vertical stabilizer is recalled from an internal library if the IR Ruler method of location is to be used. The IRIS will perform an inspection, tallying a list of detections even if the location method is not selected. If no location method is selected, the detections will not be located and the coverage map and flaw map will not be generated.

Figure 20:
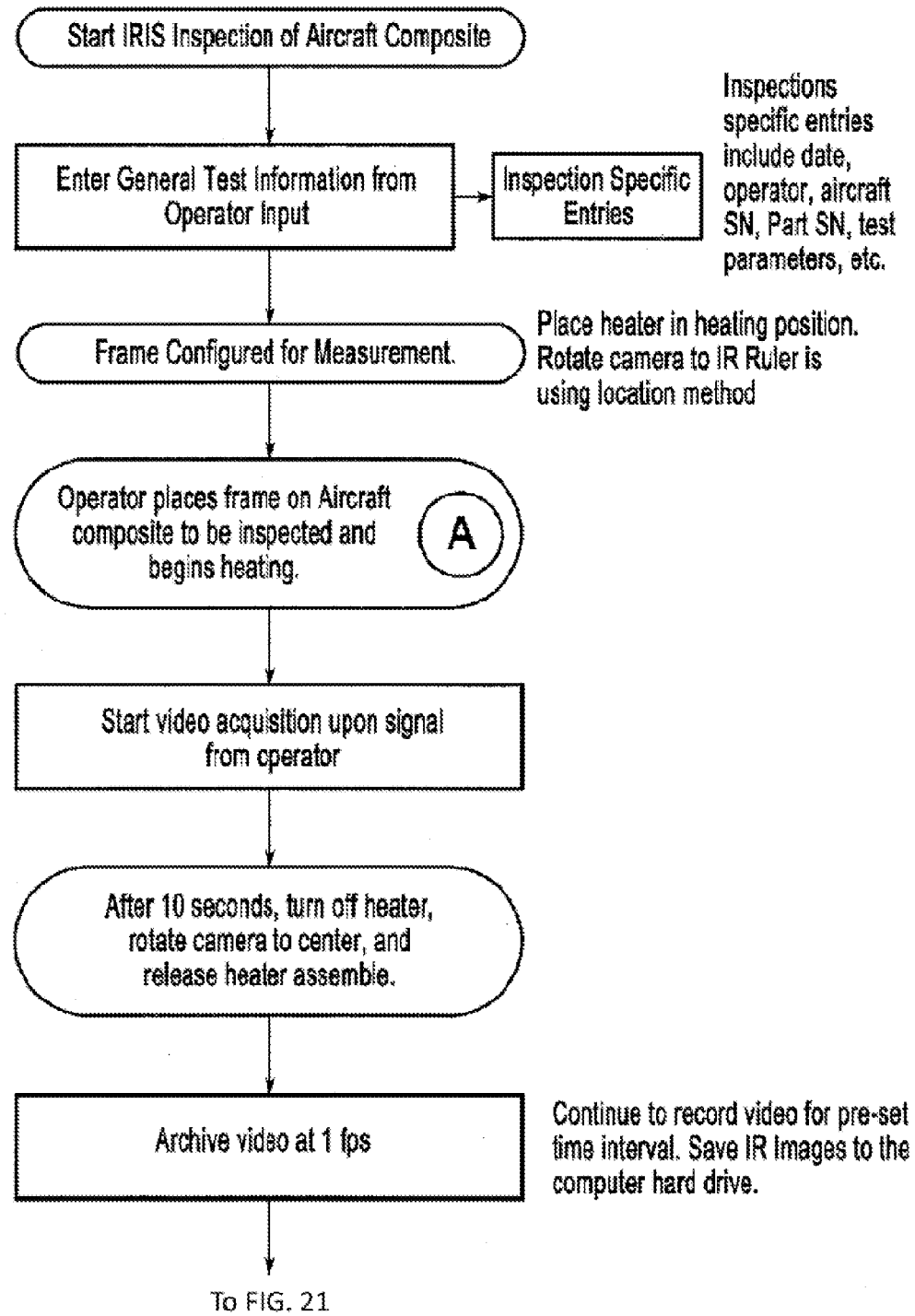
FIG. 20 illustrates the process flow of the image acquisition portion of the IRIS software.

The software steps the operator through conducting a measurement with on-screen instructions. The operator is instructed to configure the frame for the measurement by latching the heater in the heating position and rotating the camera to view the IR Ruler. The operator places the frame on the aircraft composite and powers the heater with a button on the control grip. Exact positioning of the frame is not necessary. The only requirement is that the IR Ruler is visible in the camera view at the start of the measurement. The frame does not need to be parallel to the ground, the leading edge, or even the previous measurement. Image acquisition is started at the IRIS computer by the second operator. The composite surface is heated for 10 seconds, at which point the operator rotates the camera back to the center position, turns off the heater by releasing the heater button, and releases the heating mat assembly by activating the latch with a button on the control grip. The heating mat falls out of the view of the camera by gravity. The frame is held in place on the composite during data collection. Any small movements of the frame that may occur are not of concern since only single IR images (not averaged IR images that require precise registration) are used in the analysis. IR images are recorded for a total preset time interval, typically 60 seconds; this includes heating time. The software alerts the operator when data collection is complete, and the operator may remove the frame from the composite surface. The images from the IR camera are displayed during data collection. FIG. 20 summarizes the steps of acquiring the IR images.

Figure 21:
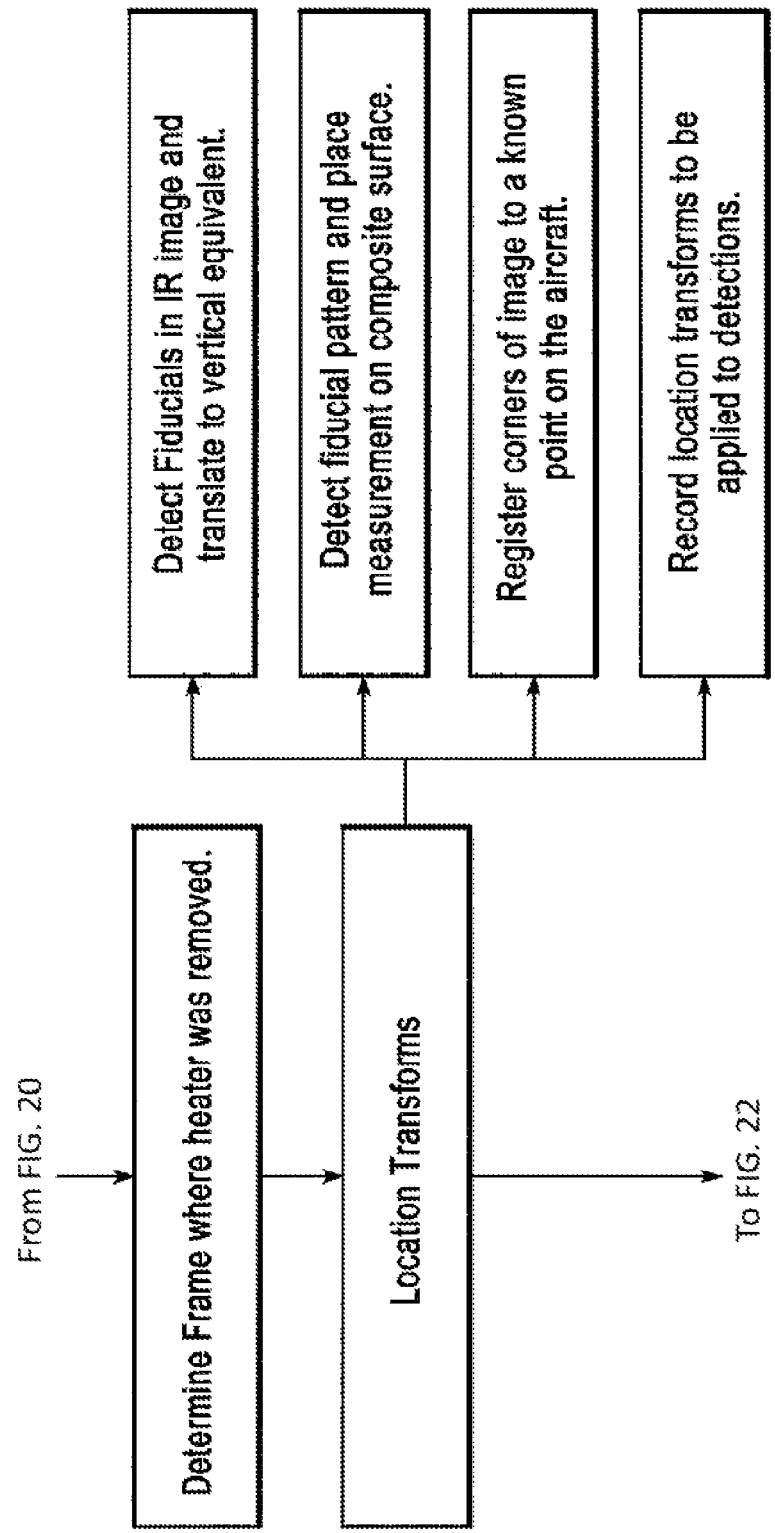
FIG. 21 illustrates the process flow for the location algorithms of the IRIS software.
Figure 22:
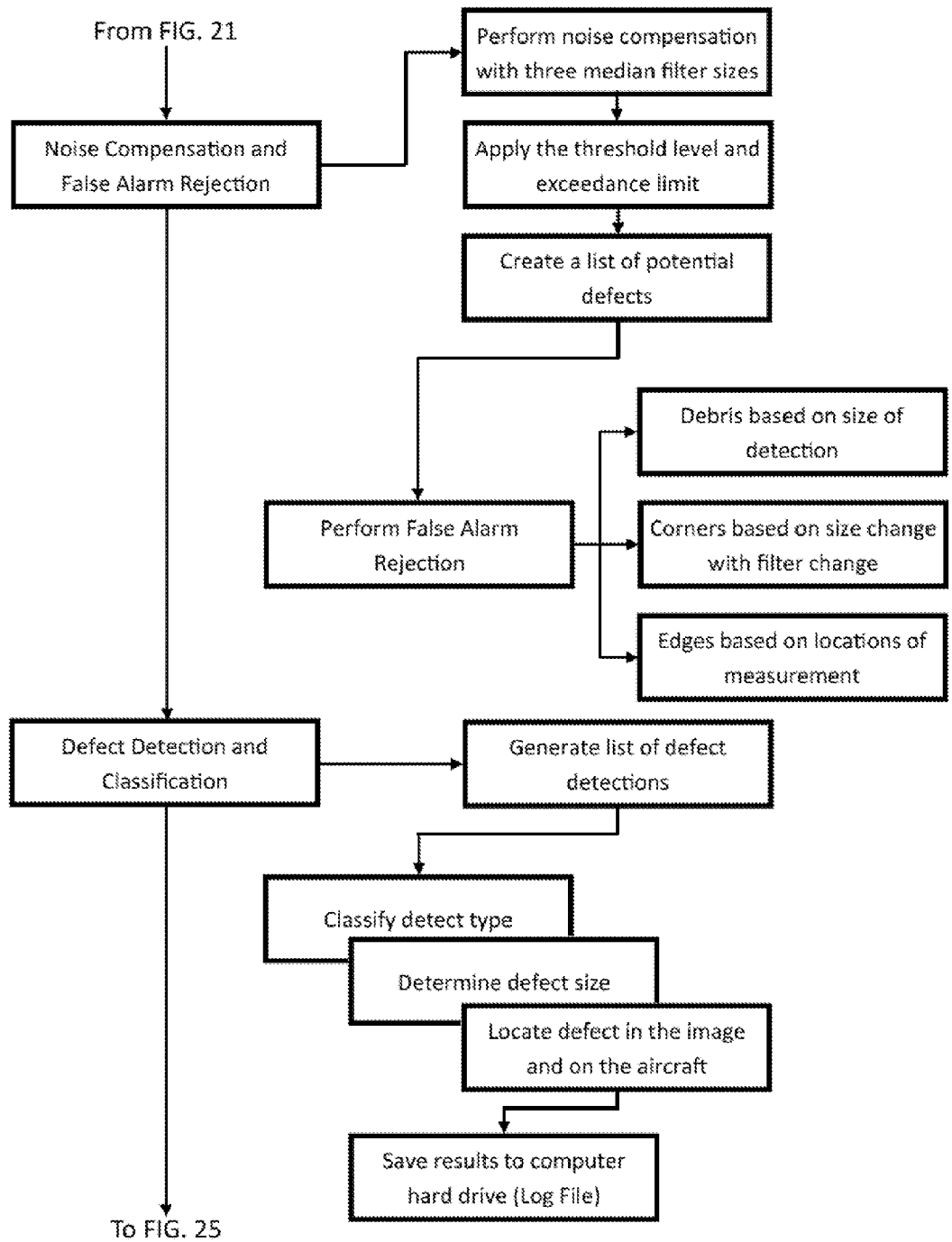
FIG. 22 illustrates the process flow of the false alarm mitigation and detection portion of the IRIS software.

Once data collection is complete, no further operator input is required for the duration of the measurement. The system progresses immediately to the location algorithms. The steps of the location process are shown in FIG. 21. The recorded IR images are processed temporally to determine at what time the heater was removed. This determination is critical to selecting the proper IR image for the location analysis and detecting delaminations. IR images for the location analysis are recorded during the 10 seconds prior to removing the heater. The delamination analysis image is automatically selected 2 to 5 seconds after removing the heater. The proper image for detecting disbonds and fluid ingress is not as critical in that these signals remain strong and highly visible for seconds 20 through 40. Any of the images with in this range are acceptable for processing. The software automatically selected the image 30 seconds after removing the heater.

Location transformation equations are determined from an IR image containing the fiducials. The location of each fiducial is detected in the image, and each location is converted to a vertical equivalent (the camera is set at an angle when recording fiducial images) so that the specific pattern can be identified. Geometric transforms were implemented that locate the corners of the image to the upper trailing edge corner of the composite surface. A detailed description of the location analysis was presented earlier in this section.

The process of detecting each type of flaw is done independently, because each flaw requires a specific IR image during the cooling process. Additionally, each type of defect requires specific noise compensation filter sizes, threshold levels, and exceedance levels. Though the settings are different for the different flaws, the steps of the detection and false alarm mitigation routines are the same for each defect. See FIG. 22.

The detection process for each measurement is accomplished in four steps. First, the raw IR intensity data (raw IR image) are compensated for the systematic noise produced by the heater using a simple median filter noise compensation method. The mean noise level at each pixel is estimated by computing the median value in an area centered on each and every pixel in the image. This works best when any defects present are no larger in size than ⅓ to ½ the size of the median filter area. However, it also works fine when the defects are larger. To accommodate different size defects, the analysis is performed multiple times with different filter sizes. To maintain robust processing, to get the best estimate of the size of any defects detected, and to mitigate false targets, the detection and classification analysis is performed three times with increasingly larger median filters.

Second, any grouping of pixels with IR intensities greater than the preselected threshold are tagged as possible defects. The number of pixels in a grouping defines the smallest target defect and is referred to as the exceedance limit. This is currently set to 30 pixels which covers an area of about 0.33 in. by 0.33 in. This size grouping of pixel insures that no random spike in a pixel will result on a potential defect.

Third, once a list of possible defects is identified, the defects in the list are each analyzed to determine if they are real, a false alarm, or a false target. Methods of false alarm mitigation are applied in the analysis. The first removes any signals produced by a small speck of debris on the composite surface. Setting the exceedance limit (the minimum size of a pixel cluster) to greater than the size of a bit of debris will prevent debris from causing false detections. Typical debris detections are a cluster of less than 5 pixels, and they are removed by setting the minimum detection size to above 30. Potential false target caused by the measurement extending off the composite to the aluminum surrounding the composite are eliminated by knowing the location of the measurement. When the edge of the composite surface is known to exist in the IR image, detections along this junction are removed.

Lastly, any detections not eliminated by the false target mitigation routines are declared as defects, and the location, size, and classification routines are applied. The above analysis is run for each of the three defect types, and a table is created for the measurement. The table includes the measurement number, the type of flaw, the location of the flaw from the upper trailing corner of the composite, and the size of the flaw in square inches. A folder is created on the computer hard drive for each measurement within the inspection folder. The array of IR images and the table of detections are written to the measurement folder. A file containing the image corner locations and the location transformation equations is also saved in the measurement folder.

Figure 23:
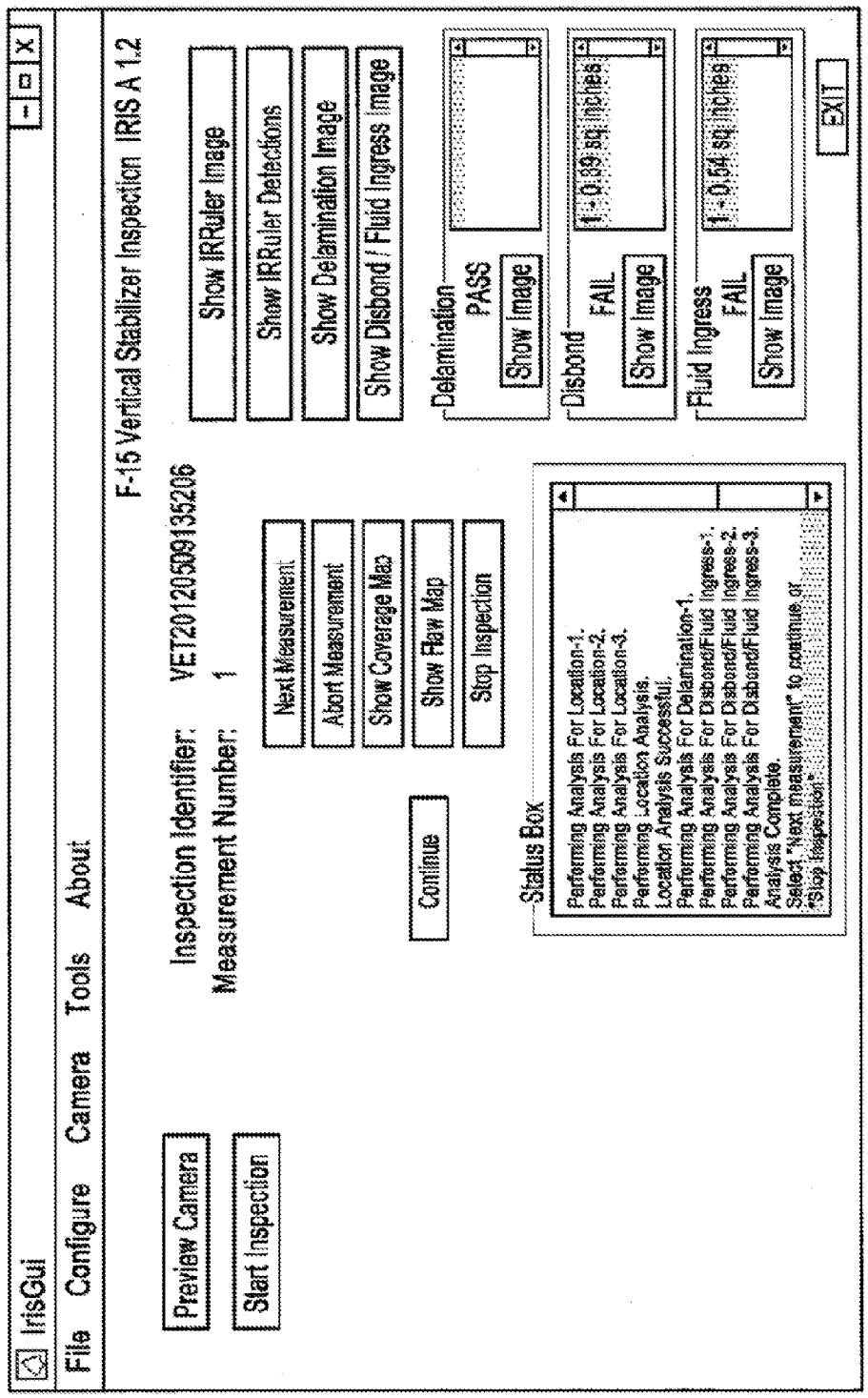
FIG. 23 illustrates the IRIS graphical user interface main screen showing the results of an individual measurement.
Figure 24:
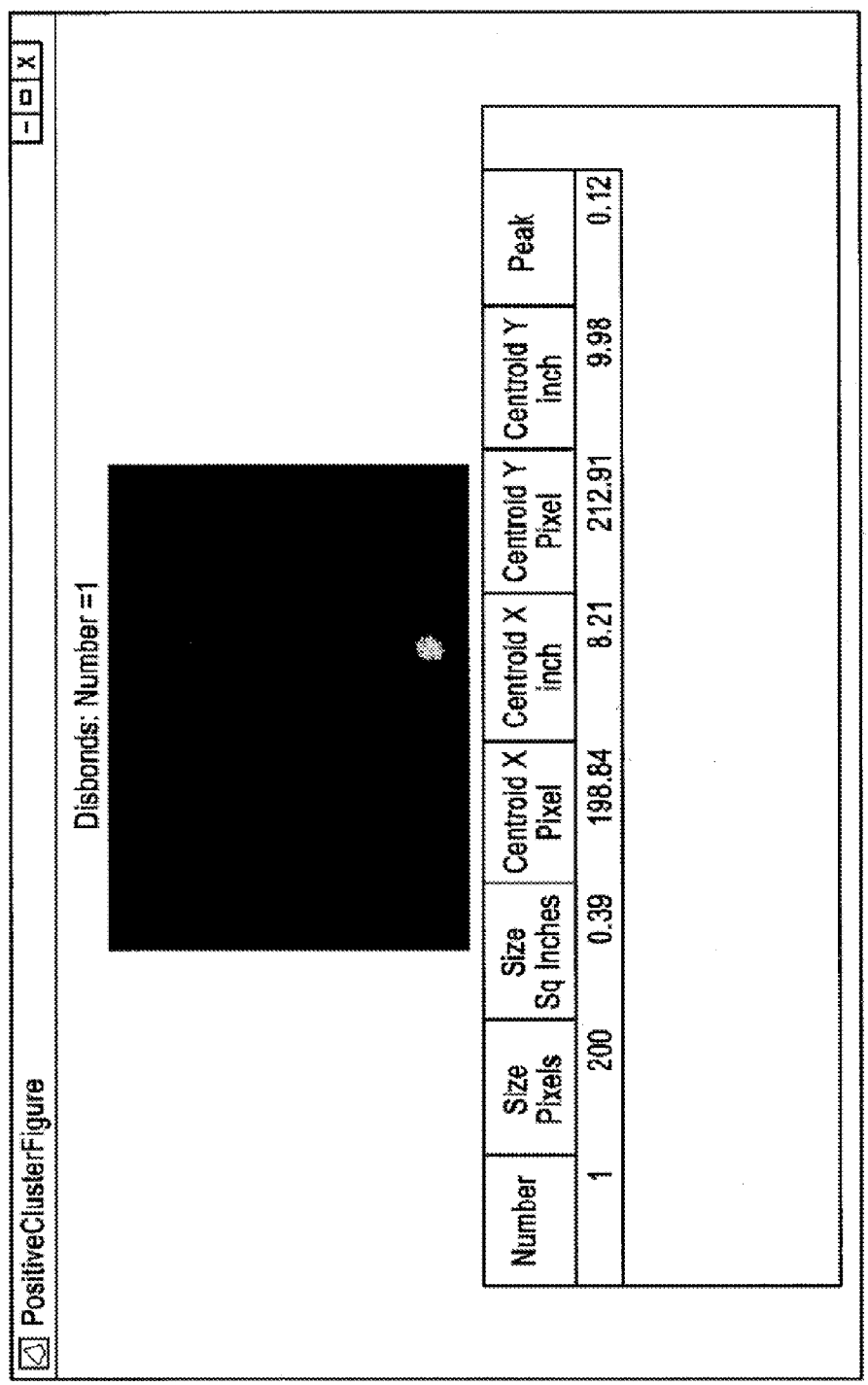
FIG. 24 illustrates the cluster map and flaw table for a disbond.
Figure 25:
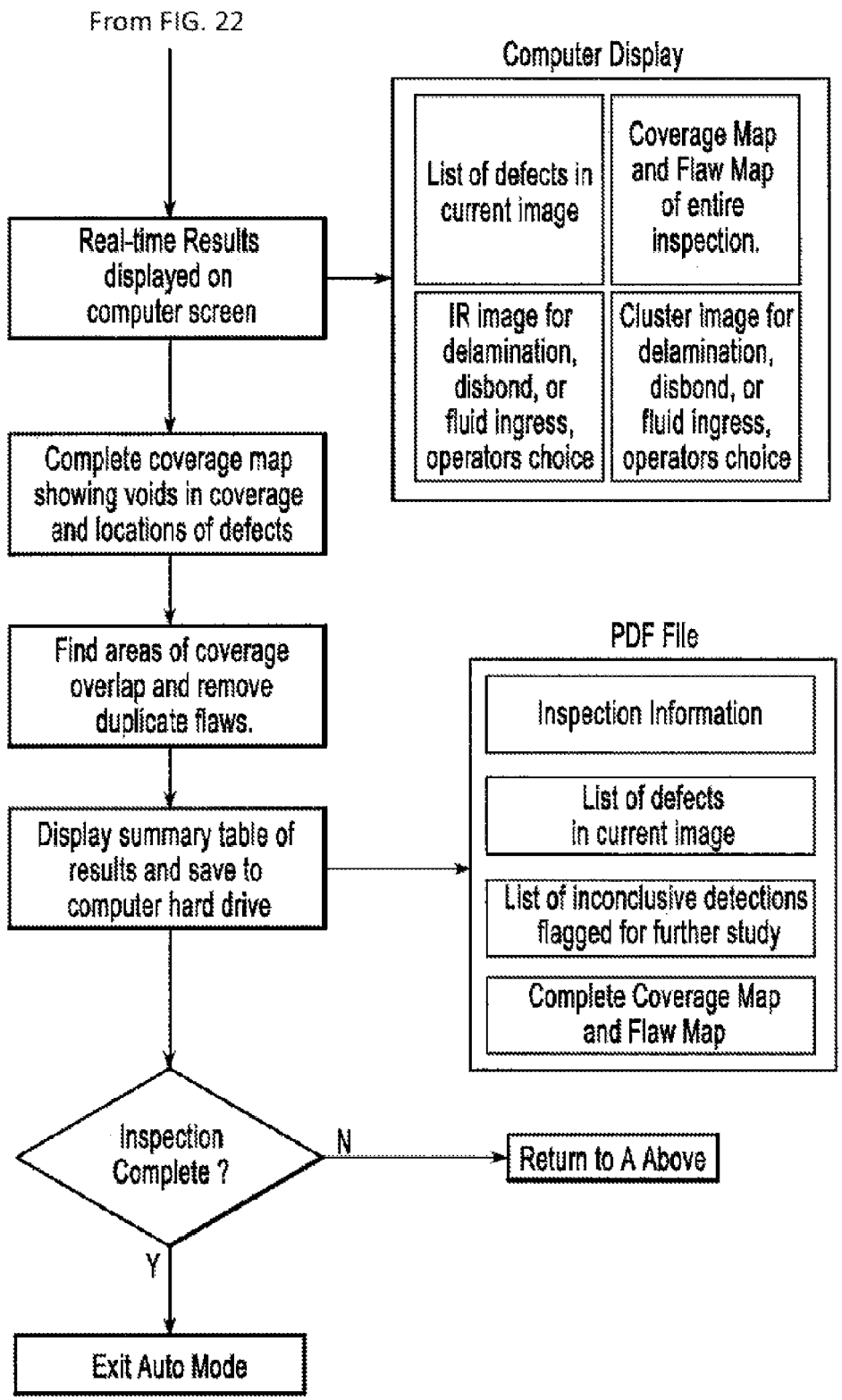
FIG. 25 illustrates the process flow of the results display and archiving of the IRIS software.

FIG. 25 describes the output of the software. The measurement results are displayed on the computer screen and must be acknowledged by the operator before continuing with the next measurement. This confirmation step ensures that the operator knows there is a flaw and provides an opportunity to make another measurement to confirm the presence of the flaw or to physically mark the location of the flaw on the composite. FIG. 23 shows the IRIS main screen displaying the results following an individual measurement. The inspection label and measurement number are shown. Four buttons control the flow of an inspection (Next Measurement, Start Camera, Abort Measurement, and Stop Inspection). The Show Coverage Map and Show Flaw Map display the results of the complete inspection. The three boxes to the right of the screen display the results of the current measurement. The results for each classification of flaw is shown with a PASS/FAIL indication with a green background if no detections were found (PASS), or a red background if a flaw was detected (FAIL). Clicking the associated Show Image button displays the cluster map and the table of detections (see FIG. 24). The IR image analyzed for each type of flaw and the location analysis can be viewed by clicking one of the four buttons above the results.

An inspection is made up of multiple measurements covering the surface of the composite. These measurements may slightly overlap to ensure complete coverage during the inspection. An additional detection routine is applied to flaws detected in overlapping regions. A flaw detected in an overlapping region must appear in each overlapping measurement to be considered an actual detection. In this case, the flaw is considered a single flaw, and any duplicate flaws are removed. If the case comes up that a flaw is not detected in all the measurements of an overlapping area, the flaws are marked as inconclusive to alert the operator to review this area.

A summary report, in PDF format, is generated at the completion of an inspection. When the inspection is complete, the summary report is saved in the Inspection master folder on the computer hard drive. The summary report contains the inspection information entered by the user at the start of the inspection. It contains the listing of all confirmed flaws showing which measurements detected the flaw, the type of flaw, the location, and the size. It also contains a listing of inconclusive flaws with the same information. The inconclusive listing shows regions of the structure which should be reexamined. Lastly, it contains the complete coverage map and updated flaw map indicating where confirmed and inconclusive detections were found.

The last step is to determine if the inspection is complete or if additional measurements are to be conducted. If the inspection is to be continued, the operator configures the frame for the next measurement and places it on the composite surface at the next location and initiates the next measurement. When the inspection is complete, the data and summary files are closed, and the computer memory is cleared.

Post-Test Analysis Software for Validation Analysis.

A unique and beneficial aspect of the IRIS software package is the Post-Test Analysis module, which allows complete freedom in applying the analysis algorithms in a manual mode. The post-test analysis module contains all the detection routines used in the automatic code but allows the user to fine tune the analysis for a more detailed processing of the IR images. The module may be used to validate the results of the automated test or to reexamine inconclusive detections.

Figure 26:
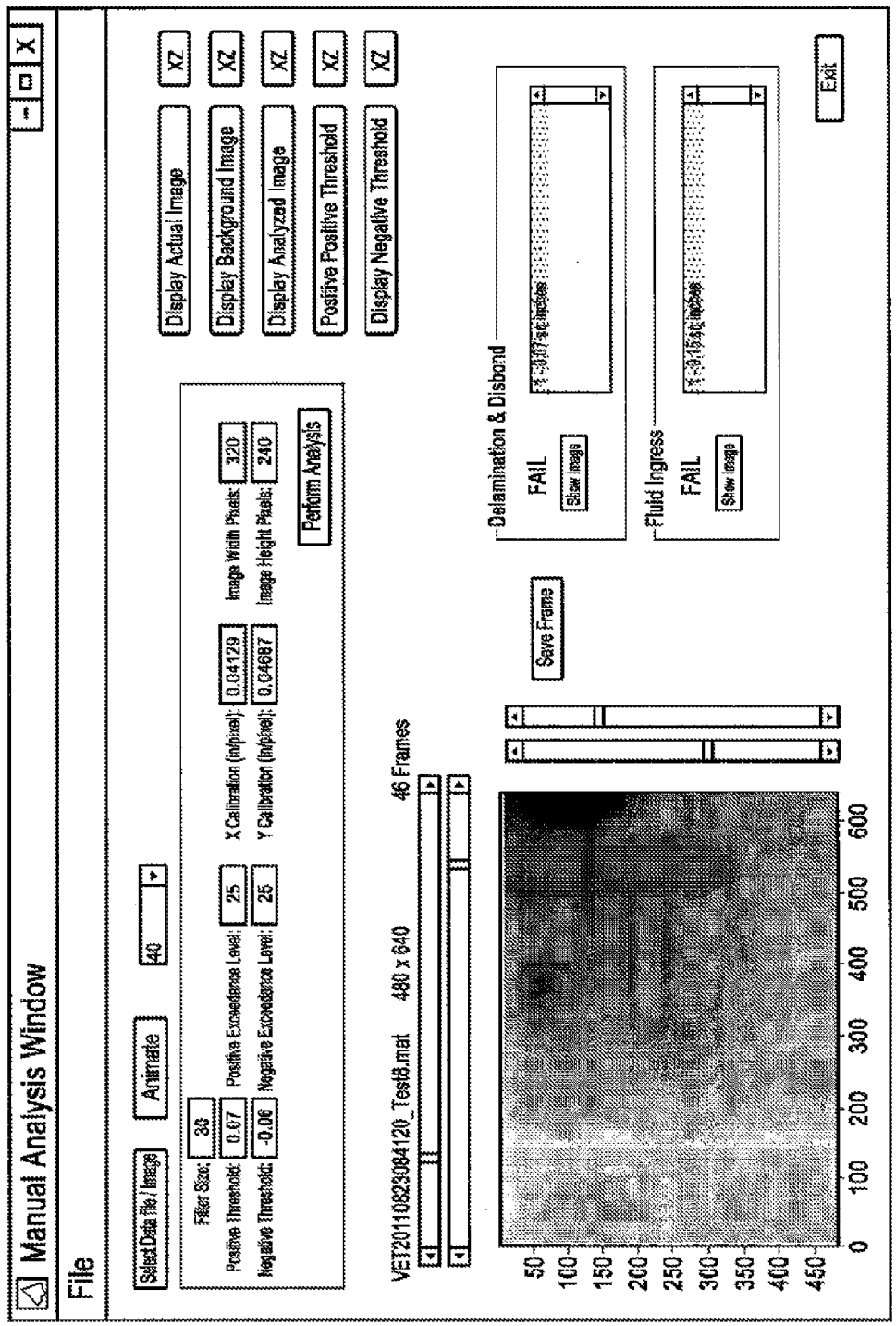
FIG. 26 illustrates post-test analysis module that allows detailed processing and validation of results.

The post-test analysis software can also be used to process IR images obtained on aircraft composite structures other than those recorded on a vertical stabilizer. If a measurement is conducted on an airbrake or rudder, this module lets the analysis parameters be tuned to the specific structure being inspected. The module uses the IR images recorded during an automatic inspection. The user can then select which frame to analyze and may select only a portion of the entire IR image for closer inspection. The user has the freedom to change the threshold, exceedance levels, and noise compensation filter size. It also lets the user view the results of the intermediate steps of the analysis. The Post-Test Analysis window is shown in FIG. 26.

The same type of analysis performed in real-time can be performed using the Post-Test Analysis Module. The cursors on the display allow the user to look at specific areas of the IR image.

There are five general types of displays. For each display there are three pre-set displays (a) a two-dimensional contour plot of the surface (which mimics the view obtained by the video camera); (b) a three-dimensional plot, which shows the magnitude of the defect); and (c) a vertical profile view (i.e., an average cross-sectional "slice" of the 3-D display). The two-dimensional contour plot of the surface is very good for identifying the defect signals. The three-dimensional plot shows the general magnitude of the background and the defects. The vertical profile view is excellent for indicating the magnitude of the defect signal. The profile view is best used after the 2-D or 3-D views are reviewed. The five displays are:

Display Actual Image. Used to display the IR image to be analyzed.

Display Background Image. Used to display the background.

Display Analyzed Image. Used to display the defect signals present.

Positive Threshold Plot. Decision criterion used to detect and identify disbonds.

Negative Threshold Plot. Decision criterion used to detect and identify fluid ingress regions.

Figure 31:
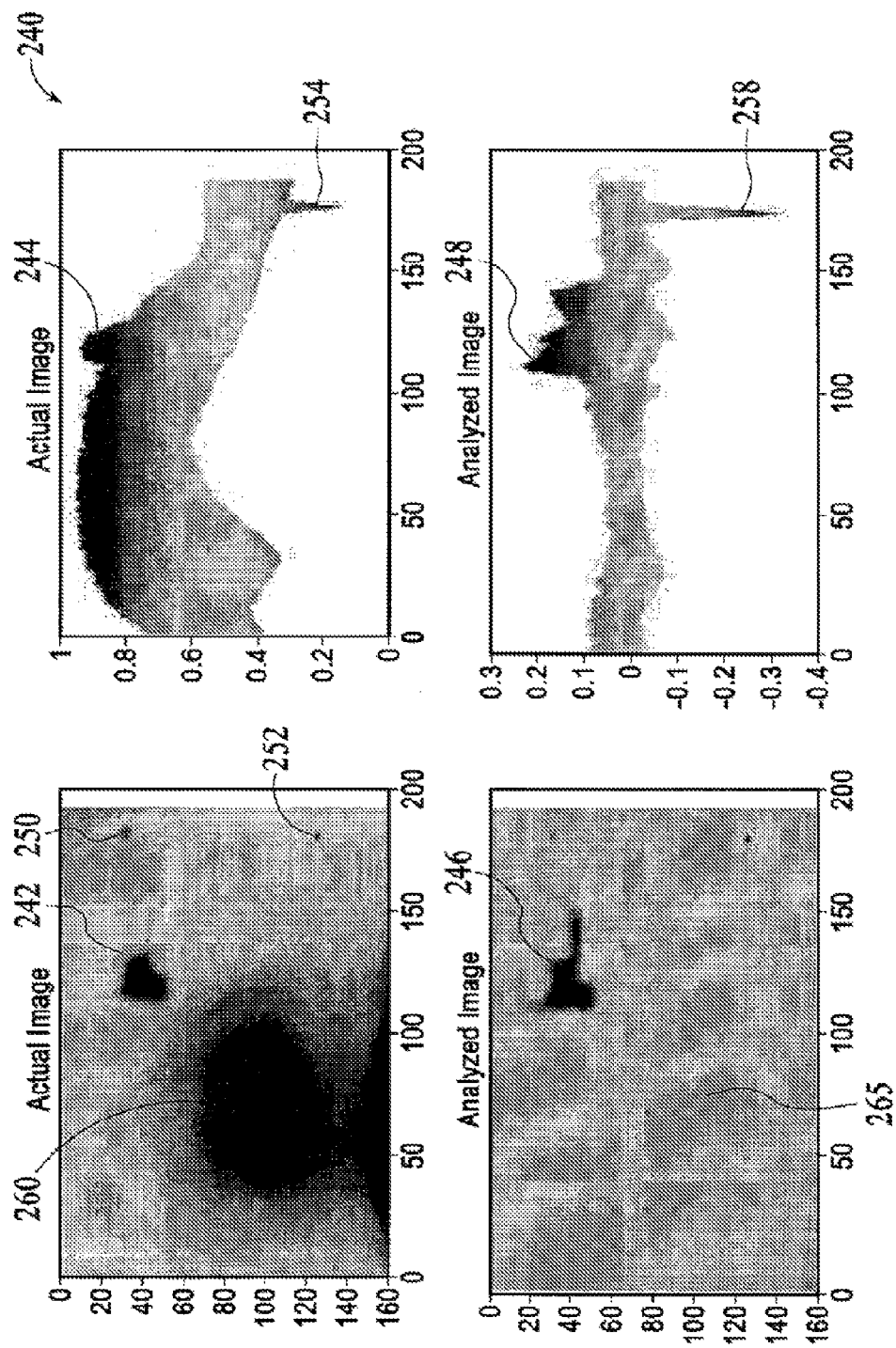
FIG. 31 illustrates a contour map and a vertical profile of the raw IR data at the top and a contour map and vertical profile shows the results after the processing has been completed at the bottom.

The software can use either (1) single IR images obtained during an inspection, or (2) a continuous stream of images obtained automatically at 1-s intervals from IR videos obtained during the inspection. An example of a two-dimensional contour map of the Actual Image (i.e., raw IR Intensity), and a two-dimensional contour map of the Computed Background. FIG. 31 shows a two-dimensional contour map and a cross-sectional profile of the Actual Image and the Analyzed Image (i.e., after the Background was subtracted. It is clear that the Analyzed Image reduces the background noise and allows the selection of a threshold that will detect the disbond or the fluid ingress. If a threshold were selected for the Actual IR image, one can see that the high intensity of the background would also exceed the threshold. An inspection test was conducted on a section of a rudder from an F-15 aircraft with a skin-to-core disbond created in the laboratory.

Location of the Defects and Coverage Map Using an IR Camera and an IR Ruler.

The location of the IR camera, each IR image, and the location of each defect detected in each IR image is determined with respect to a known point on the composite structure itself using the IR camera and an IR Ruler. The IR Ruler is a strip of fiducials (low-power resistors) that is placed along the leading edge of the composite. The resistors are sandwiched between a felt upper surface and a rubber backing. The resistors are arranged in a special pattern that can be interpreted in terms of feet and inches. Because the field of view of the IR camera is small, the pattern can be interpreted with only three or more electrical resistors. Standard photogrammetric and coordinate transformation analysis methods are used to determine the position of any point in the IR image relative to the known point on the composite structure.

Figure 27:
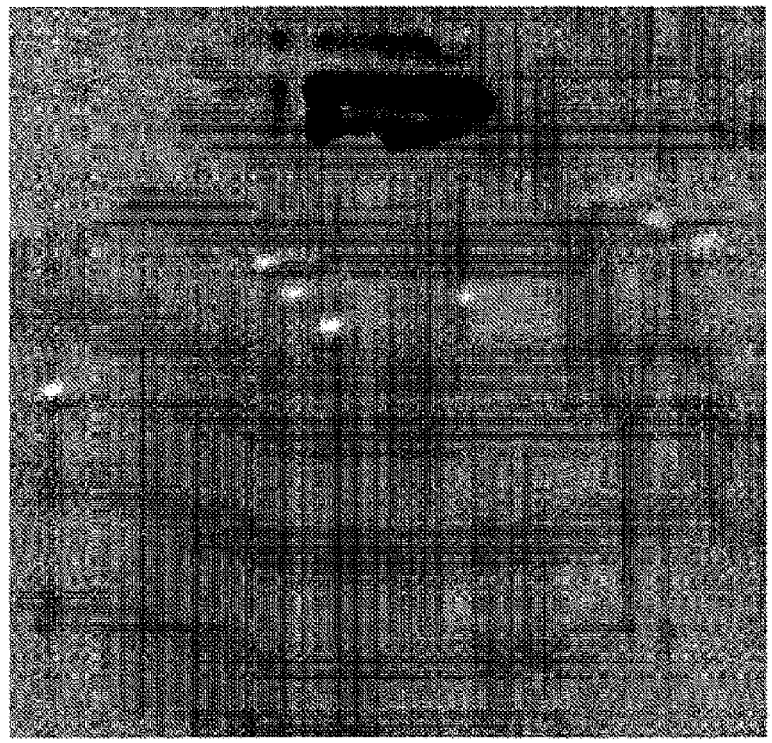
FIG. 27 illustrates the IR Ruler positioned on the vertical stabilizer and the IR image of the IR Ruler recorded during the heating step of a measurement.
Figure 27:
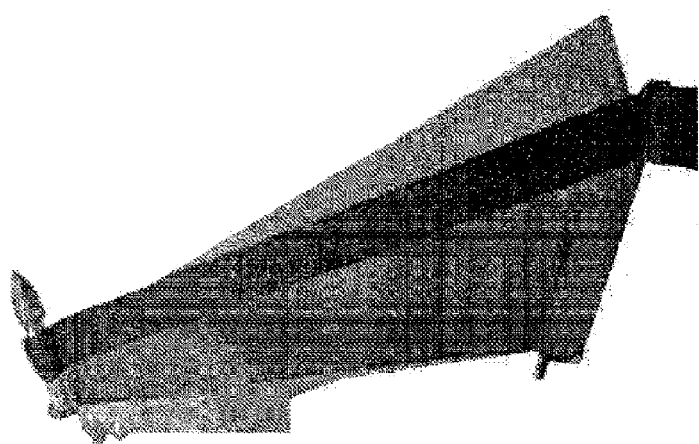

The IRRuler is viewed by the camera during the heating portion of each measurement. The IR camera is rotated toward the IR Ruler during the heating portion of a measurement and records IR images of the IR Ruler. The operator then rotates the camera back to center before the heater is released. The location algorithm detects the fiducials in the oblique field of view, determines the pattern, and places the measurement at the correct location on the composite surface. FIG. 27 shows the IR Ruler, its location on an F-15 vertical stabilizer, and an IR image obtained for one IR measurement made on the vertical stabilizer.

Figure 28:
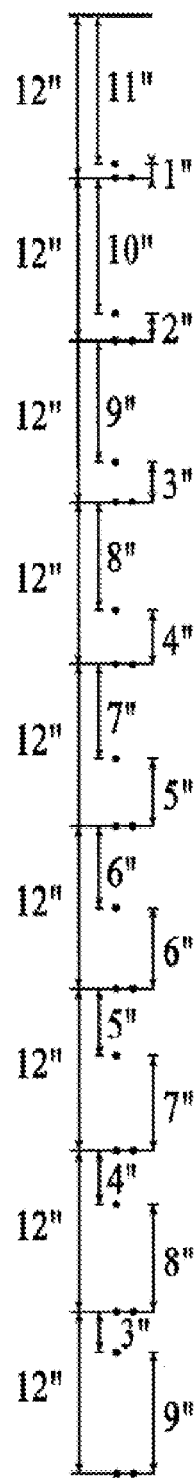
FIG. 28 illustrates the specific pattern of fiducials used in the IR Ruler which dictates where along the stabilizer the camera is located.

As illustrated in FIG. 28, the resistor pattern is made up of placing 2 resistors adjacent to each other every 12 inches to indicated foot markers. From the marker that is one foot from the top of the stabilizer, another marker is placed 1 inch higher. Similarly, at two feet from the top of the stabilizer, the additional marker is placed two inches higher than the foot marker. The pattern continues down the length of the vertical stabilizer. This pattern has several advantages. First, just by looking at the spacing between the foot marker and the additional marker, the approximate position on the stabilizer can be ascertained. Second, with the vertical field of view of the camera being approximately 17 inches, at least 3 markers will always be in the field of view. Lastly, the pattern is unique such that there is no repetition of the spacing.

Each fiducial is an electrical resistor that is powered by a 9V battery pack (or can be powered with an AC wall adaptor). The heat produced by the resistor is enough to make the resistor appear as a bright spot on the IR images.

Figure 29:
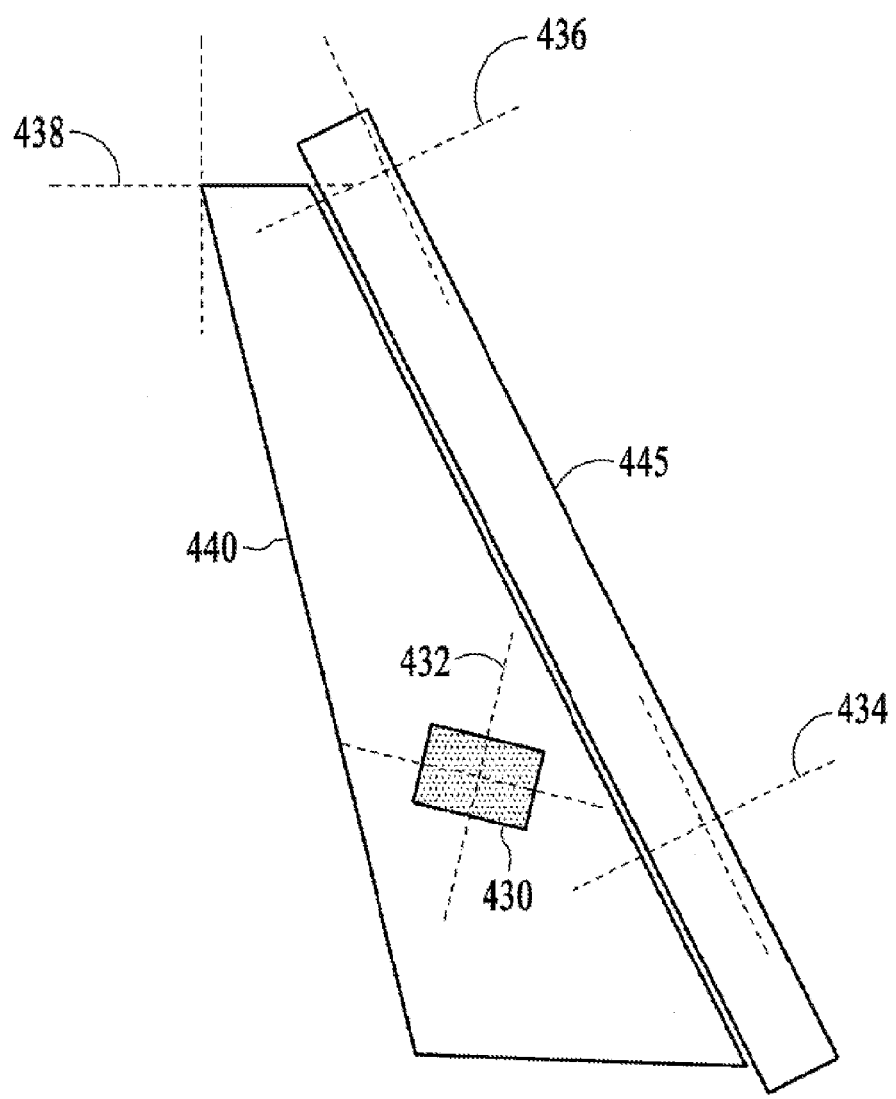
FIG. 29 illustrates the axis transformations used to place the measurement at its exact location on the vertical stabilizer.

Analysis similar to the detection of disbonds or delaminations in the IR image during the inspection is used to detect the fiducials in the IR image. A threshold is applied to the IR image and clusters of pixels larger than the exceedance number are located. The image is then transformed from an oblique image to a vertical equivalent so the specific pattern can be identified and interpreted in terms of feet and inches. The pattern of the fiducials dictates where the measurement is being conducted. Multiple coordinate transformations are needed to reference the measurement to a known point at the top of the stabilizer (i.e., the upper corner of the composite). FIG. 29 shows the transformation geometry. The shaded rectangle is the measurement location of the IR image. The image location is determined by where and how the operator places the frame on the composite surface. The only requirement in placing the frame on the composite surface is that the IR Ruler must be in the view of the camera during the heating portion of the test. The frame does not need to be parallel to the ground or parallel to the leading edge. Consecutive measurements may overlap or a measurement may be rerun at the same location. The location of the detected fiducials is obtained in an oblique image and reference to the coordinate system of the image, i.e., the dashed X-Y coordinate system. The points of interest on the measurement coordinate system are translated to the X-Y IR Ruler coordinate system (i.e., the green cross hatch), to the top X-Y IR Ruler coordinate system (i.e., the black cross hatch), and then to the X-Y coordinate system on the vertical stabilizer (i.e., the red cross hatch).

The corner locations of the measurement image translated to the X-Y stabilizer coordinate system (indicated at the top of the FIG. 29) is saved for each measurement. Similarly, any detections within the image are translated to the X-Y stabilizer coordinate system and saved with the results.

Figure 30:
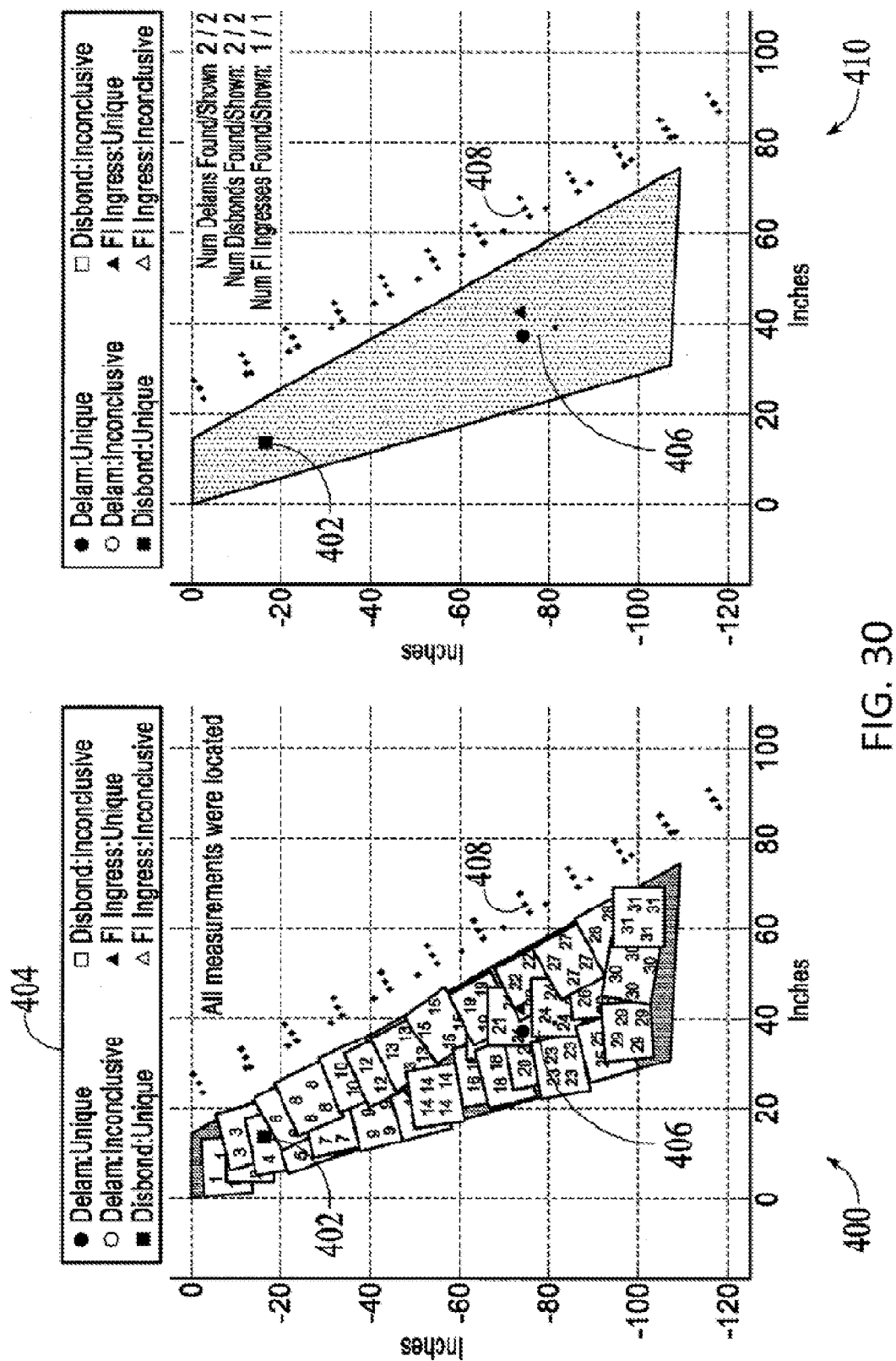
FIG. 30 illustrates the coverage map with measurement numbers and the flaw map that the IRIS creates at the end of an inspection.

At the completion of each measurement, a coverage map is generated showing areas of the composite surface that has and has not been inspected, allowing the operator to return to a region of the composite that might have been missed. A flaw map and a coverage map are shown in FIG. 30.

Each measurement is located uniquely using the IR fiducial images collected with each individual IR measurement. This has benefits in that measurements may be conducted in any order and do not have to be conducted immediately following the previous measurement. A typical inspection may be conducted from the top of the stabilizer to the bottom. At any time during the inspection, the operator may backtrack and perform a measurement in an area previously missed without effecting the coverage map or detection locations. Additionally, the inspection may be paused for a period of time and re-continued at a later time should the operators need to stop for any reason.

Remote Control and Analysis of an NDT field inspection. The IR computer controlling the test can be left unattended and run remotely via the internet. A program such as GoToMeeting, which allows test operation, control, analysis, display to be controlled by a remote computer. This second computer can be operated at the base of the tower, from another location in the build, or another location anywhere there is an internet connection. Additional users can have access at the same time.

Background Noise.

Background data was processed to obtain estimates of the background standard deviation for a range of composite locations, thicknesses, and heating times and the peak IR intensities of the disbond and delamination defects.

Over 30 tests were conducted on the composite material of the F-15 stabilizers that were believed to not contain any flaws. These tests provided a good overall sampling of the noise behavior of the IRIS system. They included tests from both the thin, upper portion, and the thick, lower portion, of the stabilizer as well as tests with both 10 and 20 s of heating. The noise analysis involved processing the images with the IRIS algorithm and determining the spread of noise at various intervals during cooling.

Figure 32:
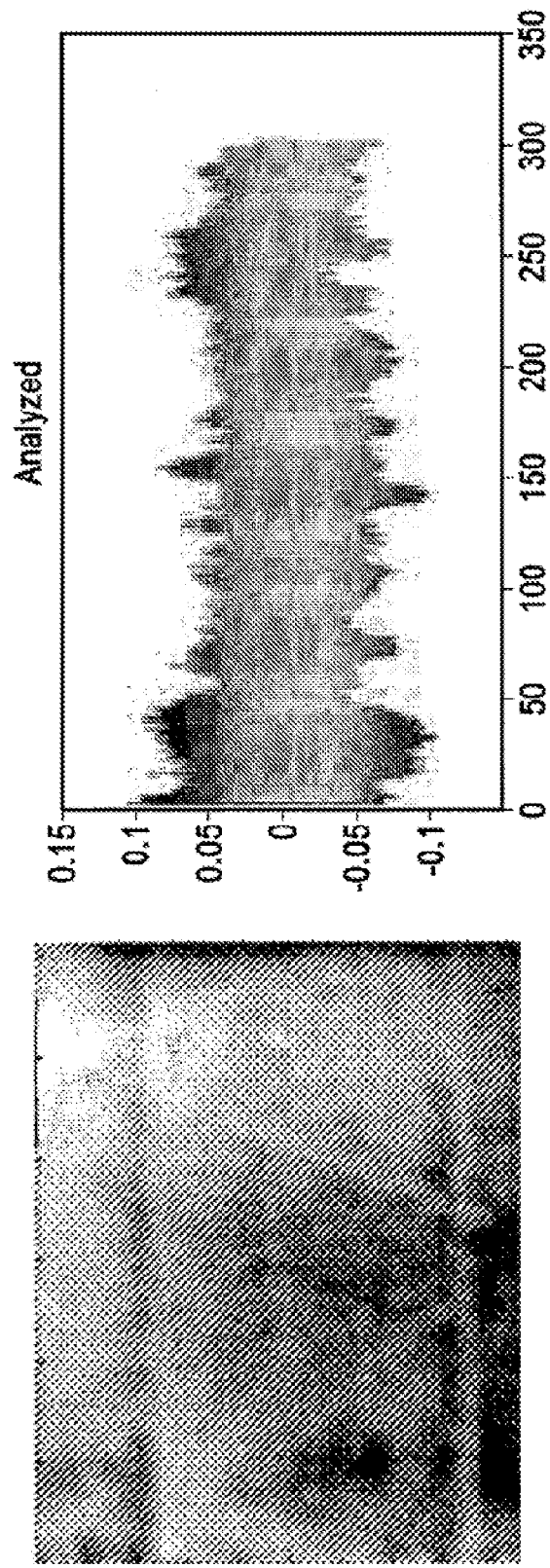
FIG. 32 illustrates the image and noise spread of a test conducted on the lower portion of the vertical stabilizer five seconds after removing the heater. The noise spread is from +0.1 to −0.1. The noise in the image is due mainly to the surface condition of the composite.
Figure 33:
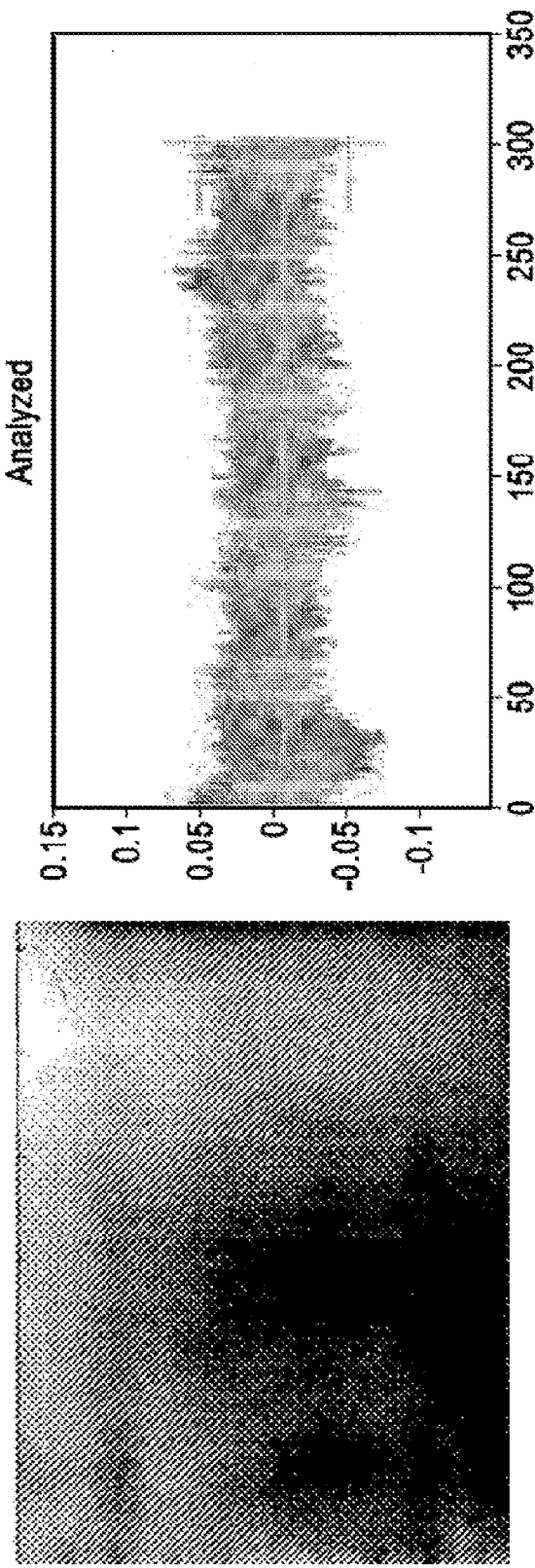
FIG. 33 illustrates the image and noise of a test conducted in the lower portion of the vertical stabilizer 30 s after removing the heater. The noise spread is +0.06 to −0.06.

FIG. 32 shows the image and the noise spread five seconds after removing the heater. This test was conducted on the lower (thicker composite) portion of the vertical stabilizer with a heating duration of 10 s. The image shows patterns on the composite surface due to the stabilizer having been prepared (depainted) for inspection. These patterns do not affect the results of the IRIS because they do not match the known thermal signature of the defects being investigated. The noise spread is shown in the image on the right by having a spread of about +0.1. FIG. 33 shows the same test but at 30 s after removing the heater. The heating patterns have dissipated and the heated portion of the image is much smoother. The noise spread has been decreased to less than +0.06 to −0.06.

Figure 34:
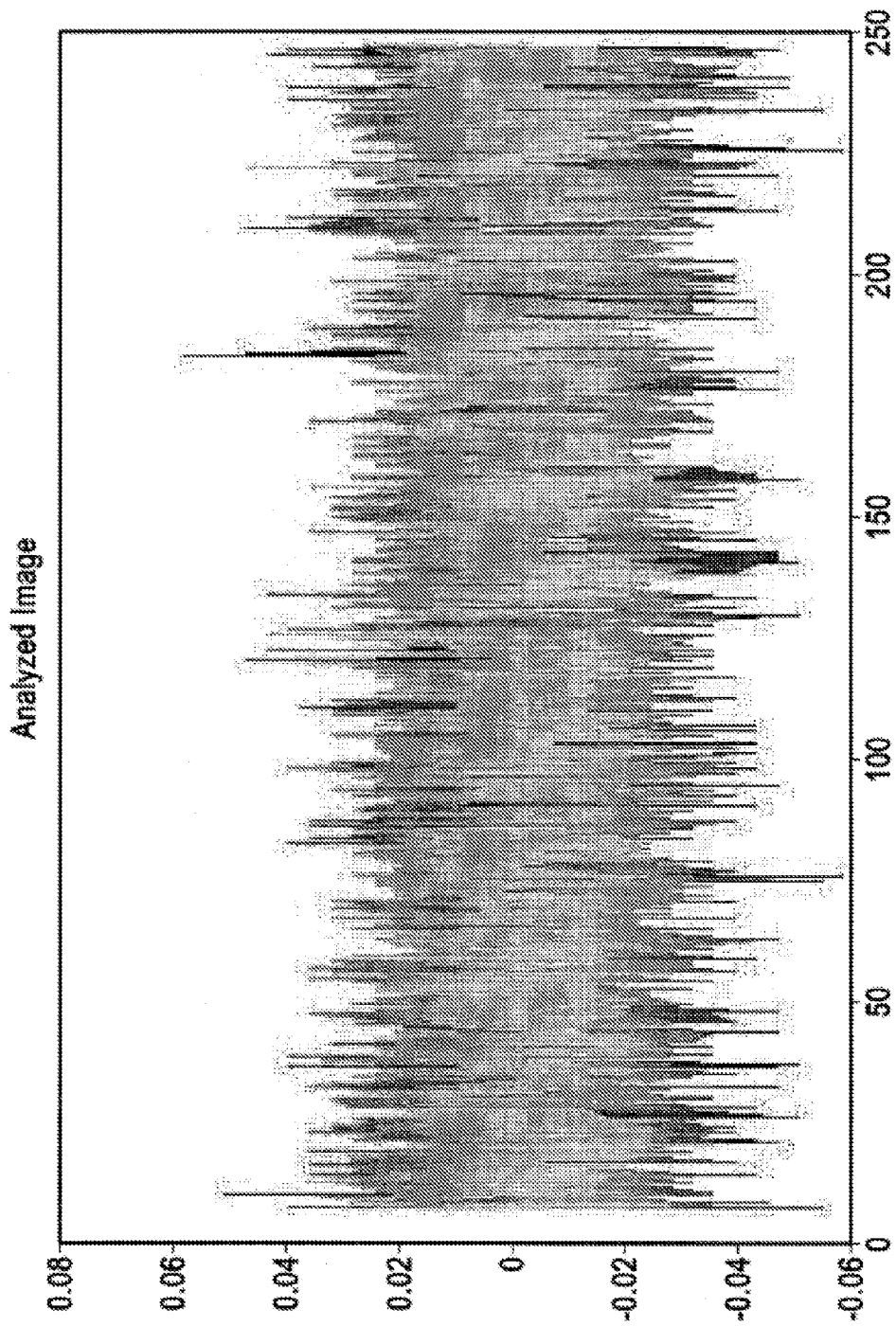
FIG. 34 illustrates the IR intensities at each pixel in the IR image. The standard deviation is 0.0141, which is 10 times smaller than the peak IR intensities due to disbond signals.

FIG. 34 shows the standard deviation of the IR measurements made before any heat was applied to the composite on the F-15 vertical stabilizer. The standard deviations for four frames occurring at ⅓ s intervals were 0.0139, 0.0144, 0.0142, and 0.0135, respectively. The surface temperature of the composite was at 95° F. The silicone mat heater raised the temperature of the surface by about 5° F. during the 10 s heating period. The background noise shown in FIG. 36 has approached these values.

Figure 35:
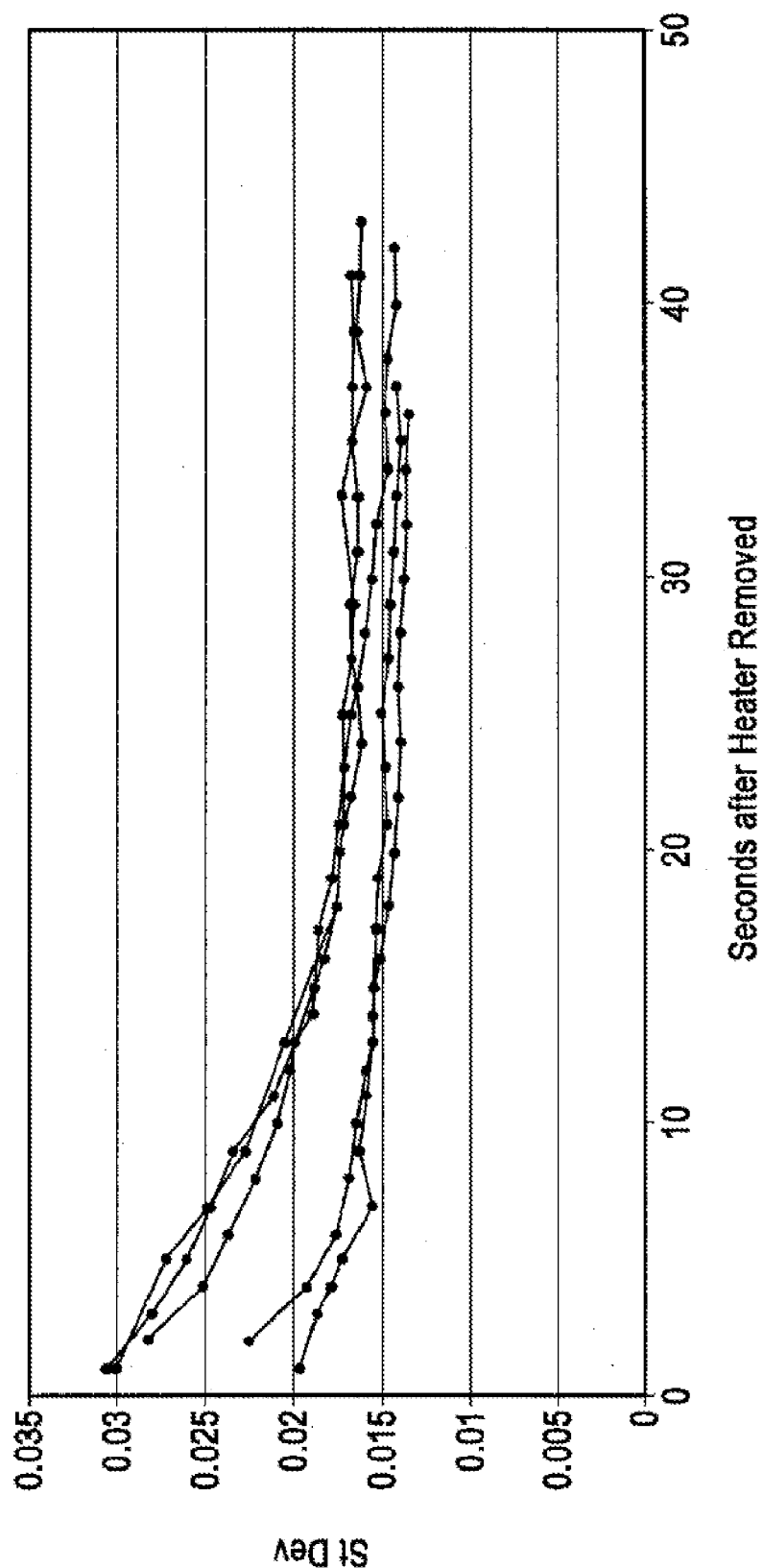
FIG. 35 illustrates the time history of the standard deviation of the background IR intensities measured on an F-15 vertical stabilizer with no defects present.
Figure 36:
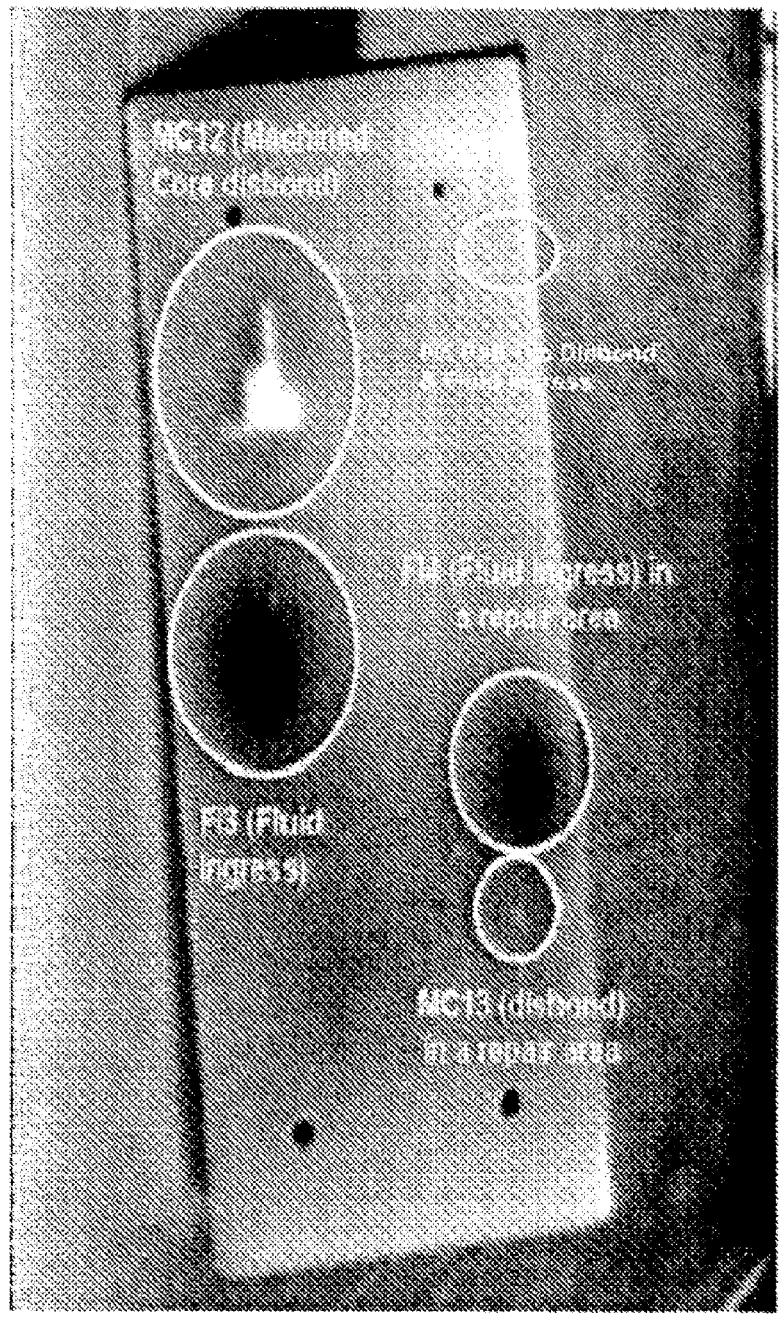
FIG. 36 illustrates the prepared test article with a multiple disbond, fluid ingress, and repaired regions.

FIG. 35 shows the standard deviation of the IR intensities measured for the background for an F-15 vertical stabilizer as a function of time. It was found that the noise levels decreased from the time the heater was removed to about 35 s after removing the heater. For times greater than 35 seconds, the IR intensity of the background approached a constant value. It was also found that the noise was decreased to limits very similar to what is shown in FIG. 36. At 15 s, the fluctuations are larger than at 45 s, and features of the composite surface can be seen. A minimum detection threshold can be selected based on these reduced noise levels. The detection threshold selected should be large enough to not detect noise (false alarms) but tight enough to not miss weak or small flaws (missed detections). Based on the analysis, a detection threshold of +0.07 should be applied 30 s after removal of the heat source.

In general, as illustrated in FIG. 35, a standard deviation of 0.0158 was computed for the selection of background noise tests conducted 30 s after the heat source was removed from the composite. A standard deviation of 0.0160 was used in the following calculations to be conservative, because it is larger than 0.0158 and is representative of the maximum obtained 30 s after the heat source is removed from the composite. This allows for the operator to select a set video frame for analysis, and allow for small differences in the time that the heat source is actually removed from the composite (say 30 to 40 s). The conduct of over 50 measurements on the F-15 suggests the operator can consistently apply the heat mat, wait 10 s, and remove the heat source within a 2 to 5 s.

As seen in the time histories shown in FIG. 35, there is very little chance (<1%) that a threshold of T=0.07 would be exceeded by the normal IR ambient background fluctuations, because the threshold is over 4 times larger than the maximum standard deviation at 30 seconds. Because a defect signal with an IR intensity of 0.10 is over 6 times larger than the maximum standard deviation, the noise fluctuations would not prevent the detection of an actual defect (probability of a missed detection $P_{MD}=1-P_D \leq 1\%$).

Performance.

Once the mean strength of the defect signal is known and the histogram of the ambient background noise fluctuations are known, an estimate of the performance of the IRIS for each type of defect can be made.

The performance of the method and the preferred and alternative embodiments has been evaluated several times over a period of several years with nearly identical results using IR inspection measurements obtained on the aluminum honeycomb composite on F-15 vertical stabilizers to estimate the $P_D$ and the $P_{FA}$ for defects as small as 0.25 in. (0.0625 in.$^2$). Table 1 summarizes the results for the disbonds and delaminations assuming that a $P_D$ of either 95% or 99% is required; the $P_{FA}$ is very low for each of the estimates. The performance for fluid ingress would be similar since this type of defect is stronger and more distinctive than the disbond and delamination defects. Table 1 indicates that operated with a $P_D$>99% and a $P_{FA}$<1% using either a pre-determined threshold, or a threshold adaptively determined from the background noise of the IR image being analyzed.

TABLE 1

Illustration of the Performance of the IRIS for Disbonds and Delaminations

| SNR-dB | Standard Deviation (σ) | $P_D$ | $P_{FA}$ | Mean IR Detection Limit | IR Threshold (T) | Defect |
|---|---|---|---|---|---|---|
| 15.6 | 0.0160 | 95.00% | 0.0007% | 0.096 | 0.070 | Disbond |
| 16.5 | 0.0160 | 99.00% | 0.0006% | 0.107 | 0.070 | Disbond |
| 17.3 | 0.0160 | 95.00% | 0.0000% | 0.117 | 0.090 | Disbond |
| 18.0 | 0.0160 | 99.00% | 0.0000% | 0.127 | 0.090 | Disbond |
| 21.3 | 0.0300 | 95.00% | 0.0000% | 0.350 | 0.300 | Delamination |
| 21.8 | 0.0300 | 99.00% | 0.0000% | 0.370 | 0.300 | Delamination |
| 18.4 | 0.0300 | 95.00% | 0.0000% | 0.250 | 0.200 | Delamination |
| 19.1 | 0.0300 | 99.00% | 0.0000% | 0.270 | 0.200 | Delamination |

IRIS Test Results.

The results of a large number of laboratory, full-scale, and field tests of damaged and undamaged honeycomb composite structures are described below.

Boron Composite Test Article.

A large number of tests have been conducted to demonstrate the feasibility of the IR measurement concept on specially prepared test articles provided by the Air Force with known defects, actual undamaged aircraft sections in which defects were created, on damaged and undamaged section of aircraft sections inspected by NDT technicians at Robins AFB, on F-15 aircraft in the depot with known damage, and on undamaged F-15 aircraft. An overview of some of these measurements is described below.

FIG. 36 shows the results of the IR image obtained after radiantly heating for several minutes a specialized aircraft boron composite of an F-15 Vertical Stabilizer (Test Article) for detection of skin-to-core disbonds and water ingress. The Test Article with defects of various known shapes and sizes as small as 0.5 in. and larger than 3.0 in. could be detected inside and outside of repair areas and with and without adhesive on the inside of the skin. A small, inexpensive, low resolution (320×240) uncooled IR microbolometer camera was used to make the measurements. The results were similar for all three methods used to raise the surface temperature of the honeycomb composite several degrees, but the conductive heating with a silicon heat mat proved to be the more consistent, less expensive, and easier to implement than the radiant and hot methods initially tested. Heating with the silicon mat took 10 s and measurements for delaminations, disbonds, and fluid ingress could be completed with 30 to 45 s (1 to 20 s). The methods of heating included making detections as the composite surface was being heated, during the cooling period after the composite surface was overheated and removed, and after uniform heating for a prescribed period of time.

Disbonds are detected as a strong "positive" peak (a white spot in the IR image) in the noise compensated processed IR image at one or more sections of the composite that are significantly above the other regions of the composite. A disbond is distinguished from a delamination, because the presence of the positive IR peak produced by a delamination is detected sooner, is stronger, and fades away quicker than the IR peak produced by a disbond. The IR peak produced by a delamination will appear within a second after the heat source is removed from the composite and will maintain a very strong signal for a period of 5 to 15 s, before it begins to decay. After 30 to 40 s, the delamination signal has decreased by a factor of 5 to 10. On the other hand, while the IR intensity produced by a disbond is detectable after a few seconds, it does not achieve a maximum value for about 10 s, and remains at a maximum value for about 15 to 30 s before it slowly decays over time. This decay by a disbond may last many minutes. Fluid ingress is detected and differentiated from a disbond or a delamination, because it produces a negative IR peak. The IR intensity produced by fluid in the honeycomb behaves similarly to a disbond, but with negative intensity. The measurement can also identify the presence of previous repairs to the composite and defects that occur in previously repaired areas.

Figure 37:
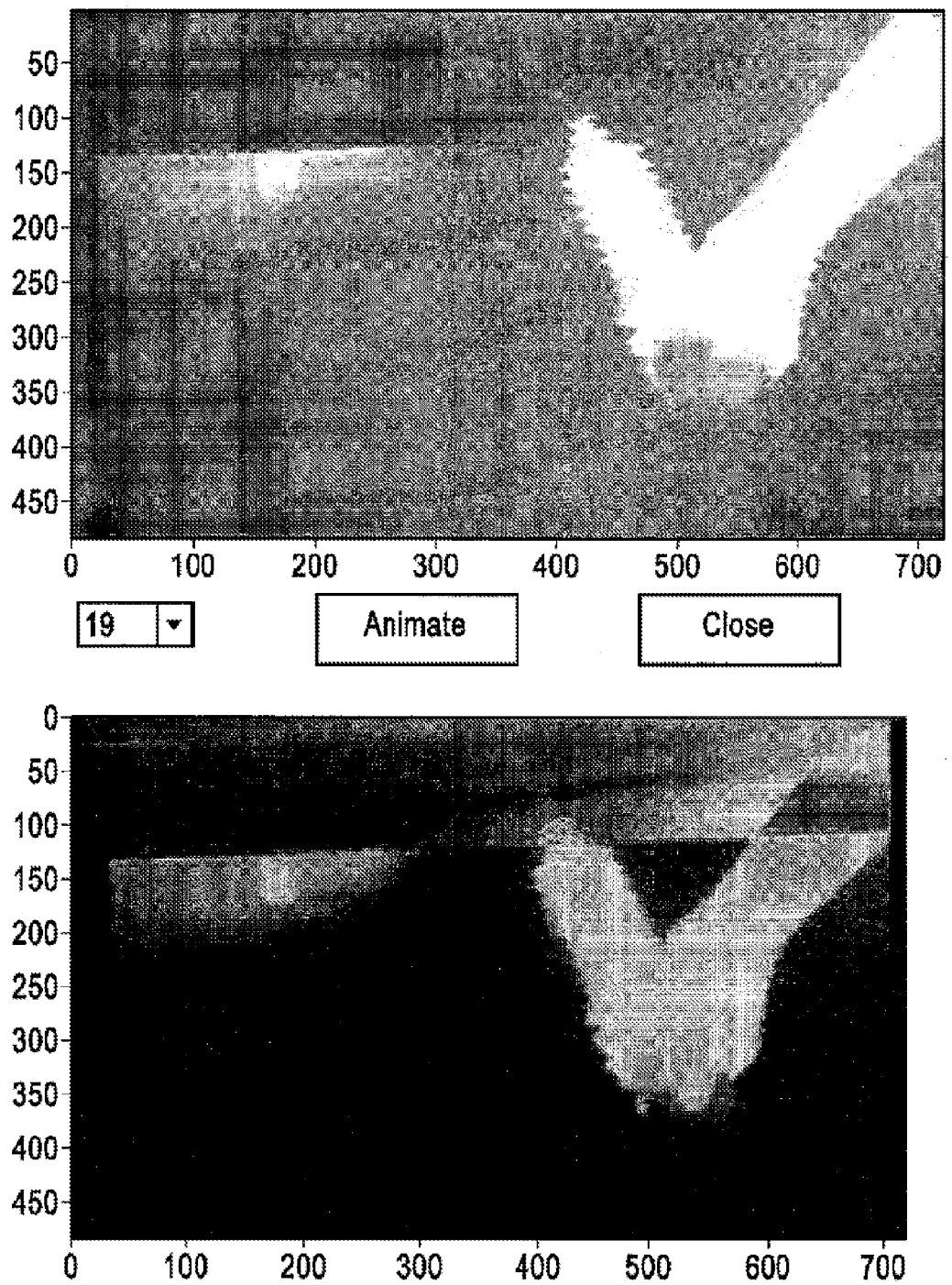
FIG. 37 illustrates the detection of the pull-tab on the prepared test article using a heating method.

FIG. 37 shows the results of a test conducted by moving a hot air blower with a diffuser over the surface of the rudder section beginning on the top and moving towards the bottom. The IR signature from the 0.5-in.-wide, 1.5-in.-long disbond is easily seen in the IR image and the noise compensated (Analyzed Image).

The following defects are visible in FIG. 36: (1) a large irregularly shaped skin-to-core disbond (MC12) with dimensions as small as 0.5 in. (arms) and as large as 3.1 in.; (2) a 0.5-in.-diameter skin-to-core disbond located in a repaired area (MC13); (3) two circular regions of fluid ingress (i.e., water in the honeycomb) (FI3 with a diameter of 2.0 in. and FI4 with a diameter of 1.0 in.) represented by the dark areas (cooler than the undamaged sections of the composite); (4) a pull tab disbond (PT42) with dimensions of 0.5 in. wide and 1.0 in. long with a 0.5-in. diameter fluid ingress defect (FI5) located beneath the pull tab disbond. All of the disbonds (and delaminations are represented by the white regions (hotter than the undamaged sections of the composite). As illustrated in FIG. 37 using another method of heating, the IR signature of the Pull Tab disbond was very strong and very distinctive in the video and IR images during the first 5 to 15 s of heating. However, its IR signature has faded over time and is difficult to see in the FIG. 36 because this IR image was produced after several minutes of heating. As stated above, disbonds (and delaminations) can be distinguished from regions of fluid ingress because the IR intensity is hotter (i.e., whiter) than the background for the disbonds and cooler (i.e., darker) than the background for the fluid ingress.

Example of Depot Test Results.

The system was used to collect data on the vertical stabilizer of an F-15 with markings from a previous inspection that indicated extensive damage on the top 12 in. of one the two Vertical Stabilizers. A portable, handheld camera frame was assembled to position the IR camera and to make the IR measurements. The prototype system used to collect data was easy and quick to use and functioned properly for the entire 3-day test period. The damage was located on both side of the stabilizer. Field measurements indicated the presence of a large number of disbonds (indicating a separation between the boron composite and the honeycomb structure) that coincided with the grid markings on the stabilizer. No damage was found in the other regions of the stabilizer below the top 12 in. and no damage was found on either side of the other vertical stabilizer. Measurements on the damaged section were made on 10 June and showed the same results when repeated two days later. Data were also collected near the bottom and on the thickest section of one of the vertical stabilizers. Over 80 tests were conducted on the two vertical stabilizers in both the damaged and undamaged regions.

In addition to the data collected on the F-15 at the depot, data were also collected at the inspection facility on various sections of a vertical stabilizer cut into 5 sections with known and identifiable damage. Data were also collected on a speed brake with known damage to demonstrate that the method can be used to locate defects in other types of composites besides boron composites. The same method used for the boron composites found on the vertical stabilizer worked equally carbon composites found on the speed brake.

The three days of testing provided the opportunity to evaluate the performance and functionality of the system under actual inspection conditions on an F-15 at the depot and on previously damaged sections of the F-15 in storage at the inspection facility. This was the first time that the system was used on an F-15, and it performed well, identifying defects where defects were known to be present and not finding defects where no damage existed.

The three days of testing provided the opportunity to evaluate the performance and functionality of the technology using an Engineering Prototype under the following conditions: (1) thin and thick composites found at the top and bottom of the vertical stabilizer; (2) damaged and undamaged sections of the Vertical Stabilizers of an F-15 aircraft and on damaged aircraft sections taken out of service for inspection; (3) different types of defects (disbonds, delamination, and fluid ingress); (4) different types of composite materials (boron and carbon); (5) actual depot inspection conditions during very hot air temperature conditions (>95° F.); and (6) for different heating times (10 s and 20 s).

Figure 38:
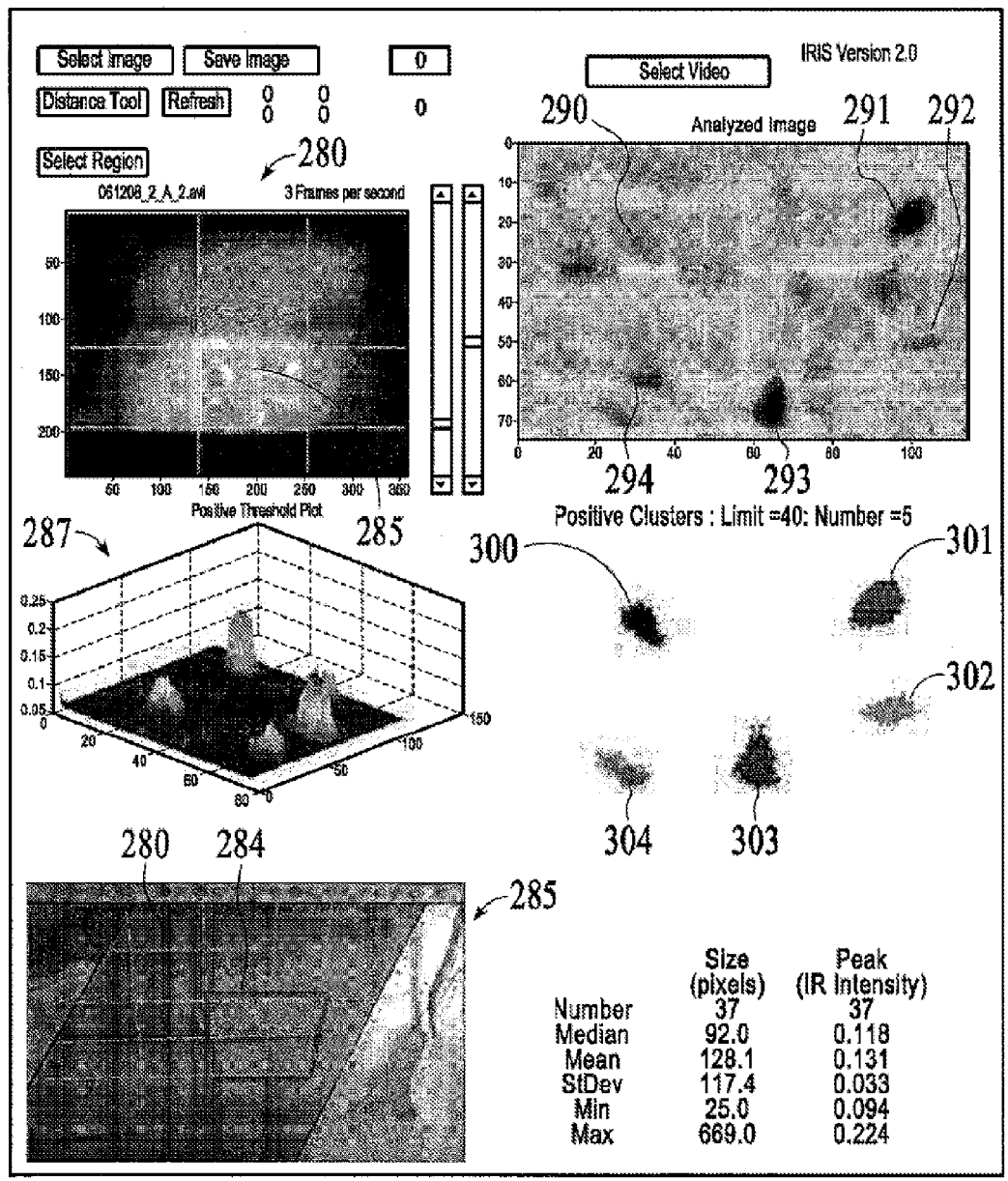
FIG. 38 illustrates the results of disbonds present on the top of the vertical stabilizer of the F-15, the IR image, the processed contour map, the 3D threshold exceedance map, and the cluster map.

FIG. 38 shows one side of the vertical stabilizer where damage had been previously detected. For clarity, only the results from the black-marked area are shown. FIG. 38 also illustrates the presence of at least 5 large disbonds in the darkened region, and the possibility of two smaller disbonds. The upper left IR image shows the region analyzed in the IR image. The top figure on the right shows the noise compensated (Analyzed Image) region and the two middle figures show the number and amplitude of the pixels exceeding the threshold. (A pixel is 1/16 in. by 1/16 in.).

Composite materials such as boron, Kevlar, graphite, and carbon materials are widely used in many advanced aerospace structural systems [4-6]. Reliable damage assessment for these structures, which are subject to wear and tear, including extreme operational conditions, is one of the most serious and costly problems faced in field of depot maintenance. This problem is compounded by the fact that damage can occur in many different forms.

Damage in composites can be detected in numerous ways, but the conventional detection methods are frequently limited to certain kinds of materials and structural geometries, and they are usually weak at quantifying the damage. In addition, these methods often require the structure to be at least partially disassembled so that a skilled technician can interpret the observations. This increases the labor costs and adds to the time needed to complete the inspection. This proposal should and will address defect signature analysis with a view to implementing an automated defect identification, extraction, and classification methodology (e.g., disbonds, water penetration, and delamination) that will ensure minimum operator intervention. The operator will only be needed to verify the present of a defect by inspecting the IR video images manually that are processed in real time.

The specific inspection problem is to detect disbonding between the boron composite and the aluminum honeycomb structure in the F-15 Vertical Stabilizer. Such disbonding, if large enough, could produce structural failure. It was explained that water penetration or water ingress into the honeycomb structure is also important, because it may be a precursor of future potential disbonding. While honeycomb is a "good structure" that offers a high strength-to-weight ratio, over time, water has a way of working its way inside the structure, leading to corrosion and component disbonding. Furthermore, it would be highly desirable to be able to identify and then distinguish between the disbonding defects and the water ingress defects. As a goal, the COTR indicated that the inspection system should be able to detect such disbonding if it covers a surface area of a 0.5-in. diameter circle, or larger, because such disbonds may produce damage. Delamination between the boron layers is a lower priority objective because it does not pose the significant structural risk of disbonding. As will be described below, while all three of these types of defects were detected experimentally in the Test Article provided by the USAF during Phase I, particular attention and development was focused on disbonding and fluid ingress defects. Experimental measurements showed that the IR signature produced by a disbond is significantly different than the one produced by fluid ingress and identifiable. Thus, detection, identification and classification is possible. Because the IR signals were so unique, an automated signal processing algorithm can be developed and implemented.

Disbond in a Thick Composite Panel.

Figure 39A:
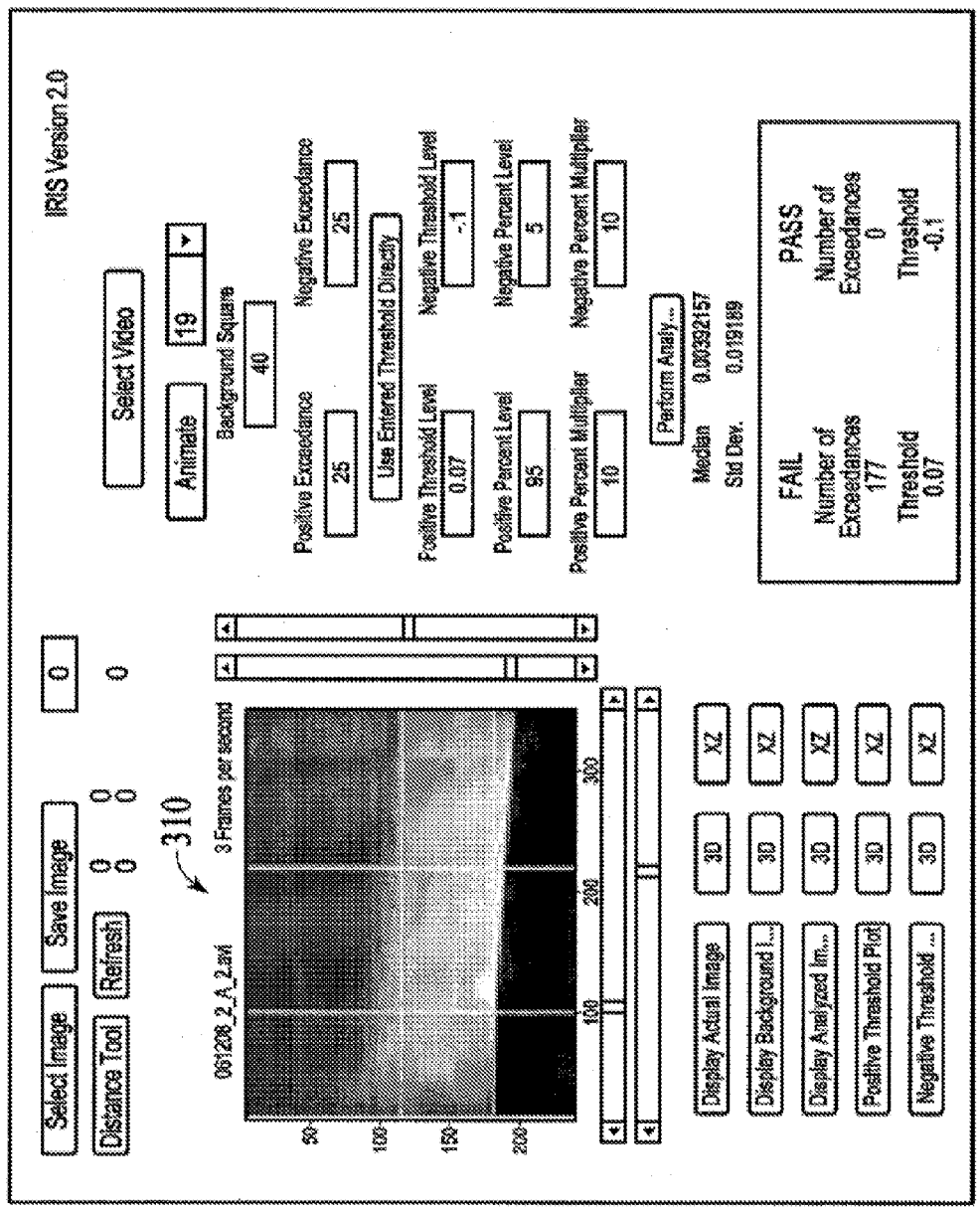
FIG. 39A illustrate the detection of a disbond that is located near the bottom of the stabilizer, which has a very thick composite comprised of about 50 layers of boron vice 6 to 9 near the top.
Figure 39B:
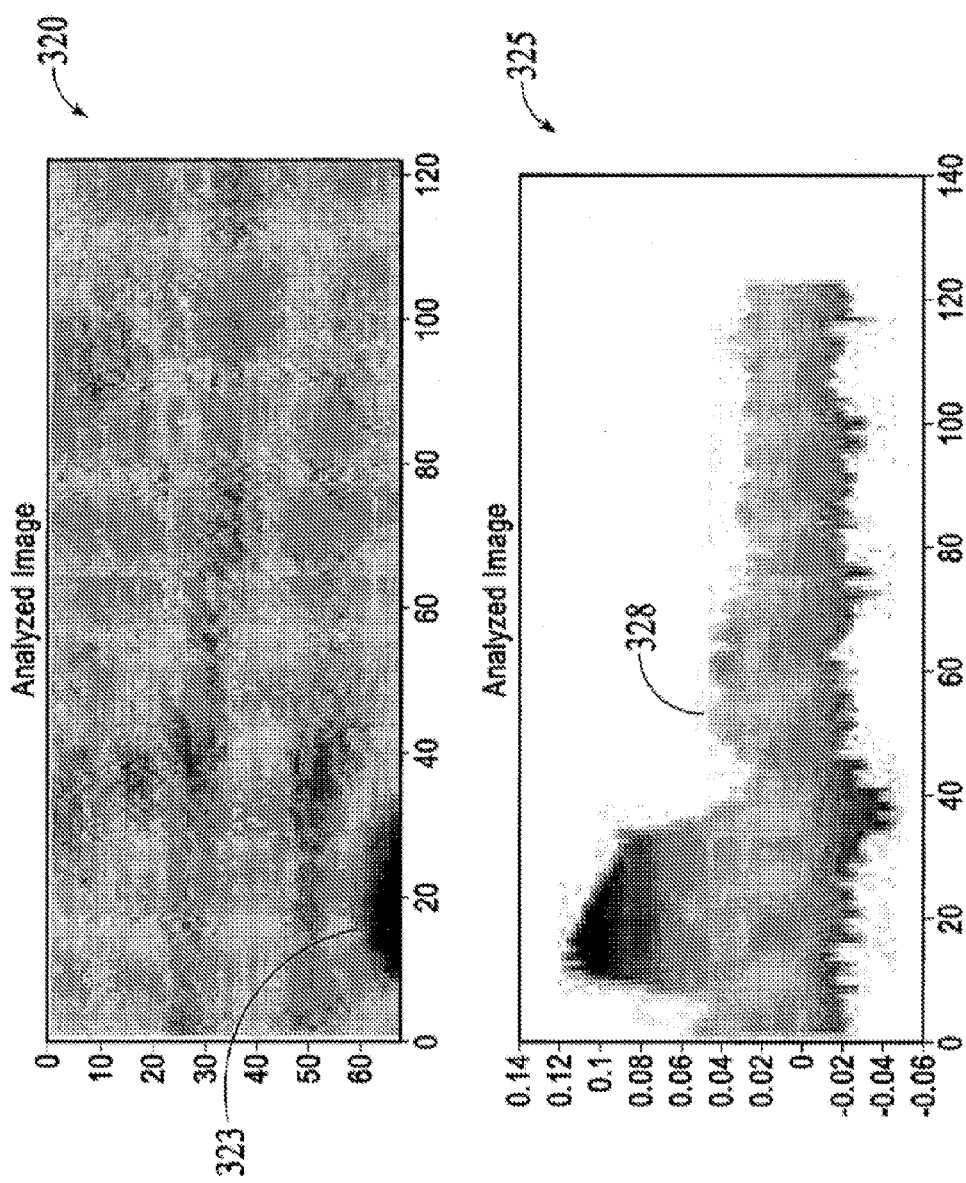
FIG. 39B illustrates the image and noise of a test conducted in the lower portion of the vertical stabilizer. The noise spread is +0.12 to −0.06.

During testing in the Inspection Facility, a disbond was created in the thickest section of a disassembled vertical stabilizer using a razor blade. The blade was inserted about 1 in. into the section. The thickness of the disbond was less than 1/32 in. As illustrated in FIGS. 39A and 39B, the disbond was readily detected.

Carbon Composites.

In addition, to the F-15 data collections, IR measurements were made damaged sections of a vertical stabilizer and a speed brake. The speed brake measurements were important, because it demonstrated that the IRIS can detect defects in other types of composites besides boron. This was the first test on carbon composite and the system performed as expected and similarly to that on boron composites.

Delaminations and Disbonds on a Vertical Stabilizer.

Figure 40A:
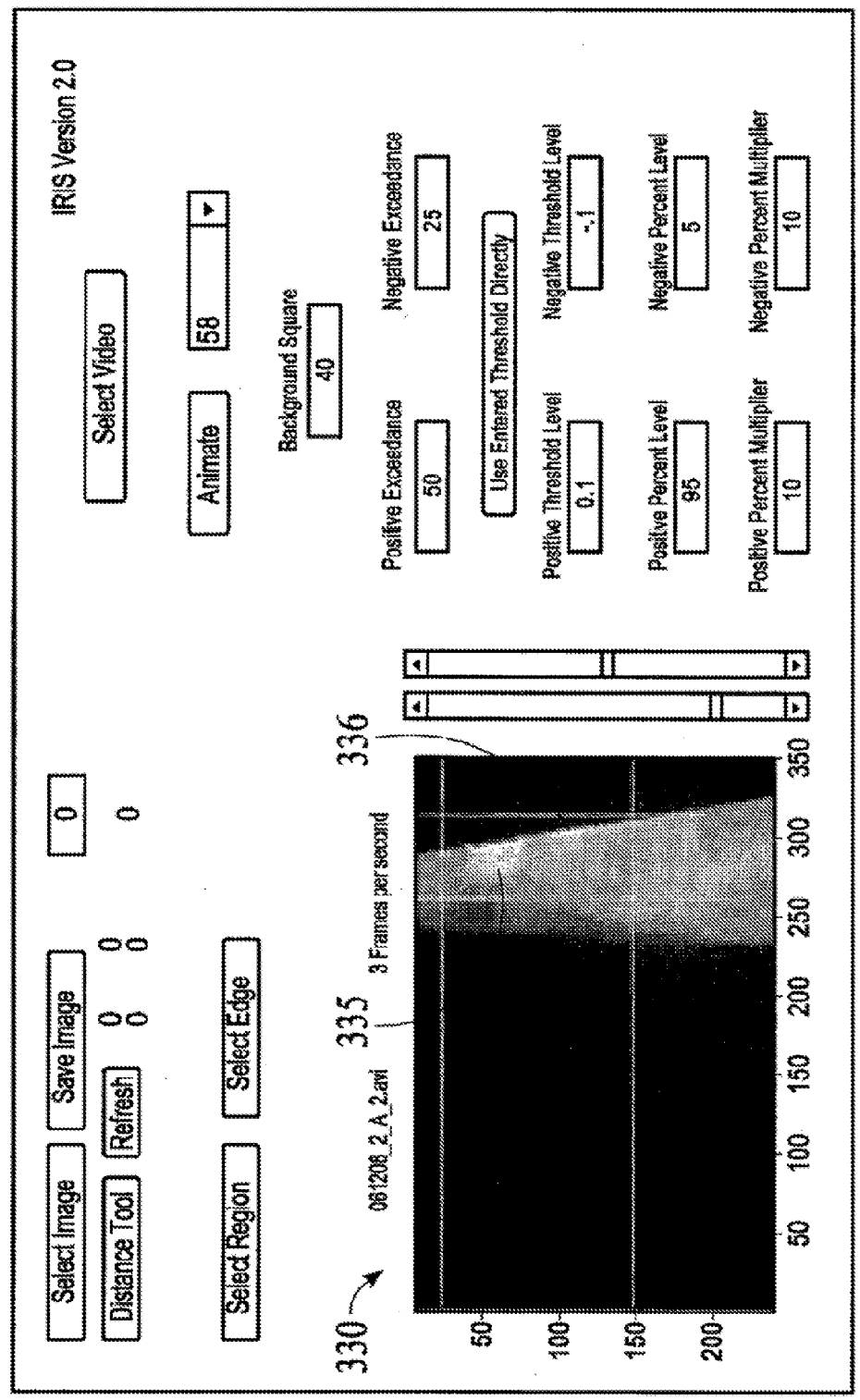
FIG. 40A illustrates the detection of both a delamination and a disbond in a single measurement.
Figure 40B:
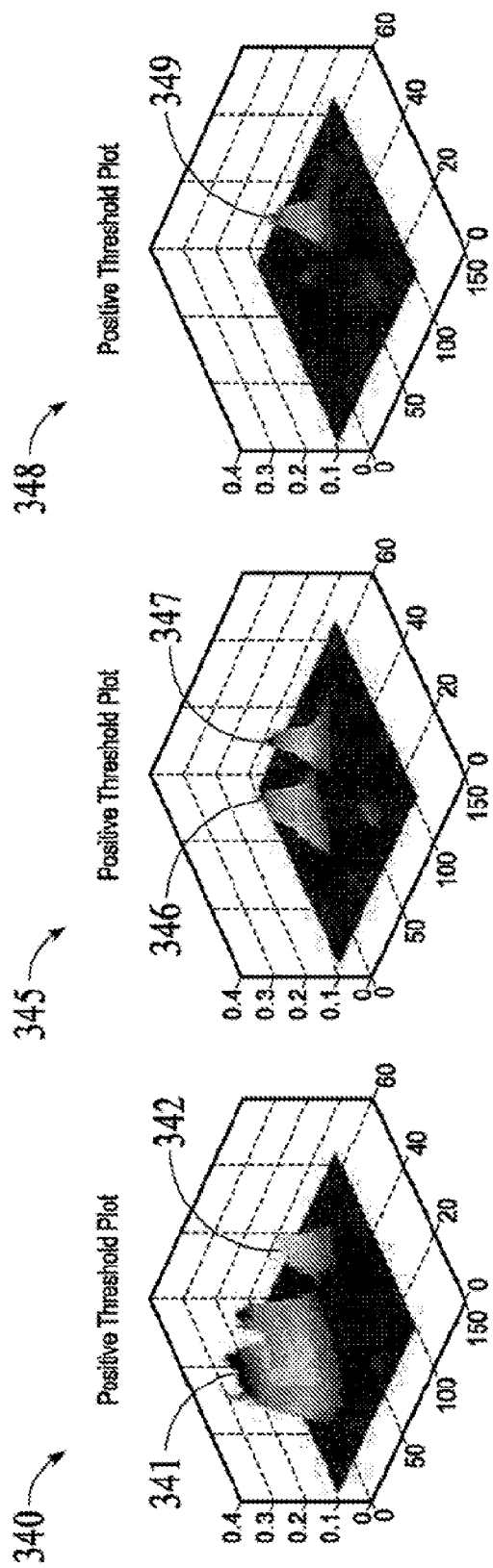
FIG. 40B illustrates contour maps showing the detection of both a delamination and a disbond in a single measurement.

A full vertical stabilizer with known damage was removed from an F-15 and cut into five sections for NDT analysis at Robins AFB. All five of the sections were inspected using the IRIS system. The results of the inspection for one of the sections are shown in FIGS. 40A and 40B. This figure shows the presence of a large delamination, about 1 in. wide by 3 in. long, and a disbond between the boron composite and the honeycomb, about 1 in. wide by 1 in. long, and located about 2.5 in. below the delamination. This inspection illustrated the temporal differences in the characteristics of these two defects as a function of the initial appearance after removing the heater and the persistence and decay of the IR intensity over time. FIGS. 40A and 40B shows the presence of the delamination approximately 1 s after removing the heat source. The top plot is the noise compensated plot and the bottom plot is the positive threshold (+0.07). The two adjacent plots are for 4 s and 10 s after removing the heater. After 10 s, a very weak disbond signal begins to appear. As illustrated in FIGS. 40A and 40B, after 26 s, the size and strength of the delamination signal and the disbond signal are about equal. After 38 s, the delamination signal is no longer detectable (FIGS. 40A and 40B). The disbond signal remains strong and has the same IR intensity as at 26 s. This analysis is significant, because it clearly suggests a measurement and processing approach for detecting and classifying delamination defects and disbond defects.

Distinguishing Water Ingress from Epoxy.

The method and a handheld apparatus were used to detect and differentiate water in aluminum honeycomb aircraft structures from a buildup of epoxy in the aluminum honeycomb. The method requires two 30-s IRIS measurements, one on each side of the composite (FIG. 1).

Figure 41:
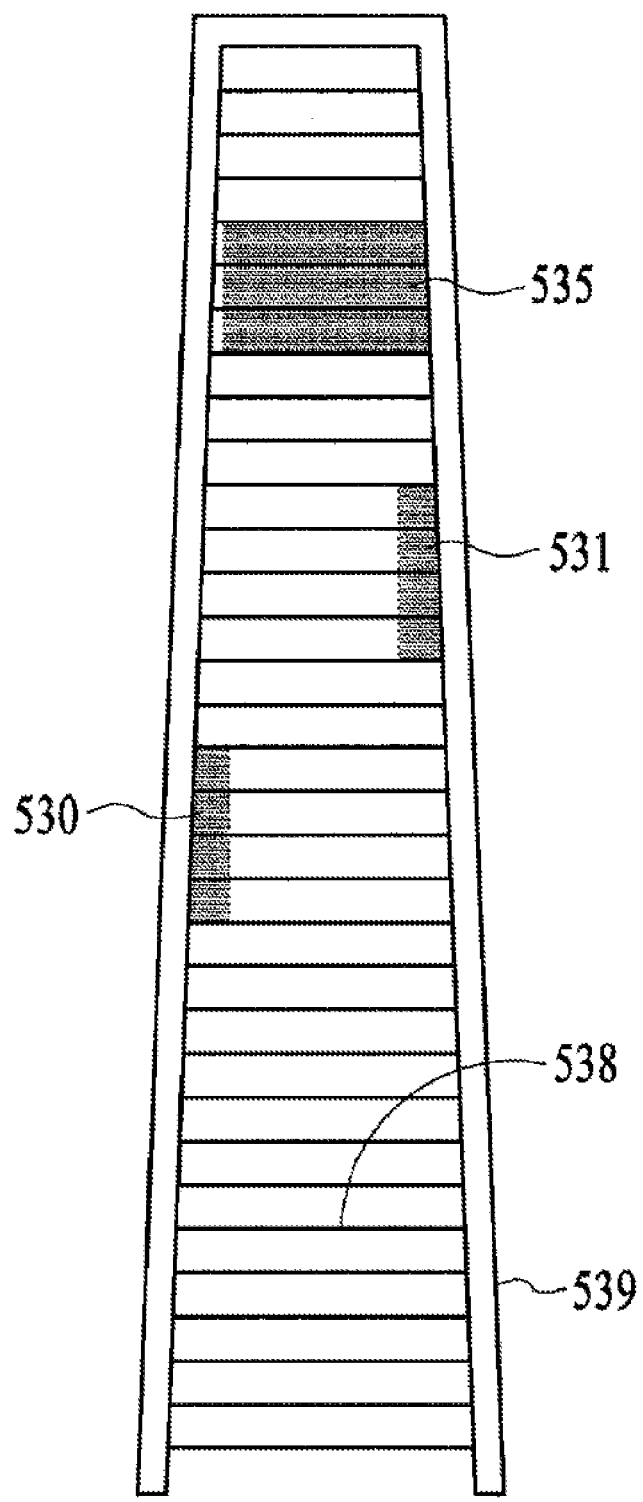
FIG. 41 illustrates the situation of fluid within the honeycomb structure compared to a build-up of epoxy between the honeycomb and the composite skin.
Figure 42:
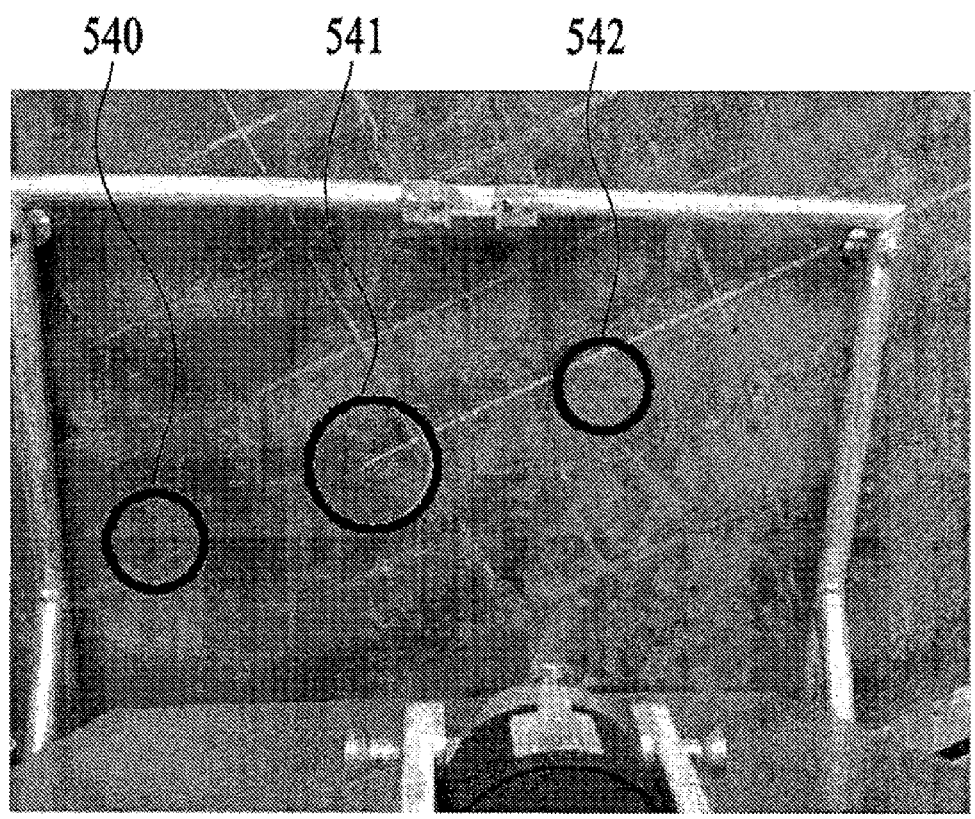
FIG. 42 illustrates the F-15 Vertical Stabilizer being inspected for Water, Epoxy, and No Epoxy on the inside surface of the honeycomb touching the underside of the boron composite.
Figure 43:
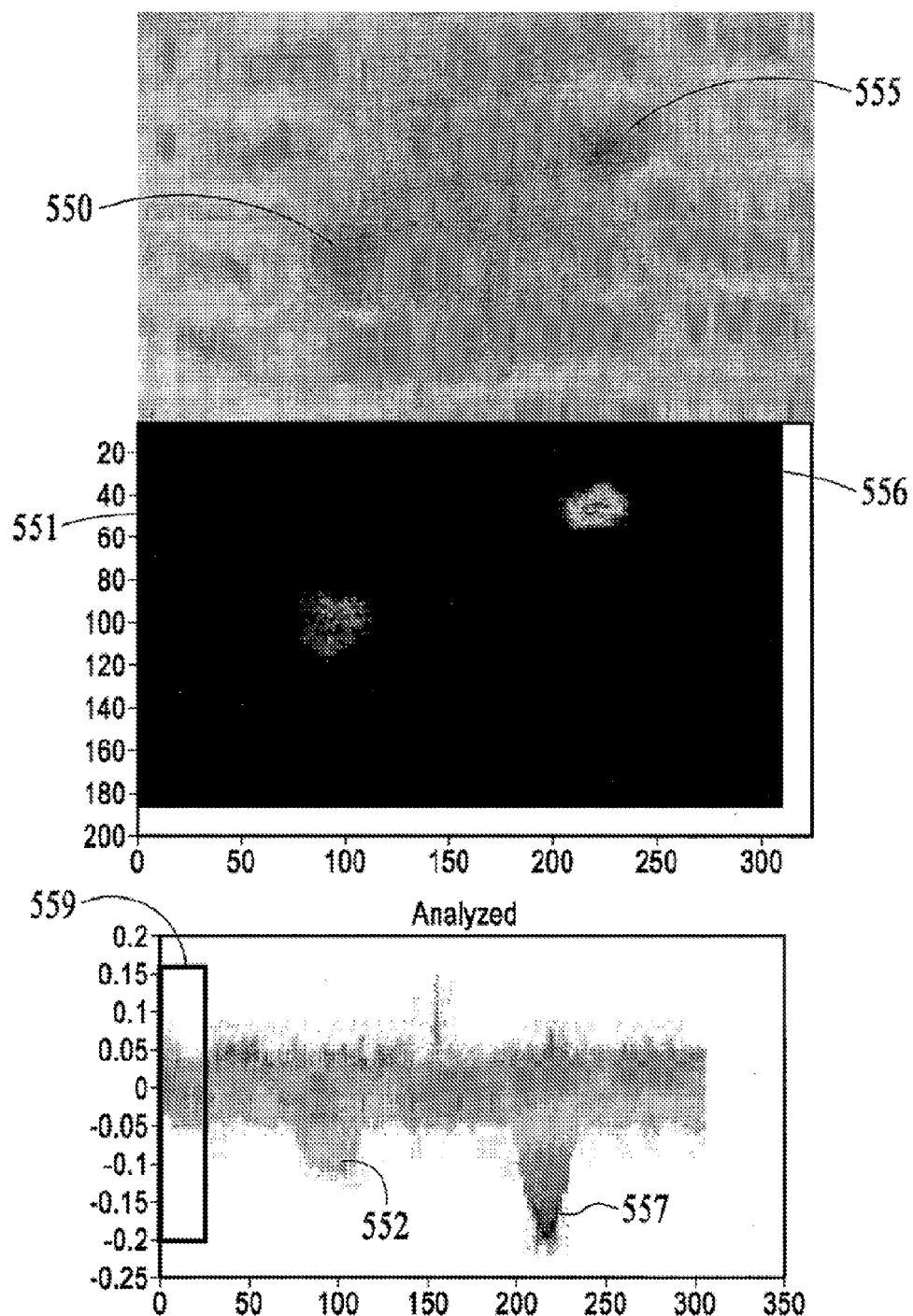
FIG. 43 illustrates the IR Inspection Test on Side 1 17 s after removing the heating mat. The top image is the raw IR image, the middle image is after noise cancellation, and the bottom is the vertical profile to show the signal strength.

FIGS. 41 and 42 illustrate the detection problem. Water and epoxy have very similar thermal properties, and therefore, they have very similar IR responses when in contact with the underside of the composite being heated. For most epoxies, however, water has a stronger IR response by about 50% (as illustrated in FIG. 43). However, as can be seen in FIG. 43, they both produce strong and easily detectable IR signals during the cooling period after heating the composite for 15-s (or longer) and removing the heat source. The preferred embodiment of the present invention can distinguish water from epoxy by performing a test on both sides of the composite and comparing the results. The water will be present on both sides, but the epoxy will be present only on one side. Thus, Epoxy 2 (as shown in FIG. 41) will not be observed when inspecting Side 1, and Epoxy 1 will not be observed when inspecting Side 2, but the water will be observed on both sides.

If water is found in the honeycomb structure, then, as illustrated schematically in FIG. 41, it can and it will contact the composite surface on both sides of the honeycomb structure when placed in vertical position for testing. Epoxy, on the other hand, is usually found only on one side of the honeycomb structure as a buildup of epoxy (e.g., ¼ in.) during fabrication or subsequent repair. The IR signal produced by the water is maximized when the honeycomb is filled with water, or when the structure is tipped slightly to allow the water to accumulate on the side of the composite being inspected. Tipping the structure, however, does not affect the strength of the epoxy signal.

FIG. 42 illustrates a demonstration of the test setup to demonstrate the capability of the IRIS for differentiating epoxy from water. The measurement was set up similar to Side 1 of FIG. 41. The inspection on both sides of the stabilizer can be simulated using this configuration. The capability will be validated if the IR system detects the water and Epoxy 1 on Side 1, but does not detect the Epoxy 2 when inspecting Side 1.

The Water, Epoxy 1 and Epoxy 2 were inserted into the F-15 Vertical Stabilizer in the middle section where the number of composite plies was about 20 to 25 and the thickness of the stabilizer was about 3 inches. Epoxy 1 and Epoxy 2 were about ¼ in. thick and covered a circular area of about 1.5 in. in diameter. The epoxy was inserted into the honeycomb so that it touched only the inside surface of the composite on only one side of the stabilizer as illustrated in FIG. 41. Loctite Quickset 5 minute epoxy from the hardware store was used. Water was inserted into the honeycomb until it filled the honeycomb and touched the inside surface of the composite on both sides of the stabilizer. A number of tests were performed with different amounts of heating time ranging from 10 s to 60 s (10 s, 15 s, 20 s, 30 s, and 60 s), all with nearly identical results.

Figure 44:
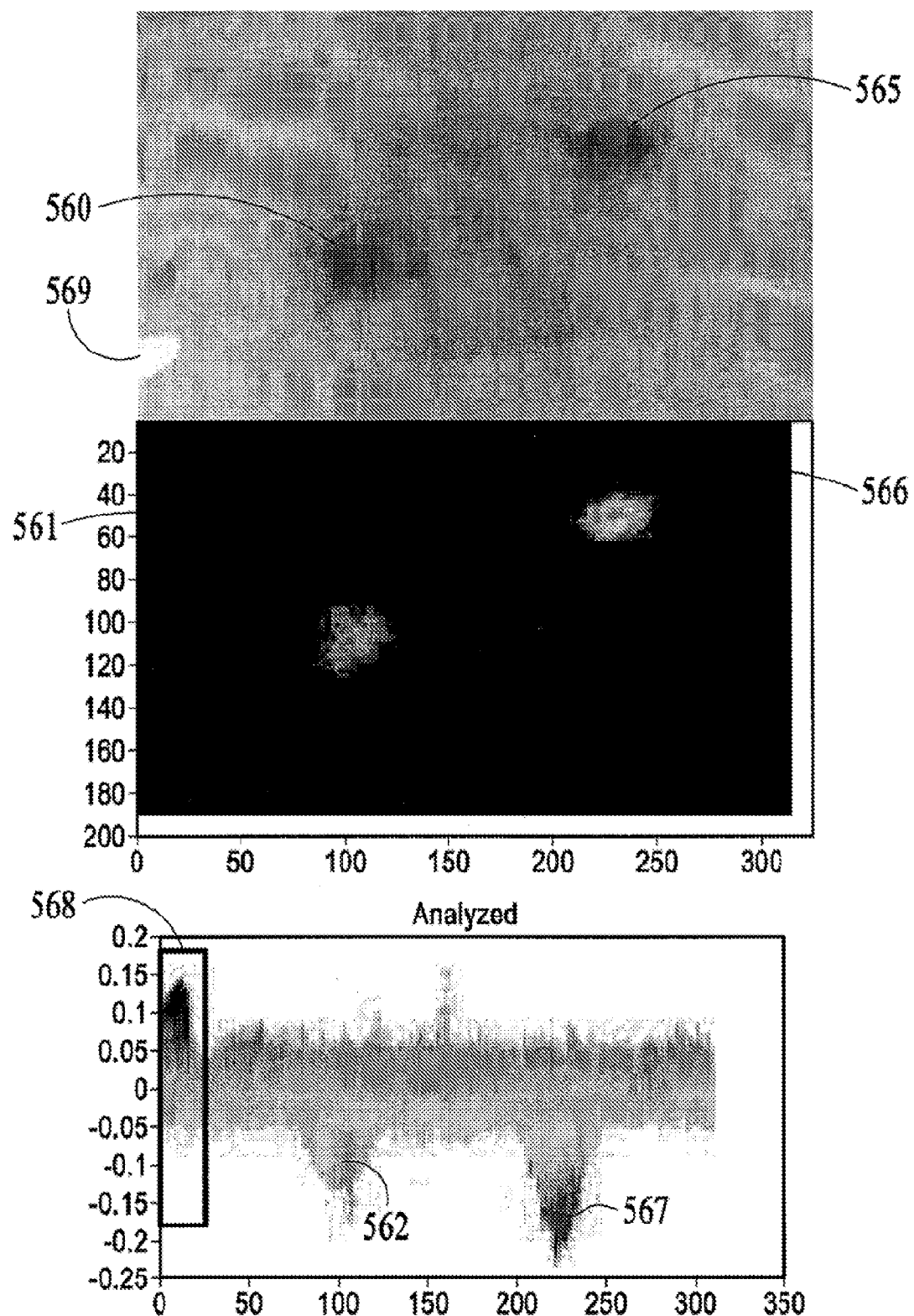
FIG. 44 illustrates the IR Inspection Test on Side 1 40 s after removing the heating mat. The top image is the raw IR image, the middle image is after noise cancellation, and the bottom is the vertical profile to show the signal strength.

FIG. 43 illustrates the results of the demonstration measurement about 17 s after heating the surface of the composite for 15 s (Total Time: 32 s). FIG. 44 illustrates the results after waiting another 23 s (Total Time: 55 s) with the operator's finger in the image showing the location of Epoxy 2 which was not and should not have been detected. Otherwise, both results are very similar. The top plot in each figure shows the raw IR image. The middle plot shows a two-dimensional contour-map view after applying the noise cancellation algorithm to the raw IR image and setting a negative threshold of 0.04. The bottom plot shows a vertical profile of the IR signals after noise compensation, because it best illustrates the strength of the detected defect signals. The IR intensity of the water is stronger than that of the epoxy, but both defects are easily detected.

In all three views, the Water and Epoxy 1 are detected and Epoxy 2 is not. This illustrates that unless the epoxy was on the side of the stabilizer being heated, it will not be detected. This allows the operator, after testing both sides of the stabilizer, to state that the detection on the right is Water and that Epoxy 1 is epoxy and is on Side 1 of the composite and Epoxy 2 is epoxy and is on Side 2 of the composite. The threshold used in the analysis results in a probability of detection ($P_D$)>99% and a probability of false alarm ($P_{FA}$) <1%. Similar results were obtained for all inspection times.

No modifications to the preferred embodiment are needed to implement this measurement. The operator needs to test the opposite side of the stabilizer whenever a negative IR intensity is detected to determine if the negative IR intensity was produced by Water or Epoxy.

Potentially Damaged Honeycomb Boron Composite Aircraft Sections.

The method of the present invention was used to inspect potentially damaged aircraft sections after undergoing x-ray inspection and coin tap testing. More than 35 measurements were conducted on the F-15 horizontal stabilizer and rudder pieces that had been recently inspected (some within 24 h). The three main results that came out of the demonstration were The IRIS confirmed fluid ingress detected by a different method (in this case, X-ray) within the honeycomb structure;

The IRIS was able to determine the relative amount of liquid detected; and

The confirmation or denial of internal structural damage detected by alternate inspection methods.

The x-ray and coin tap test methods showed regions of suspected fluid ingress and other damage. X-ray methods, which see through the entire structure (i.e., both sides of the structure), can be used to inspect the structure for fluid ingress and for cracks, but not disbonds and delaminations. Coin tap methods can be used to inspect the structure for disbonds and delaminations, but not beneath previously repaired areas. The IRIS can be used to detect the presence of all of these defects, and on both sides of the structure, both inside and outside of repaired areas. The first set of IRIS measurements focused on the x-ray inspections, which showed the presence of small amounts of fluid in the honeycomb. As part of these IRIS measurements, the presence or absence of disbonds and delaminations, both in and outside of the repaired areas, were also checked.

The first objective was to confirm the presence of moisture in the honeycomb. If moisture was present vice being a local buildup of epoxy, then determine if it was large enough to be a problem. The x-ray measurements suggested that the amount of fluid was small. The IRIS method detects fluid against the internal composite surface as well as larger amounts of fluid that may fill or partially fill one or more of the honeycombs. It also differentiates fluid from a local buildup of epoxy. Fluid in the honeycomb is differentiated from an epoxy buildup by inspecting both sides of the aircraft composite when the aircraft part is in the vertical position (i.e., honeycomb is running parallel to the ground). If fluid is detected on both sides of the structure (i.e., the volume of fluid is large enough to fill or partially fill the internal honeycomb so that it is in contact with both sides of the structure), then it can be concluded that fluid is present. In this case, the IRIS measurements clearly showed that the volume of fluid was too small to fill or partially fill the honeycomb, because it was detected only on one side of the structure. If the fluid is detected on only one side, then it can be a very small amount of fluid or a buildup of epoxy. There are a number of ways to differentiate between the two, but in general, if it were fluid, it would be too small to be a problem. This was checked by tilting the structure toward and away from the test surface and making IRIS measurements on both sides of the structure. If small amounts of fluid were present, it would flow to the downhill side of the structure, contact only the downhill side, and the IRIS would only detect its presence on the downhill side. This was indeed the case. The tilting confirmed the presence of water (versus an epoxy buildup) and the fact that the amount of water was small. If the "fluid" had only been detected on the uphill side after tilting the structure both ways, it could be assumed that the detection was a local buildup of epoxy. Strictly speaking, the detection could still be a very small amount of fluid, too small to flow downhill. If further investigation were warranted, the IRIS could be used to differentiate fluid from epoxy from its temporal characteristics. However, as stated above, further measurements are probably unnecessary, because if it were fluid and not epoxy, it would be too small to be of practical concern.

Figure 45:
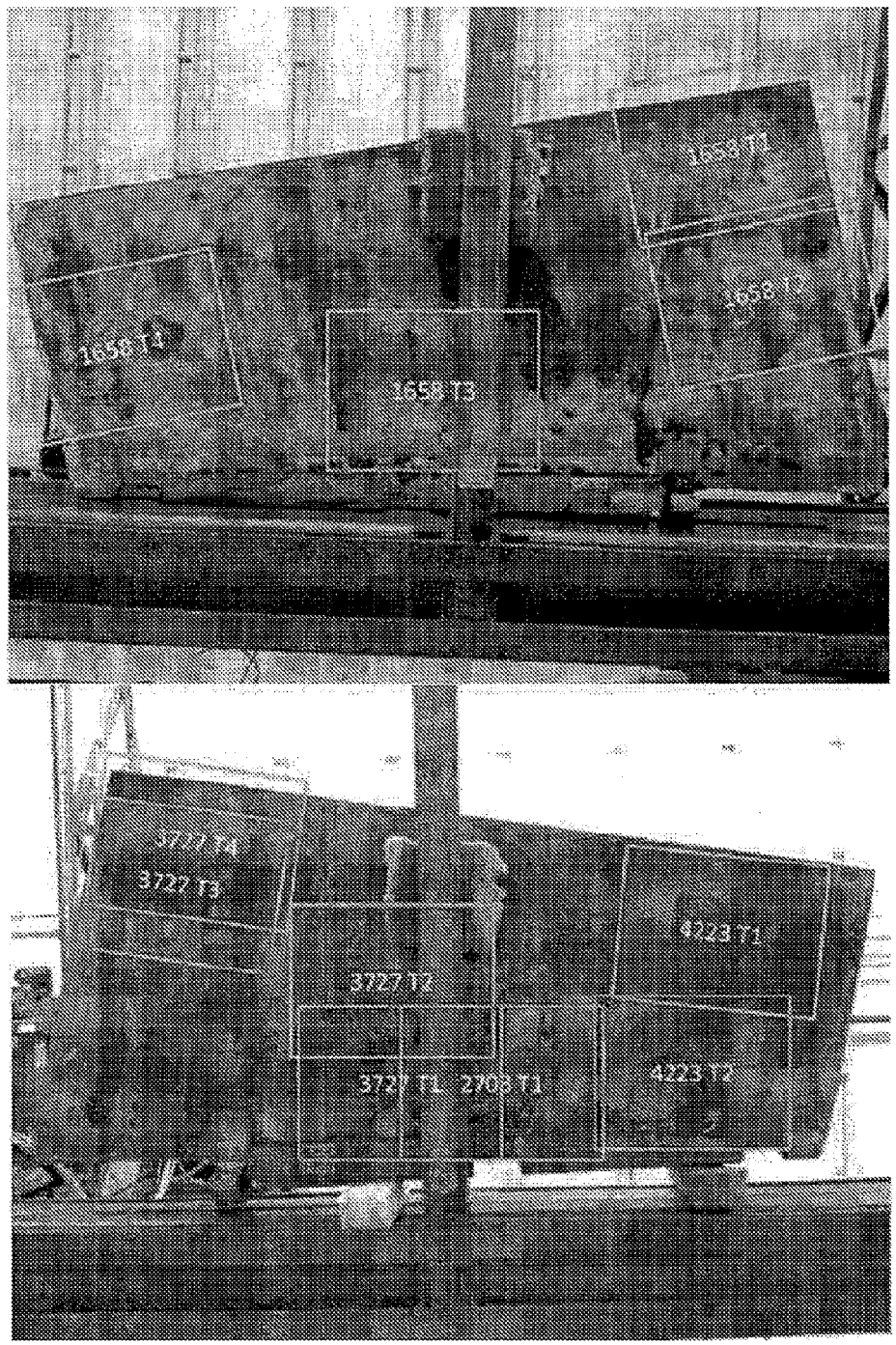
FIG. 45 illustrates the IRIS measurement locations on both sides of the rudder. IRIS measurements were conducted at locations of suspected damage.

The IRIS method detects and differentiates damage internal to the structure (i.e. disbonds) from damage at the surface (i.e. delaminations and nicks or scratches) based on the thermal signature produced by each. Testing was conducted on a rudder with numerous surface markings indicating possible damage. FIG. 45 shows the locations of measurements conducted on the rudder. Many of the surface marks indicated a surface patch or a repaired region of the rudder. The IRIS measurements were able to show that there were no disbonds at the patches or repaired areas.

Figure 46:
FIG. 46 illustrates the region of a rudder tested for fluid ingress. The black oval shows the location of suspected fluid ingress.
Figure 47:
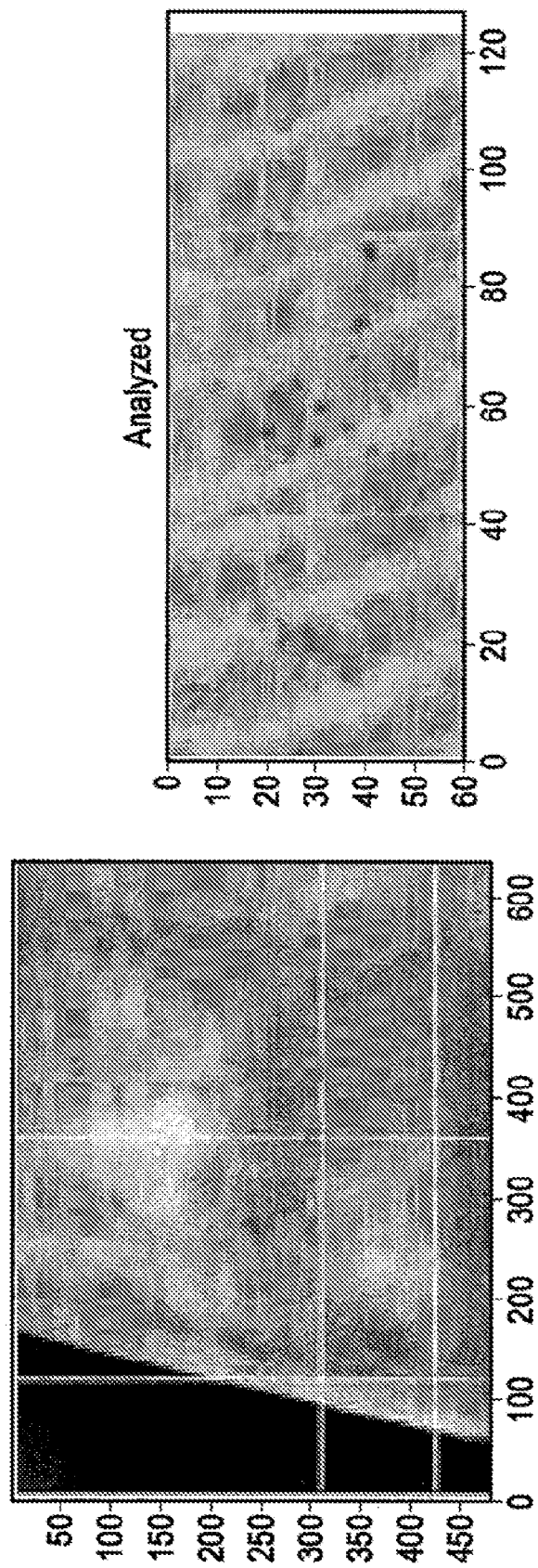
FIG. 47 illustrates the results of IRIS measurement taken of a region of suspected fluid ingress. The region within the white cursors was analyzed and the results are shown on the right. The dark regions indicate fluid or other material within the structure.

IRIS testing was conducted on a region of a rudder where x-ray testing showed fluid ingress. The x-ray results showed a few honeycombs with very small amounts of fluid at the leading edge of the piece (<5% of the honeycomb cross-sectional area). An IRIS measurement was conducted in this region to confirm the presence of fluid. The test article was in the vertical position for the initial testing. See FIG. 46. The black oval shows the location of suspected fluid ingress. The IRIS detected regions of possible fluid (darker or cooler regions) at the location indicated by the x-ray. This measurement is shown in FIG. 47. The area outlined by the cursors was processed using the background cancellation algorithms. The image on the right shows the processed results. Fluid or other material was detected and is indicated by the dark regions in the processed image. The location and pattern of the dark regions matches the x-ray results.

Figure 48:
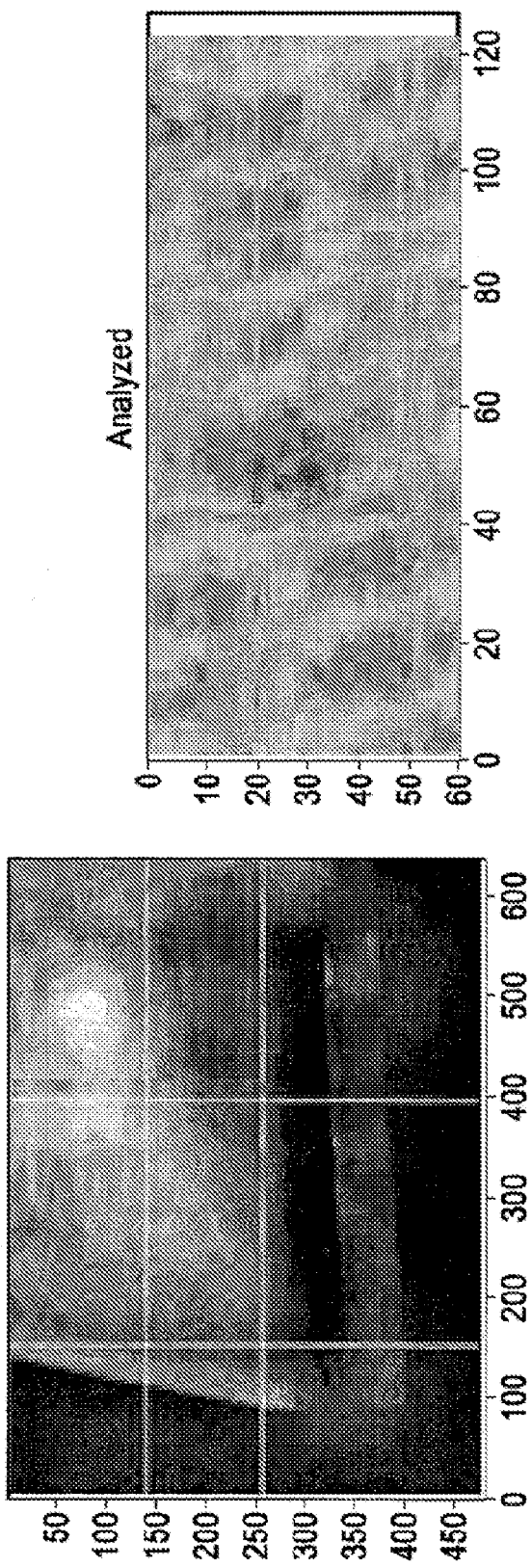
FIG. 48 illustrates the results of IRIS measurement taken of a region of suspected fluid ingress with the rudder tilted away from the surface being inspected. The region within the white cursors was analyzed and the results are shown on the right.

Initial tests with the IRIS on the other side of the rudder in the same location did not show the fluid ingress, indicating that the detection on the first side may be epoxy or a very small amount of fluid. The rudder was then tilted away from the side of the initial tests and the location was tested again. FIG. 48 shows the results of the IRIS measurement with the rudder tilted away from the test surface. In this position, the IRIS method did not detect the fluid indicated by the X-ray testing, which indicated that the signal was due to fluid and not epoxy as the fluid moved downhill toward the opposite side. The analyzed image to the right in FIG. 48 does not show the darker cooler regions of fluid. This indicates that the material within the honeycomb is indeed a fluid. It also indicates that the volume of fluid is small, because it did not contact both internal sides of the rudder simultaneously.

Figure 49:
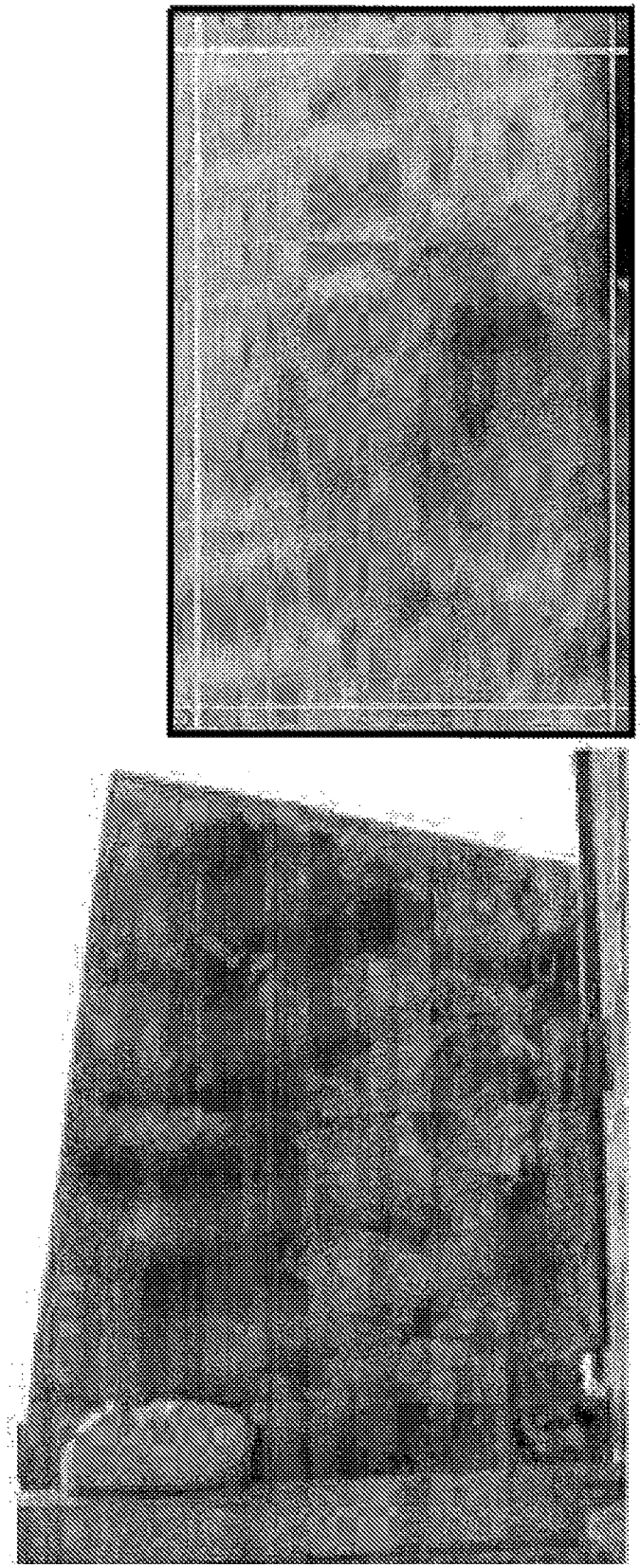
FIG. 49 illustrates an IRIS measurement on a repair of an F-15 Rudder.

The IRIS may also be used to confirm the integrity of a patch or repair. X-ray inspection methods can locate a repair within the rudder, but this method is not able to determine the status of the adhesion between the honeycomb and composite surface. The IRIS detects disbonds between the honeycomb and composite surface, which appear as bright or hot spots on the IR image. The IRIS measurement on the rudder at the repair clearly shows the repaired region, but does not indicate any disbonds or delaminations because no bright or hot spots are visible. This measurement shows good adhesion at the repair. See FIG. 49.

Detection of Fluid Ingress and Disbonds in Aluminum Skin-Aluminum Honeycomb Structure.

Figure 51:
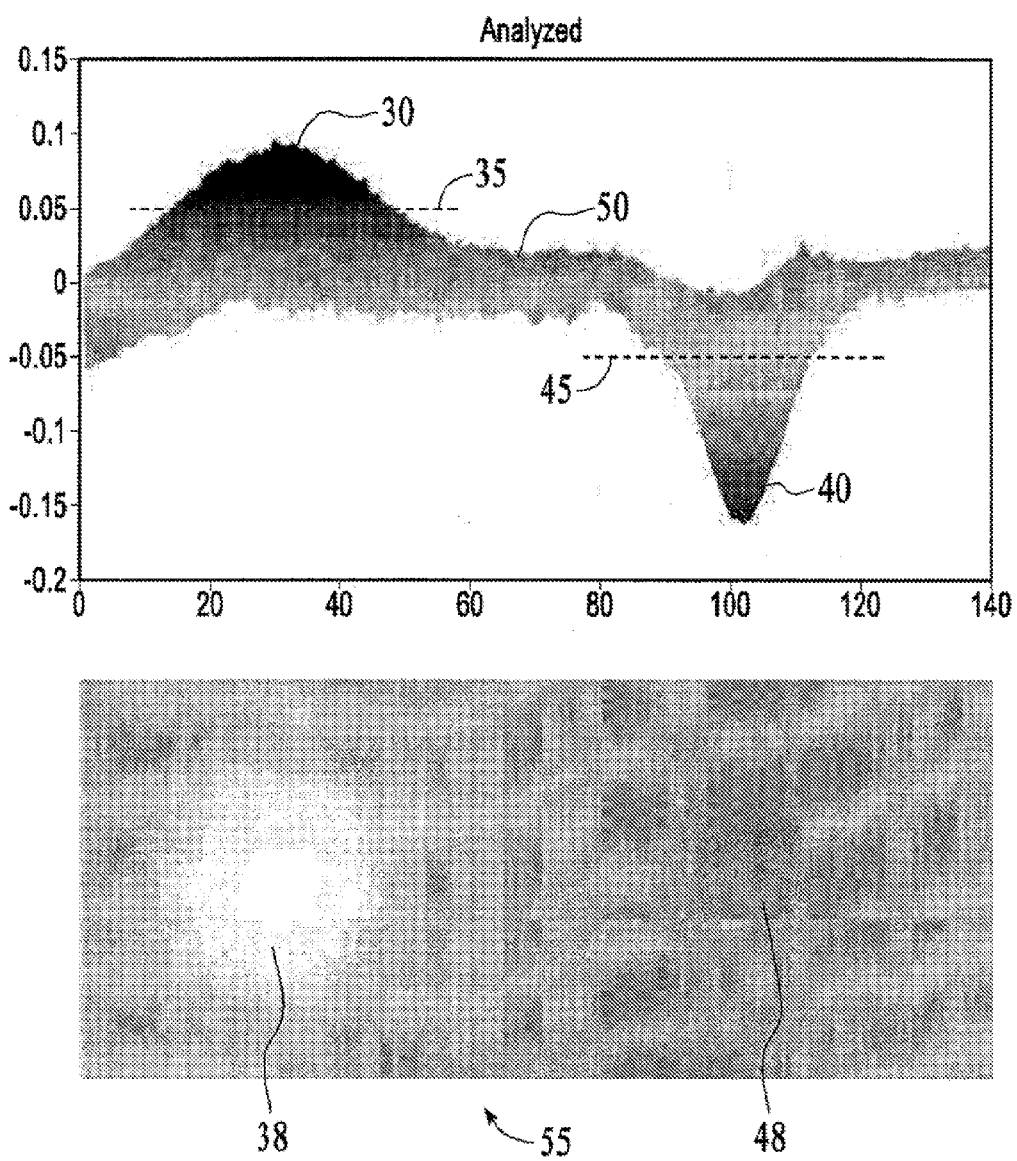
FIG. 51 illustrates the difference between a disbond and delamination, which are warm, light intensity and positive signals in processing, and fluid ingress like water or lubricant, which are cool, dark intensity and negative signals in processing.

The preferred embodiment of the present invention can be used to detect and locate disbonds in Aluminum Skin-Aluminum Honeycomb aircraft structures like those found on the C5A wing tip. Both water and/or lubricant, which may seep into the honeycomb structure itself, can also be detected and located. FIG. 51 illustrates the positive response expected for disbonds and the negative response expected for water. The measurements further indicate that the regions of water can be distinguished from regions of lubricant, and both types of fluid ingress can be easily distinguished from disbonds. Two sets of demonstrations were performed.

The first set of tests was performed on a test sample in the laboratory. The disbond was created by inserting a thin blade (0.5 in. wide by 1.5 in. long) into the end of a section of aircraft to create a disbond between the aluminum honeycomb and the aluminum skin. While these tests demonstrated the feasibility of the methods, it was not as convincing as it could have been because of the location of the disbond in the side of the sample. The tests were repeated with disbonds located in the center of the test sample, because they are more representative of the type of defects that might occur.

The results are presented below. Three methods of changing the temperature of the structure were demonstrated. The first was the conductive heating mat of the preferred embodiment used to heat the surface for 1 to 10 s. The second was an evaporative cooling method and the third was to blow hot air over the surface of the composite to inspect difficult-to-access areas. These methods successfully work on boron and carbon "composite" aluminum honeycomb structures and are not dependent on the type of composite. As shown in laboratory tests below, they also work on the "aluminum skin" honeycomb structures.

Figure 50:
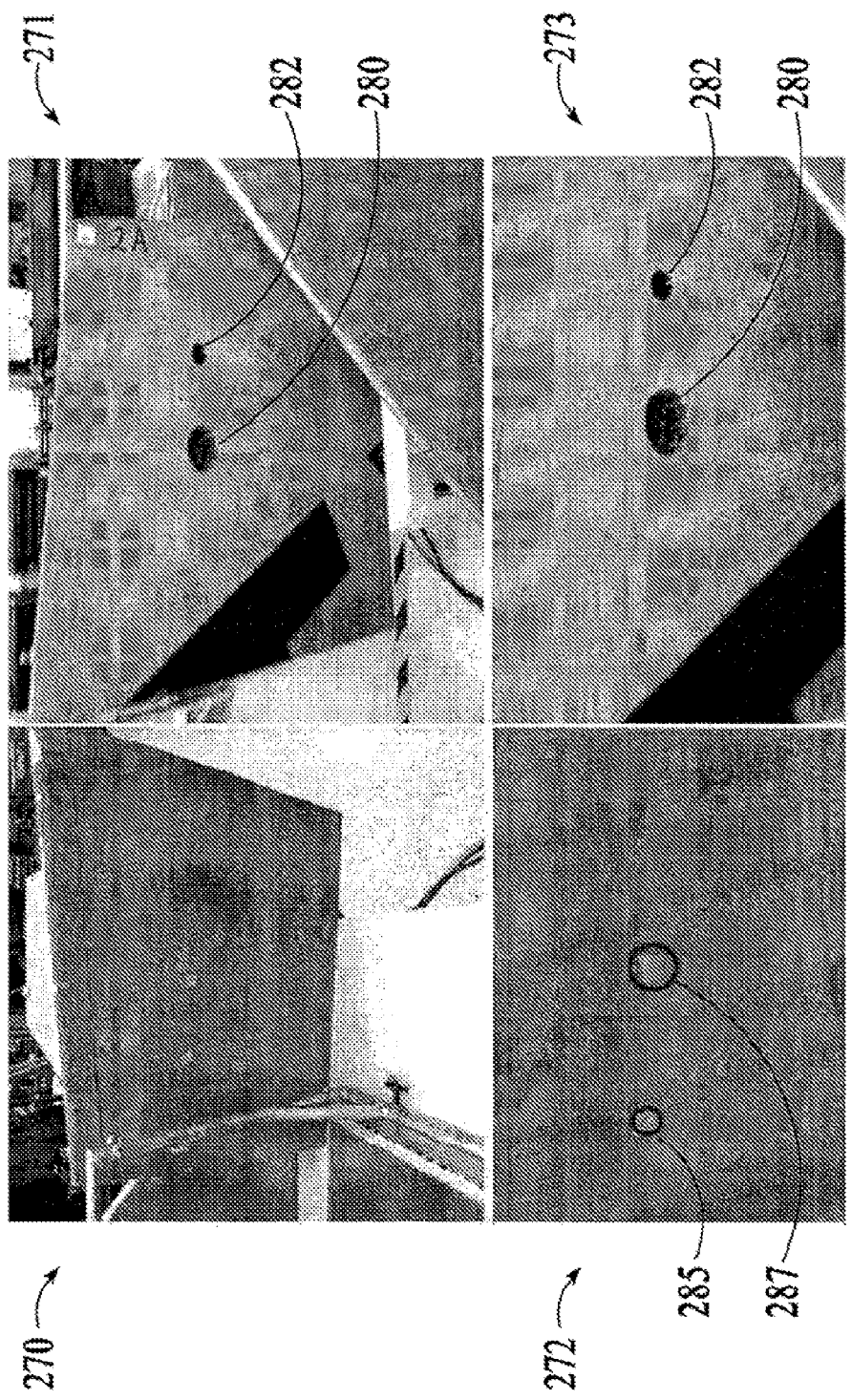
FIG. 50 illustrates two disbond defects (1-in. diameter and 2-in. diameter) that were created in an Al honeycomb structure with Al skin. The front and back are shown on the top and the bottom. The bottom is a blow-up of the top.
Figure 52:
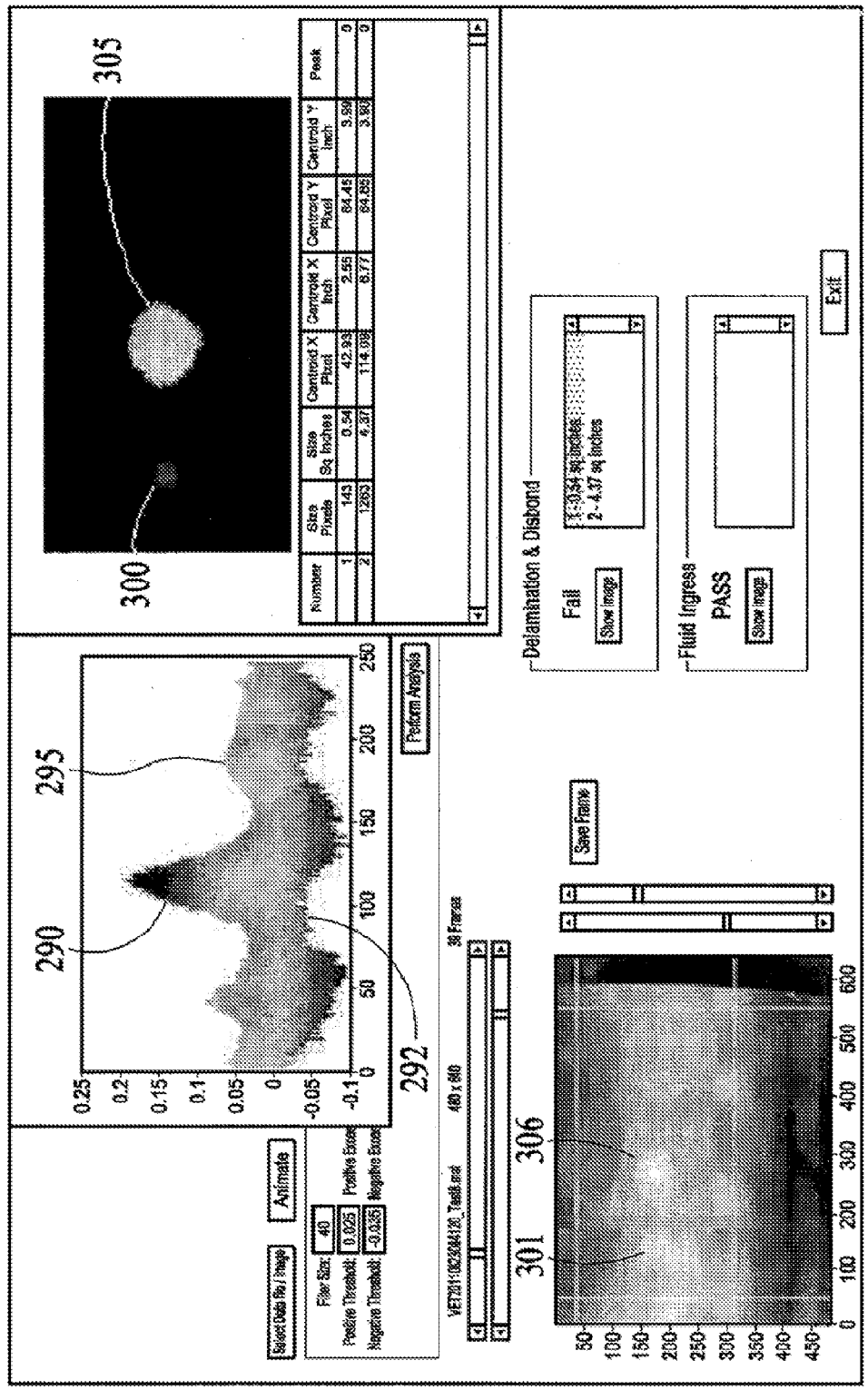
FIG. 52 illustrates the results of measurements on the two disbonds after heating the surface for 10 s or less. The vertical profile indicates a very strong disbond signal. The cluster results, the summary table and the IR image, all superimposed on the graphical user interface results, are shown.
Figure 54:
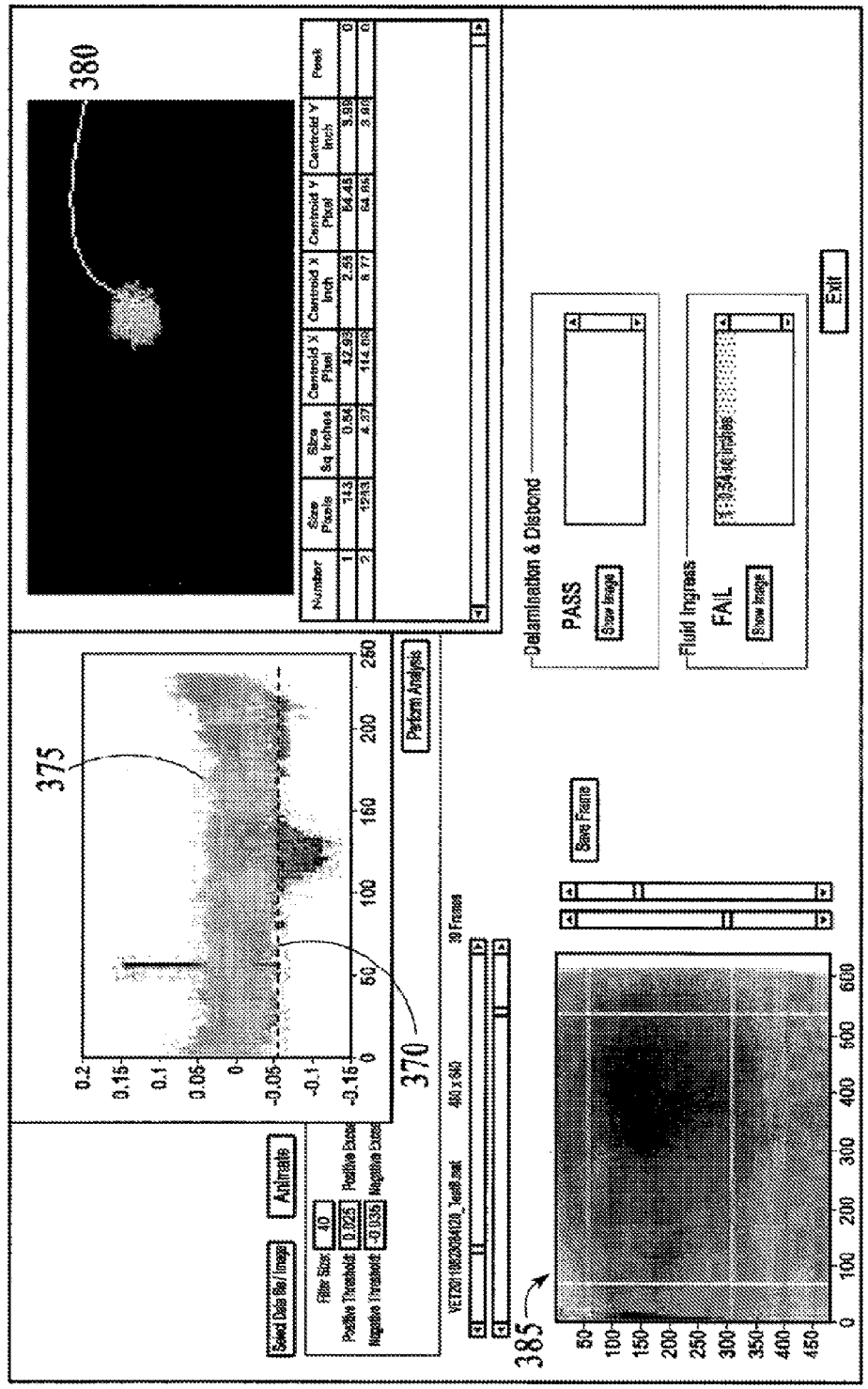
FIG. 54 illustrates the results for a 2-in. disbond when the composite is cooled by either spraying or rubbing water or alcohol on the surface and waiting for the signal to appear.

FIG. 50 shows the test section used in the tests with 1-in. and 2-in. disbonds. The real-time output of a measurement of the 1-in. and a 2-in. disbond is shown in FIG. 52, approximately 1 s after heating the aluminum surface for 10 s with the conductive heating mat; the defect signal persists for over 20 s. One also gets similar results if heating occurs for shorter periods. The real-time output of the IRIS is shown in the gray background on the lower left of the figure. The cluster plot showing the size and location of the disbond within the image is also shown. The profile view of the 1-in. and the 2-in. disbond defects clearly indicates their presence and their strength, which is significantly above the background IR intensities. FIG. 54 shows a confirmation measurement made by spraying (or wiping) the surface of the aluminum with ethanol before imaging with the IR camera. The resulting defect signal, which is cooler than the surrounding background, occurs within seconds after completing the spraying, but only persists for several seconds. Only the 2-in. disbond had been created at the time of this measurement. A threshold of 0.06 was used for both measurements.

Figure 53:
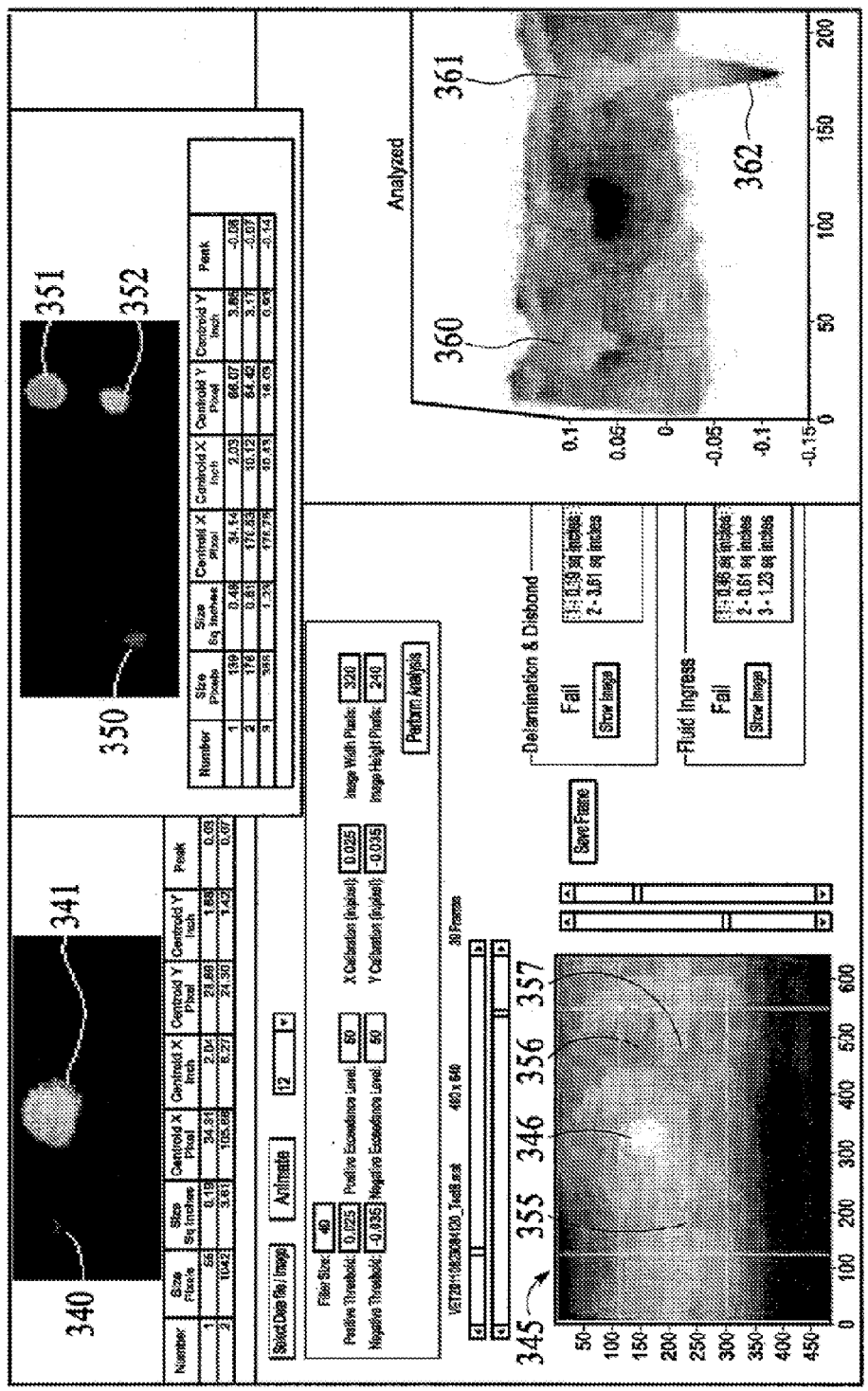
FIG. 53 illustrates the real-time output of the IRIS using a conductive heating method applied to an Al—Al Honeycomb section of an F-15 vertical stabilizer with a 0.25-in. radius section with water in the honeycomb, two 0.25-in. radius section with lubricant in the honeycomb (i.e., transmission oil), and two disbonds with a radius of 0.5 and 1 in., respectively.
Figure 55:
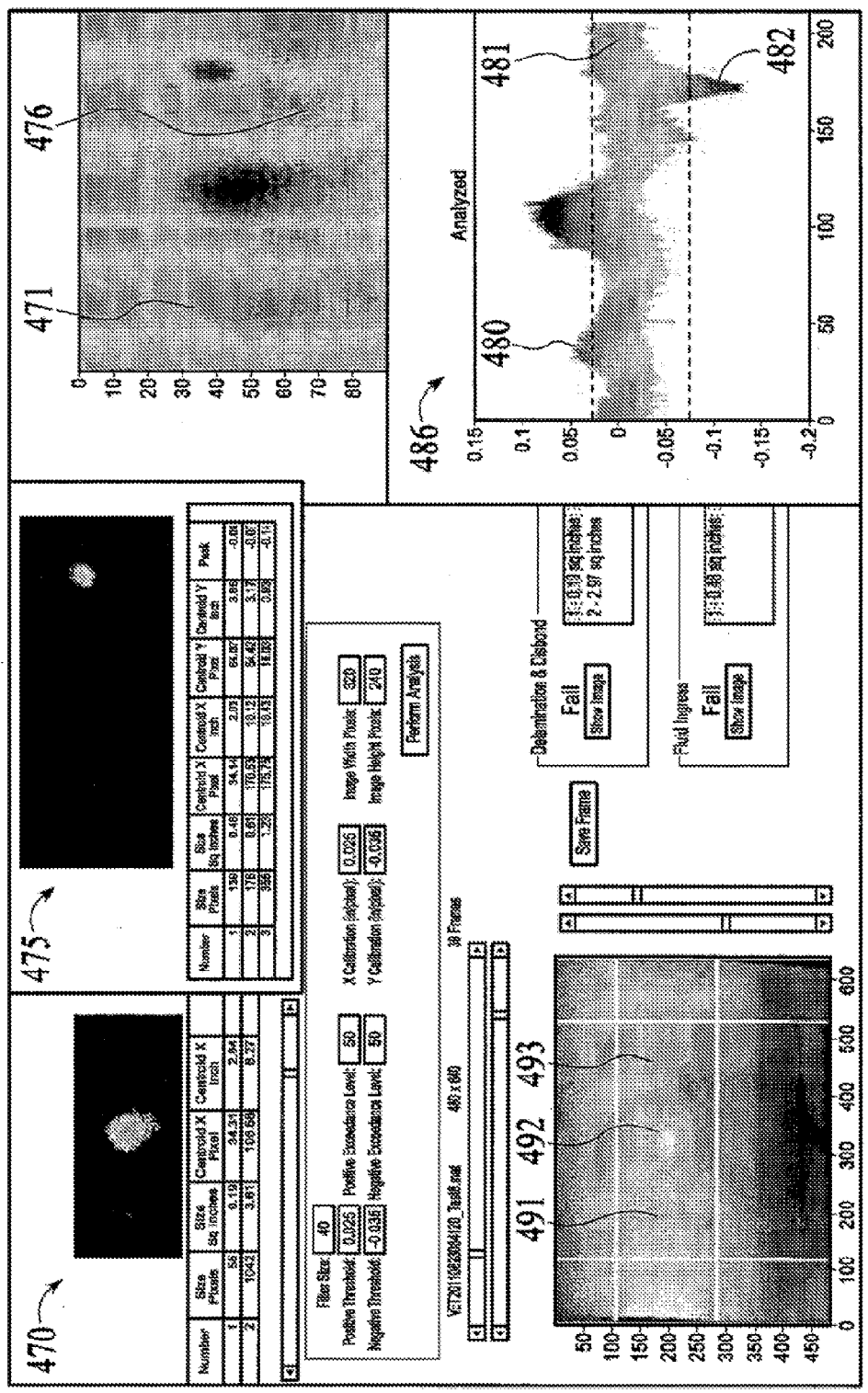
FIG. 55 illustrates real-time output of the IRIS using a conductive heating method applied to an Al—Al Honeycomb section of an F-15 vertical stabilizer with a 0.25-in.-radius section with water in the honeycomb and two disbonds with a radius of 0.5 and 1 in., respectively. The vertical profile shows the peak intensity of the fluid ingress and the two disbond defects and the thresholds used to detect them.

Additional tests were performed to demonstrate the capability for detecting, locating, and identifying fluid in the same section of Aluminum Skin-Aluminum Honeycomb aircraft structure used to illustrate the disbond detection and location capability described above. The first test was performed only with water in the honeycomb (FIG. 55). The second test was performed with two separate regions of lubricant in the honeycomb in addition to the region of water (FIG. 53). The two disbonds in the section were present in both tests.

The water ingress region was created in a region to the right of the larger (i.e., 1.0-in.-radius) disbond. The first lubricant ingress region was located immediately below the larger disbond and in the center of a large dent produced by a bird strike. The second lubricant ingress region was produced to the left of this lubricant region and immediately below the smaller disbond (i.e., 0.5-in. radius) region. All three fluid ingress regions were about 0.5 in. by 0.5 in. (0.25 in.$^2$). The standard conductive heating mat method detects and locates both types of fluid ingress and easily distinguishes both types of fluids from the disbond defects. This is straightforward, because disbond defect signals all have positive IR intensities, and all of the fluid ingress signals have negative intensities. The characteristics of the two fluids, water and lubricant, can also be distinguished from each other due to their signal strength and their decay time, because they have significantly different thermal properties.

FIG. 53 shows the results of the IRIS for detection and location of water ingress using the standard heating mat method. The measurement included the two disbonds that were described in the first set of demonstrations. All three defects were detected and located. This results in new, because it shows that the IRIS can detect and locate water that may be found in the honeycomb. The measurement was performed using 10 s of heating, which is identical to the procedure using for inspecting the boron composites on the F-15 vertical stabilizer. The real-time output of the IRIS is shown in the gray background on the lower left of the figure. The two cluster plots and the noise compensated plot at the top of the figure show the presence of the defects. The cluster plot on the left shows the disbond defects with amplitudes that are above the median ambient noise background, and the cluster plot on the right shows the water ingress with amplitudes that is below the median noise background. The profile view inserted on the lower right of the figure shows the normalized amplitude of each defect. The strength of these defects is clearly larger, in both a positive and negative sense, than the ambient background noise; thus, the presence of both the disbonds and water ingress are easy to identify. The thresholds used to process the data are shown by the dark dashed line for the disbonds and the light dashed line for the water ingress. The water-ingress defect is stronger and is more persistent than the disbond defects, and lasted longer than 20 s after removing the heater mat from the aluminum surface. The fluid ingress signal is 25% and 6% of the size of the smaller and larger disbonds, but is significantly stronger.

Other tests were performed to simulate the presence of lubricant in the honeycomb. Automotive transmission oil was used as the lubricant and each oil ingress was the same size at the water ingress. The results are shown in FIG. 53. The results are similar to those obtained in FIG. 55 for the water, but the transmission fluid ingress signal, although easily detected, resulted in a much weaker signal than the water ingress signal. The difference in the strength and decay properties of the lubricant vice the water provides a means for distinguishing water from lubricant. The detection, location, and identification of the disbonds and fluid ingress defects are possible because of the signal processing that automatically extracts the signal from the background noise of the image and displays the results.

Tongue and Groove Gridlock Aircraft Structure.

The method and a handheld apparatus were used to detect adhesive voids and damage in gridlock aircraft structures. The approach requires a 15-s measurement.

Figure 56:
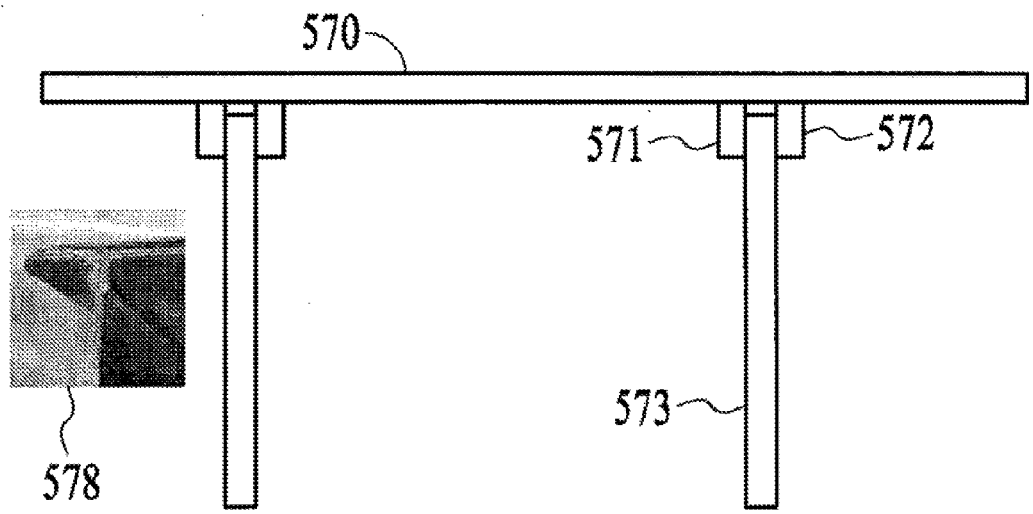
FIG. 56 illustrates a common defect in gridlock is a small void in the adhesive used to hold the I-beam in the channel.

The method detects any air gaps in the gridlock structure between the gridlock channel and the I-beam that fits into the channel. This gap can be a void in the adhesive, which is the most common defect, or a damaged channel in which the I-beam is disconnected from the channel. FIG. 56 illustrates the most common type of defect, a gap in the adhesive holding the I-beam in the channel.

Figure 58:
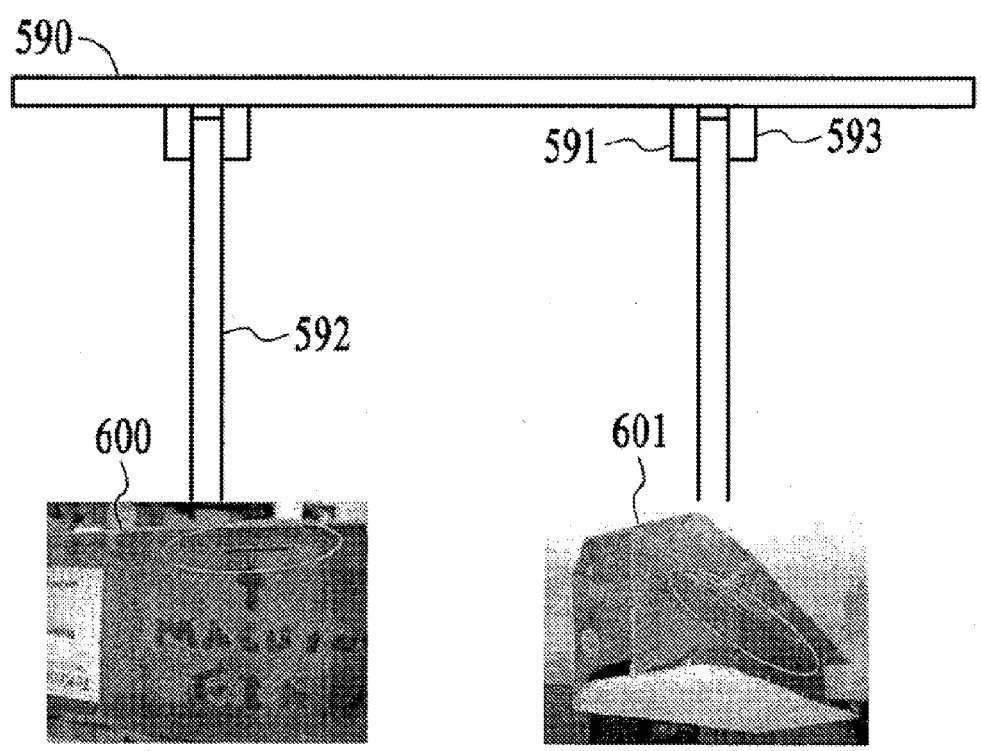
FIG. 58 illustrates the damaged side of the gridlock structure in which a 1-in. slot is cut into the channel to simulate an adhesive void (left), and the I-beam is dislocated from the channel to simulate a damage structure (right).

FIG. 58 shows the sample of gridlock used in the measurements that has both epoxy gaps and a region where the I-beam is disconnected from the channel. The top is the undamaged side of the gridlock, and the bottom contains both types of damage. The gridlock sample is 14-in. long, 3.5-to-4.5-in. wide and 3-in. high.

Figure 57:
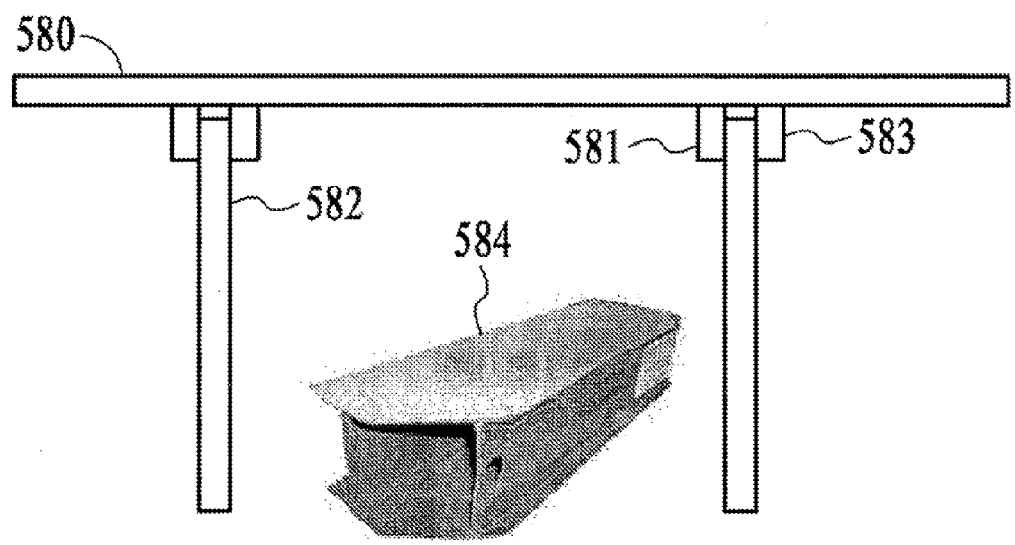
FIG. 57 illustrates an undamaged portion of gridlock.

FIG. 57 shows the undamaged side, and FIG. 58 shows the damaged side with both types of damage. There are two channels on each side of the sample, one located near the edge, and one located nearer to the center of the sample. The damaged channels on one side of the gridlock can be compared to the undamaged channels on the other side of the gridlock. The adhesive void was simulated by machining a 1-in.-long slot just below the channel located nearest to the edge of the sample. The disconnected channel, which is located nearest to the center of the sample, was simulated by breaking the channel with a hammer.

The same method used for detecting disbonds, delaminations, and water ingress in aluminum honeycomb composite structures using the IRIS for detecting adhesive voids and damage in aircraft gridlock, although the heating period may be shorter than 10 s when, as illustrated in FIG. 56, only small gaps in the adhesive exist. The total time for each measurement is less than 15 s. The signals produced by the undamaged channels and I-beams show up as negative troughs in the processed image. These negative troughs are not present when the defects are present. Similar responses were obtained for both the adhesive void and the disconnected channel.

Figure 59:
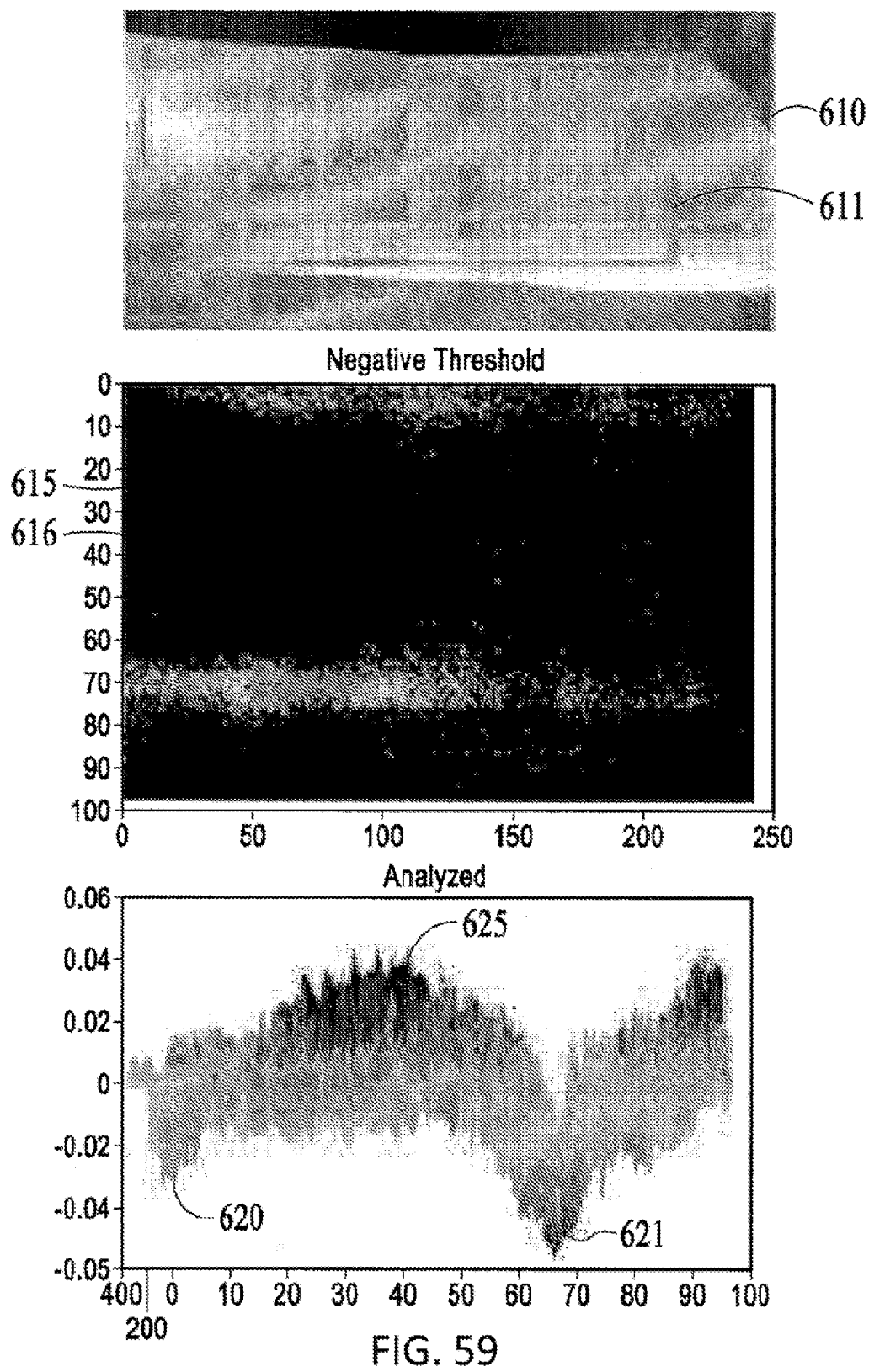
FIG. 59 illustrates the results of the IRIS for detecting the undamaged I-beam-channel sections located on the opposite side of the gridlock sample with the damage.
Figure 60:
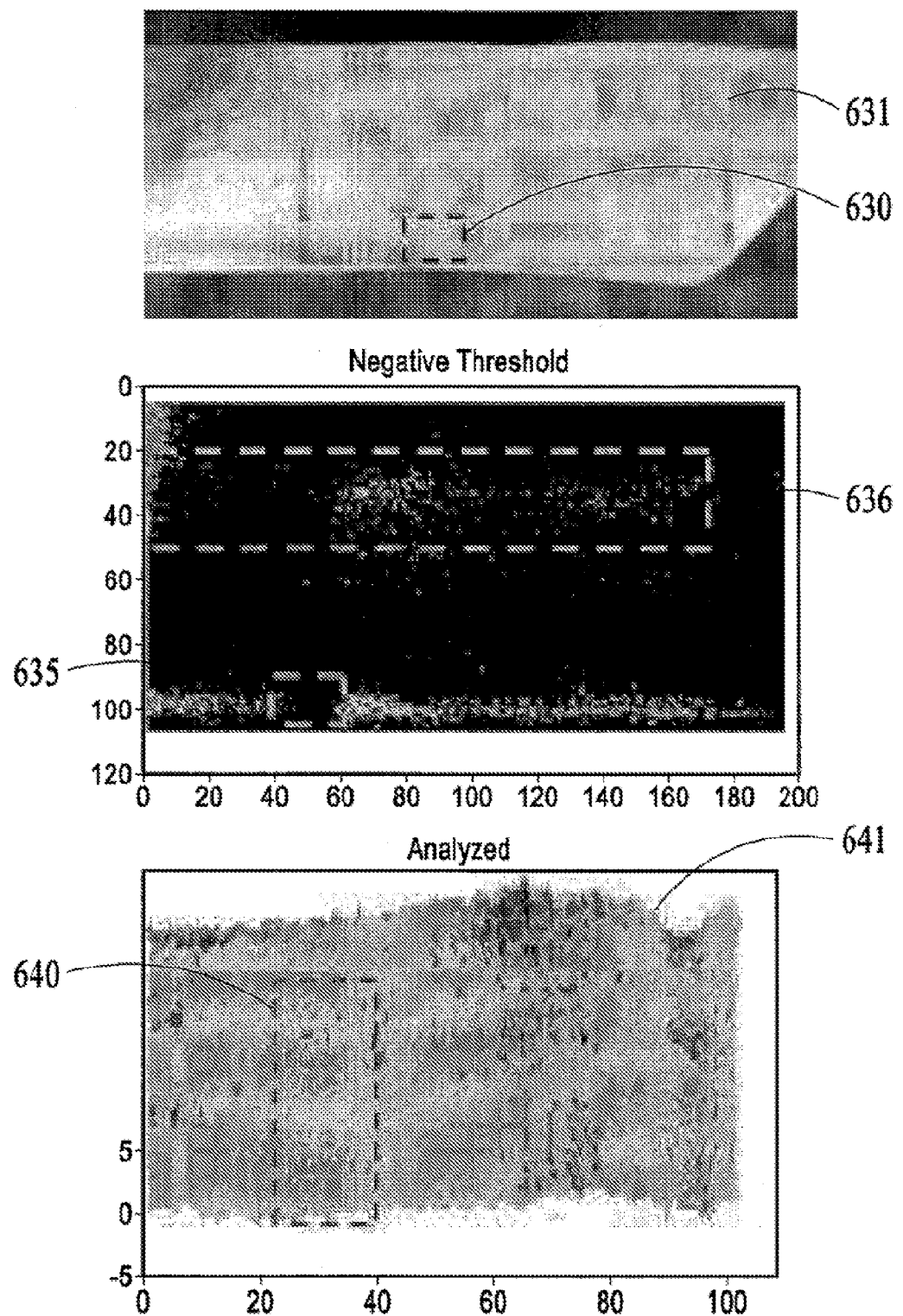
FIG. 60 illustrates the results of the IRIS for detecting the simulated 1-in. adhesive void (along the bottom edge) and the 8-in.-long damaged channel section (top one-third) in the gridlock sample. The results were obtained 1 s after heating the surface for 10 s.

As illustrated in FIGS. 59 and 60, it is important to note that the defects are not observed (or poorly observed) in the raw IR image. The noise-compensation processing algorithm is required to detect these defects. For routine inspection of gridlock, these tests indicate that an additional processing step (not described herein) will be added in which the gridlock response on the undamaged portion of the gridlock FIG. 59 shows the results of using the IRIS on the side of the gridlock sample without any damage (as shown in FIG. 57). FIG. 60 shows the results of using the IRIS on the side of the gridlock sample with the 1-in machined slot simulating an adhesive void (as shown in FIG. 58), which is located near the edge of the sample, and the damaged channel section in which the I-beam is not attached to the channel, which is located nearer to the center of the sample. The results are obtained about 1 s after removing the heat source.

Initial measurements were conducted on the undamaged side of the gridlock. The undamaged channels are easily detected. FIG. 59 shows the undamaged I-beam-channels located near the center and near the edge (top) of the sample, which correspond to the damaged sections located on the opposite side of the sample. The arrows indicate where the I-beams are located under the surface. The top plot is the raw IR image. The I-beam and channel show up as a negative IR response that runs along the entire length of the sample. The two-dimensional contour plot (center plot) in FIG. 59 shows only the IR intensities exceeding the negative threshold (−0.09). The two linear features, one near the top (above the 1-in. slot located on the other side of the gridlock sample) and one nearer the center of the figure (above the disconnected I-beam located on the other side of the gridlock sample) identify the undamaged channel sections. The vertical cross-section of these linear features, which is the bottom plot in FIG. 59, best illustrates the negative IR response associated with the undamaged I-beam and channel. These negative troughs are generated from the heating/cooling signature produced by the intact I-beams. These negative signals or troughs are not produced or are much less prevalent, however, when the channel and I-beam are not intact.

FIG. 60 illustrates the response of IRIS to the simulated adhesive void (i.e., 1-in. slot) and the disconnected channel section. In both cases the damaged areas can be identified because the IR response is not negative. There is some negative response, because the channel stub still remains. The 1-in. slot is located by the dotted box. The disconnected I-beam is located by the elongated rectangular dotted box. The bottom plot shows a 3D tilted view of the negative IR intensities showing the less negative IR intensities where the defects are located. These responses will be much clearer when the IR measurements are made on larger areas where longer or multiple channels runs will be present.

While the preferred embodiment of the present invention can be used to inspect gridlock now, for better results, two changes could be made. The first is to sample at 30 Hz and average to 1 s. The averaging, which is unnecessary for the composite measurements because the defects have such a strong IR response, will help reduce the noise and improve the signal-to-noise ratio (SNR) of damaged gridlock. The second is to use the adjacent undamaged sections of I-beam-channel as references for identifying small adhesive voids.

What is claimed:

1. A method for detection of defects in a composite structure comprising the steps of:
    positioning an infrared camera at a known distance from the composite structure;
    positioning a heater over an area of the composite structure;
    applying heat from the heater onto the area of the composite structure changing the temperature of the composite structure;
    removing the heat applied by the heater from the area of the composite structure;
    collecting a data set of infrared images from the area of said composite structure heated by the heater, including collecting a first set of the infrared images within a first time period after removing the heat from the area and collecting a second set of the infrared images within a second time period after removing the heat from the area, wherein the second time period is after the first time period;
    processing the data set with a computer, including cancelling the background noise in the infrared images of said composite structure; and
    identifying defects in said composite structure using the processed data set including determining a delamination in the composite structure based on one or more of the first set of infrared images, and determining a fluid egress or disbond in the composite structure based on one or more of the second set of infrared images.

2. The method of claim 1, wherein the first time period is around 2-5 seconds and the second time period is around 20-40 seconds.

3. The method of claim 1, where said composite structure is comprised of a composite material including carbon or boron.

4. The method of claim 1, where said background noise in the infrared images is cancelled by applying a filter to the infrared images and subtracting the filtered infrared images from said infrared images.

5. The method of claim 1, further comprising the step of determining a position of the defects relative to a surface of said composite structure.

6. The method of claim 5, where the position is determined using acoustic sensors placed on the composite structure and on or near the infrared camera using triangulation.

7. The method of claim 5, where the position is determined from a pattern of small heating or cooling elements that produce detectable signals as part of each infrared image.

8. The method of claim 5, where the position is determined with an infrared ruler read by the infrared camera.

9. The method of claim 5, where the position is determined using an optical ruler read by a camera.

10. The method of claim 5, where the position is determined using a ruler comprised of fiducial marker elements, which are warmer or cooler than the surrounding area and are arranged in a pattern that can be viewed by said infrared camera.

11. The method of claim 9, where said optical ruler is comprised of fiducial marker elements, which produce detectable optical signals and are arranged in a pattern that can be viewed by said camera.

12. The method of claim 11, where the fiducial marker elements are light bulbs.

13. The method of claim 1, where the composite structure is heated at a surface of the composite structure.

14. The method of claim 1, where the composite structure is cooled at a surface of the composite structure.

15. The method of claim 14, where said composite structure is cooled by evaporative cooling.

16. The method of claim 10, where said fiducial markers are electrical resistors connected to a current source.

17. The method of claim 10, where said fiducial markers are small light bulbs.

18. The method of claim 10, where said fiducial markers are comprised of material that has a different heat capacity than surrounding material of said ruler.

19. The method of claim 10, where said fiducial markers are metal.

20. The method of claim 10, where said fiducial markers are heated or cooled before the infrared camera collects the infrared images.

21. The method of claim 10, where said fiducial markers are cooled with a thermo-cooling device connected to a current source.

22. The method of claim 1, where a single decision criterion is used to determine the presence of defects in the infrared image after said noise cancellation, where a different decision can be is used for each type of defect to be detected.

23. The method of claim 22, where the presence of defects in the infrared image after said noise cancellation is determined by using a threshold and identifying if the amplitude of any pixels are larger than the threshold, where a different threshold can be is used for each type of defect to be detected.

24. The method of claim 1, where at least two decision criteria are used to determine the presence of any the defects in the infrared image after said noise cancellation.

25. The method of claim 24, where said criteria comprise a threshold and a set number of pixels that must exceed said threshold, where a different decision criterion is used for each type of defect to be detected.

26. The method of claim 23, where the threshold is evaluated for at least one pixel in said noise cancelled infrared image, where a different threshold is used for each type of defect to be detected.

27. The method of claim 25, where the threshold is evaluated for a pre determined number of two or more pixels in close proximity, where a different threshold and a different number of pixels in close proximity are used for each type of defect to be detected.

28. The method of claim 23, where said threshold is determined from historical background noise after said noise cancellation for each type of defect to be detected.

29. The method of claim 23, where said threshold is determined adaptively from said background noise after said noise cancellation on the infrared image being analyzed for each type of defect to be detected.

30. The method of claim 29, where said adaptive threshold is determined by computing a mean and standard deviation of said noise cancelled infrared images and using a threshold at a pre-determined multiple of the standard deviation.

31. The method of claim 30, where said threshold is defined to provide a specific probability of detection and a specific probability of false alarm.

32. The method of claim 30, where said mean and standard deviation are computed at one or more locations on said noise cancelled infrared images to determine if any defect signals are present, comprising the steps of comparing a median value for each location and the mean computed for smaller regions at each location, and using said locations where there are no large differences between the median value and the means for the smaller regions to determine said threshold.

33. The method of claim 30, where said mean and standard deviation are computed at one or more locations on said noise cancelled infrared image to determine if any defect signals are present, comprising the steps of comparing the mean or median value for each location to a maximum or a minimum value, depending on which type of defect is being detected, and using said locations where there are no large differences between the mean or median and the maximum or minimum values to determine said threshold.

34. The method of claim 32, where said mean and standard deviation are computed at one or more locations on said noise cancelled infrared image to determine if any defect signals are present, comprising the steps of comparing the median value for each location and the mean values computed for smaller regions at each location determined by the number of pixels use to determine the threshold, and using said locations where there are no large differences between the median and the means to determine said threshold.

35. The method of claim 30, where said mean and standard deviation are computed at one or more locations on said noise cancelled infrared image to determine if any defect signals are present, comprising the steps of comparing the mean or median value for the entire location to a maximum or a minimum, depending on which type of defect is being detected, and using said locations where there are no large differences between the mean or median value determined by the number of pixels used to determine the threshold, and the maximum or the minimum values to determine said threshold.

36. The method of claim 1, where the disbonds and the delaminations are detected as positive threshold exceedances in said noise cancelled infrared images.

37. The method of claim 36, where the disbonds and the delaminations are identified from their different temporal behavior, where the infrared images from said delaminations occur immediately after said heating or cooling of said composite structure and the infrared images from said disbonds take longer to appear and dissipates slowly over time.

38. The method of claim 37, where said delamination will occur within 1 to 10 seconds of applying or removing said heat or a cooling source and will be sufficiently dissipated and said disbonds are detected after 20 to 30 seconds of applying or removing said heating or the cooling source.

39. The method of claim 36, where the disbonds and the delaminations are identified from differences in the strength of their infrared images, where the strength of the infrared images produced by said delaminations is about two times larger than the strength of the infrared images produced by the disbonds.

40. The method of claim 36, where the disbonds and the delaminations are identified from differences in the strength and temporal behavior of their infrared images.

41. The method of claim 1, where fluid contained inside honeycomb cells are detected as negative threshold exceedances in the noise cancelled infrared images.

42. The method of claim 39, where said fluid is identified from said disbonds and delaminations because the infrared images from said fluid is negative.

43. The method of claim 41, where said fluid occurs within 1 to 5 seconds and persist for a period of time.

44. The method of claim 41, where the fluid contained inside the honeycomb cells is distinguished from a buildup of epoxy by performing a measurement on both sides of said composite structure, where the fluid is present if it is detected on both sides of said composite structure.

45. The method of claim 41, where the fluid contained inside the honeycomb cells is distinguished from a buildup of epoxy by performing a measurement on both sides of said composite structure after tilting said composite structure causing the fluid to flow to each side.

46. The method of claim 1, where a size of the defects are determined by performing a cluster analysis on the noise canceled infrared images, where a cluster is determined from the number of pixels that exceed a detection threshold and are in close proximity to each other and computing the area of said cluster.

47. The method of claim 1, where the location of the defects on said infrared images is determined by performing a cluster analysis on a noise cancelled infrared images, where a cluster is determined from a number of pixels that exceed a detection threshold and are in close proximity to each other and computing the centroid of said cluster.

48. The method of claim 4 where a composite map of spatial coverage and presence and type of defect is output relative to said composite structure being inspected from all of the individual infrared images obtained during said inspection using a means of locating each said infrared image automatically and in real time.

49. The method of claim 36, where a processor analyzes the infrared images being collected in real time to identify when the heater was removed from said composite structure by comparing cool infrared signals obtained just before the heater is released to strong (saturated) infrared signals obtained immediately after said mat was released and then to select the infrared images at a specified time after said heat removal when the infrared signals due to delaminations, disbands, and fluid ingress defects can be differentiated.

50. An apparatus, comprising:
   a frame to position next to different surface areas of a composite material;
   a heater attached to the frame to heat the different surface areas of the composite material where the frame is positioned; and
   an infrared camera attached to the frame to collect frames of image data from the surface areas after the heater applies heat to the composite material, the infrared camera providing the image data to a computer to identify defects in the composite material based on the image data, wherein the computer is further configured to:

identify a first set of the frames in the image data captured within a first time period after the heater stops heating the surface areas;

use one or more of the first set of frames from the image data to detect delaminations in the composite material;

identify a second set of the frames in the image data within a second time period after the first time period; and use one or more of the second set of the frames in the image data to detect a fluid egress or disbond in the composite structure.

51. The apparatus of claim 50, further comprising:
   a first hinge pivotally attaching the heater to the frame and moving the heater from a first position over the surface areas where the frame is positioned to a second position away from the surface areas; and
   a second hinge pivotally attaching the infrared camera from a first position away from where the heater is heating the surface areas of the composite material to a second position over the surface areas where the heater previously heated the composite material.

52. The apparatus of claim 50, further comprising:
   a sensor configured to:
   detect when the heater stops heating, or is about to stop heating, the surface areas of the composite material; and
   activate the infrared camera to start collecting the frames of image data from the surface areas of the composite material in response to the sensor detecting the heater stop heating, or about to stop heating, the surface areas.

* * * * *